United States Patent
Spranger et al.

(10) Patent No.: US 12,061,186 B2
(45) Date of Patent: Aug. 13, 2024

(54) COMPOSITIONS AND METHODS FOR USING CROSS-DRESSING TO ENHANCE ANTI-TUMOR IMMUNE RESPONSES

(71) Applicant: Massachusetts Institute of Technology, Cambridge, MA (US)

(72) Inventors: Stefani Spranger, Boston, MA (US); Ellen Duong, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 148 days.

(21) Appl. No.: 17/348,704

(22) Filed: Jun. 15, 2021

(65) Prior Publication Data

US 2021/0389301 A1   Dec. 16, 2021

Related U.S. Application Data

(60) Provisional application No. 63/039,166, filed on Jun. 15, 2020.

(51) Int. Cl.
| | | |
|---|---|---|
| *G01N 15/14* | (2024.01) | |
| *C12Q 1/6869* | (2018.01) | |
| *G01N 33/50* | (2006.01) | |
| *G01N 33/574* | (2006.01) | |
| *G01N 33/68* | (2006.01) | |

(52) U.S. Cl.
CPC ....... *G01N 33/5047* (2013.01); *C12Q 1/6869* (2013.01); *G01N 15/14* (2013.01); *G01N 33/57492* (2013.01); *G01N 33/6893* (2013.01)

(58) Field of Classification Search
CPC .................................................. G01N 33/5047
USPC ........................................................ 435/7.23
See application file for complete search history.

(56) References Cited

FOREIGN PATENT DOCUMENTS

WO   WO 2018/035364 A1   2/2018

OTHER PUBLICATIONS

Diamond et al (J Exp Med, 2011, 208(10): 1989-2003).*
De Veer et al (J Leukoc Biol, 2001, 69: 912-920).*
Tel et al (The Journal of Immunology, 2013, 191: 5005-5012).*
Da Silva et al (Biomaterials, 2019, 220, 119417: 1-14).*
PCT/US2021/037509, Oct. 21, 2021, International Search Report and Written Opinion.
PCT/US2021/037509, Dec. 29, 2022, International Preliminaray Report on Patentability.
Ishizuka et al., Loss of ADAR1 in tumours overcomes resistance to immune checkpoint blockade. Nature. Jan. 2019;565(7737):43-48. doi: 10.1038/s41586-018-0768-9. Epub Dec. 17, 2018. PMID: 30559380; PMCID: PMC7241251.
Li et al., Cross-dressed CD8α+/CD103+ dendritic cells prime CD8+ T cells following vaccination. Proc Natl Acad Sci U S A. Jul. 31, 2012;109(31):12716-21. doi: 10.1073/pnas.1203468109. Epub Jul. 16, 2012. PMID: 22802630; PMCID: PMC3411977.
Liu et al., Tumor-derived IFN triggers chronic pathway agonism and sensitivity to ADAR loss. Nat Med. Jan. 2019;25(1):95-102. doi: 10.1038/s41591-018-0302-5. Epub Dec. 17, 2018. PMID: 30559422.
Spranger et al., Tumor-Residing Batf3 Dendritic Cells Are Required for Effector T Cell Trafficking and Adoptive T Cell Therapy. Cancer Cell. May 8, 2017;31(5):711-723.e4. doi: 10.1016/j.ccell.2017.04.003. PMID: 28486109; PMCID: PMC5650691.
Villani et al., Single-cell RNA-seq reveals new types of human blood dendritic cells, monocytes, and progenitors. Science. Apr. 21, 2017;356(6335):eaah4573. doi: 10.1126/science.aah4573. PMID: 28428369; PMCID: PMC5775029.
Wakim et al., Cross-dressed dendritic cells drive memory CD8+ T-cell activation after viral infection. Nature. Mar. 31, 2011;471(7340):629-32. doi: 10.1038/nature09863. PMID: 21455179; PMCID: PMC3423191.
Zeng et al., Extracellular vesicle-mediated MHC cross-dressing in immune homeostasis, transplantation, infectious diseases, and cancer. Semin Immunopathol. Sep. 2018;40(5):477-490. doi: 10.1007/s00281-018-0679-8. Epub Mar. 28, 2018. PMID: 29594331; PMCID: PMC6162176.
International Search Report and Written Opinion mailed Oct. 21, 2021, for Application No. PCT/US2021/037509.
International Preliminary Report on Patentability mailed Dec. 29, 2022, for Application No. PCTUS2021/037509.
Barry et al., A natural killer-dendritic cell axis defines checkpoint therapy-responsive tumor microenvironments. Nat Med. Aug. 2018;24(8):1178-1191. DOI: 10.1038/s41591-018-0085-8. Epub Jun. 25, 2018.
Bonaccorsi et al., Acquisition and Presentation of Tumor Antigens by Dendritic Cells. Crit Rev Immunol. 2015;35(5):349-64.
Cohen, New activities for old antibiotics. Nat Microbiol. May 2018;3(5):531-532. doi: 10.1038/s41564-018-0152-4. Erratum in: Nat Microbiol. Jul. 2018;3(7):844.
Duong et al., Type I interferon activates MHC class I-dressed CD11b+ conventional dendritic cells to promote protective anti-tumor CD8+ T cell immunity. Immunity. Feb. 8, 2022;55(2):308-323.e9. doi: 10.1016/j.immuni.2021.10.020. Epub Nov. 19, 2021.
Duong et al., Novel dsRNA-sensing dendritic cells enhance anti-tumor immunity. J. Immunother Cancer. 2019; 7(Supp 1): 1 page.
Duong et al., Non-canonical cross-presenting dendritic cells mediate anti-tumor immunity. J. Immunother Cancer 2018; 6(Supp 1): 1 page.
Fessenden et al.,. A team effort: natural killer cells on the first leg of the tumor immunity relay race. J Immunother Cancer. Jul. 9, 2018;6(1):67.
Spranger et al., Impact of tumor-resident DC on antitumor immunity. Cancer Immunol Res. Mar. 2020; 8(3): 283.
Alcantara-Hernandez et al., High-Dimensional Phenotypic Mapping of Human Dendritic Cells Reveals Interindividual Variation and Tissue Specialization. Immunity. Dec. 19, 2017;47(6):1037-1050.e6. doi: 10.1016/j.immuni.2017.11.001. Epub Dec. 5, 2017.

(Continued)

*Primary Examiner* — Sean E Aeder
(74) *Attorney, Agent, or Firm* — Wolf, Greenfield & Sacks, P.C.

(57) ABSTRACT

Provided herein are compositions and methods of use relating to a novel class of dendritic cells, referred to herein as ISG+ DC, having anti-tumor activity.

16 Claims, 27 Drawing Sheets

Specification includes a Sequence Listing.

(56) References Cited

OTHER PUBLICATIONS

Barbie et al., Systematic RNA interference reveals that oncogenic KRAS-driven cancers require TBK1. Nature. Nov. 5, 2009;462(7269):108-12. doi: 10.1038/nature08460. Epub Oct. 21, 2009.

Böttcher et al., NK Cells Stimulate Recruitment of cDC1 into the Tumor Microenvironment Promoting Cancer Immune Control. Cell. Feb. 22, 2018;172(5):1022-1037.e14. doi: 10.1016/j.cell.2018.01. 004. Epub Feb. 8, 2018.

Broz et al., Dissecting the tumor myeloid compartment reveals rare activating antigen-presenting cells critical for T cell immunity. Cancer Cell. Nov. 10, 2014;26(5):638-52. doi: 10.1016/j.ccell.2014. 09.007. Epub Oct. 16, 2014.

Butler et al., Integrating single-cell transcriptomic data across different conditions, technologies, and species. Nat Biotechnol. Jun. 2018;36(5):411-420. doi: 10.1038/nbt.4096. Epub Apr. 2, 2018.

Chiappinelli et al., Inhibiting DNA Methylation Causes an Interferon Response in Cancer via dsRNA Including Endogenous Retroviruses. Cell. Aug. 27, 2015;162(5):974-86. doi: 10.1016/j.cell. 2015.07.011. Erratum in: Cell. Feb. 25, 2016;164(5):1073. Buhu, Sadna [corrected to Budhu, Sadna]; Mergoub, Taha [corrected to Merghoub, Taha]. Erratum in: Cell. Apr. 6, 2017;169(2):361.

Fuertes et al., Host type I IFN signals are required for antitumor CD8+ T cell responses through CD8{alpha}+ dendritic cells. J Exp Med. Sep. 26, 2011;208(10):2005-16. doi: 10.1084/jem.20101159. Epub Sep. 19, 2011.

Fuertes et al., Type I interferon response and innate immune sensing of cancer. Trends Immunol. Feb. 2013;34(2):67-73. doi: 10.1016/j.it.2012.10.004. Epub Oct. 31, 2012.

Hildner et al., Batf3 deficiency reveals a critical role for CD8alpha+ dendritic cells in cytotoxic T cell immunity. Science. Nov. 14, 2008;322(5904):1097-100.

Liu et al., Dual Targeting of Innate and Adaptive Checkpoints on Tumor Cells Limits Immune Evasion. Cell Rep. Aug. 21, 2018;24(8):2101-2111.

Mayakonda et al., Maftools: efficient and comprehensive analysis of somatic variants in cancer. Genome Res. Nov. 2018;28(11):1747-1756. doi: 10.1101/gr.239244.118. Epub Oct. 19, 2018.

Mumberg et al., CD4(+) T cells eliminate MHC class II-negative cancer cells in vivo by indirect effects of IFN-gamma. Proc Natl Acad Sci U S A. Jul. 20, 1999;96(15):8633-8. doi: 10.1073/pnas. 96.15.8633. Erratum in: Proc Natl Acad Sci U S A Feb. 29, 2000;97(5):2397.

Ribas et al., Cancer immunotherapy using checkpoint blockade. Science. Mar. 23, 2018;359(6382):1350-1355. doi: 10.1126/science. aar4060. Epub Mar. 22, 2018.

Roberts et al., Critical Role for CD103(+)/CD141(+) Dendritic Cells Bearing CCR7 for Tumor Antigen Trafficking and Priming of T Cell Immunity in Melanoma. Cancer Cell. Aug. 8, 2016;30(2):324-336. doi: 10.1016/j.ccell.2016.06.003. Epub Jul. 14, 2016.

Roberts et al., Tumors exploit dedicated intracellular vesicles to program T cell responses. BioRxiv. 2019; 691873. 22 pages.

Rooney et al., Molecular and genetic properties of tumors associated with local immune cytolytic activity. Cell. Jan. 15, 2015;160(1-2):48-61.

Salmon et al., Expansion and Activation of CD103(+) Dendritic Cell Progenitors at the Tumor Site Enhances Tumor Responses to Therapeutic PD-L1 and BRAF Inhibition. Immunity. Apr. 19, 2016;44(4):924-38.

Schmid et al., AXL receptor tyrosine kinase is required for T cell priming and antiviral immunity. Elife. Jun. 28, 2016;5:e12414.

Spranger et al., Melanoma-intrinsic β-catenin signalling prevents anti-tumour immunity. Nature. Jul. 9, 2015;523(7559):231-5. doi: 10.1038/nature14404. Epub May 11, 2015.

Spranger et al., Density of immunogenic antigens does not explain the presence or absence of the T-cell-inflamed tumor microenvironment in melanoma. Proc Natl Acad Sci U S A. Nov. 29, 2016;113(48):E7759-E7768. doi: 10.1073/pnas. 1609376113. Epub Nov. 11, 2016.

Subraminian et al., Gene set enrichment analysis: a knowledge-based approach for interpreting genome-wide expression profiles. Proc Natl Acad Sci U S A. Oct. 25, 2005;102(43):15545-50. doi: 10.1073/pnas.0506580102. Epub Sep. 30, 2005.

Tumeh et al., PD-1 blockade induces responses by inhibiting adaptive immune resistance. Nature. Nov. 27, 2014;515(7528):568-71.

Williams et al., The EGR2 targets LAG-3 and 4-1BB describe and regulate dysfunctional antigen-specific CD8+ T cells in the tumor microenvironment. J Exp Med. Feb. 2017;214(2):381-400. doi: 10.1084/jem.20160485. Epub Jan. 23, 2017.

Woo et al., Sting-dependent cytosolic DNA sensing mediates innate immune recognition of immunogenic tumors. Immunity. Nov. 20, 2014;41(5):830-42. doi: 10.1016/j.immuni.2014.10.017. Epub Nov. 5, 2014.

Zelenay et al., The dendritic cell receptor DNGR-1 controls endocytic handling of necrotic cell antigens to favor cross-priming of CTLs in virus-infected mice. J Clin Invest. May 2012;122(5):1615-27. doi: 10.1172/JCI60644. Epub Apr. 16, 2012.

Zilionis et al., Single-Cell Transcriptomics of Human and Mouse Lung Cancers Reveals Conserved Myeloid Populations across Individuals and Species. Immunity. May 21, 2019;50(5):1317-1334. e10. doi: 10.1016/j.immuni.2019.03.009. Epub Apr. 9, 2019.

\* cited by examiner

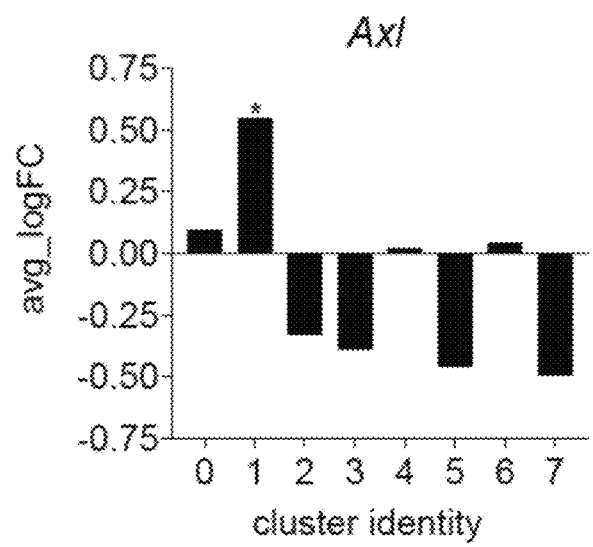
FIG. 2G
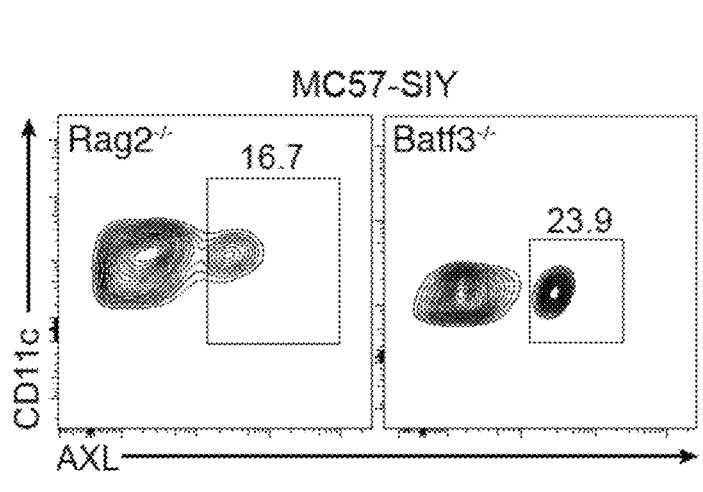 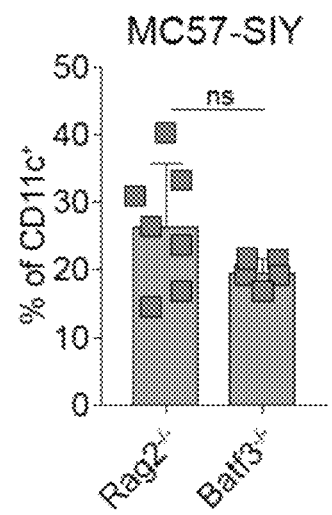
FIG. 2H                FIG. 2I

COMPOSITIONS AND METHODS FOR USING CROSS-DRESSING TO ENHANCE ANTI-TUMOR IMMUNE RESPONSES

RELATED APPLICATIONS

This application claims the benefit of the filing date of U.S. Provisional Application No. 63/039,166 filed on Jun. 15, 2020, the entire contents of which are incorporated by reference herein.

FEDERALLY SPONSORED RESEARCH

This invention was made with Government support under Grant No. R00 CA204595 awarded by the National Institutes of Health (NIH). The Government has certain rights in the invention.

BACKGROUND OF INVENTION

Checkpoint blockade therapy (CBT) has revolutionized the treatment of cancer through its remarkable ability to reinvigorate dysfunctional T cells that exhibit impaired effector function (1). Tumors harboring a pre-existing T cell infiltrate are more sensitive to CBT (2). However, optimal anti-tumor immune responses rely on additional features beyond T cell numbers. In fact, sustained presence of highly functional T cells in the tumor microenvironment (TME) has been shown to promote tumor control, whereas dysfunctional T cells have been associated with tumor escape (3). While the dysfunctional T cell phenotype is well-understood from viral and cancer models (4), much less is known about the factors that maintain T cells in a productive, functional state.

Antigen-presenting cells can profoundly shape the landscape of tumor-infiltrating T cells. Recent studies describe novel roles for tumor-resident Batf3-driven CD103$^+$ dendritic cells (DC1) in recruiting effector T cells to the TME (5) and providing local T cell stimulation (6). Boosting DC numbers or function enhances responses to CBT, suggesting that DC may contribute to the reactivation of dysfunctional T cells (7). However, the identities and phenotypes of tumor-resident DC that induce and maintain highly functional T cell responses, and thus enable spontaneous tumor clearance, remain elusive. Uncovering these stimulatory DC and understanding their functions can open new therapeutic avenues to boost anti-tumor immunity and prevent T cell dysfunction.

SUMMARY OF INVENTION

This disclosure is based on the surprising discovery of a novel class of dendritic cells, the presence and/or activation of which in a tumor microenvironment correlates with tumor regression, particularly in response to secondary therapies such as but not limited to checkpoint inhibitor therapy. This novel class of dendritic cells, referred to herein as interferon-stimulated gene signature dendritic cells or ISG+ DCs, has unique mRNA and protein expression profiles. Importantly, these cells are able to present tumor antigen in the context of MHC Class I in a manner that does not require internalization and digestion of tumor cells and/or antigens, as would be expected to occur in classical antigen cross-presentation. Instead, these cells present tumor antigen in the context of MHC Class I in a manner referred to herein as "cross-dressing", a phenomenon that has not been heretofore described. Cross-dressing ISG+ DC are activated by sensing tumor-derived double-stranded RNA (dsRNA). The presence of ISG+ DC in tumors may be a good prognostic factor and these cells may be harnessed to induce a more robust anti-tumor response in such subjects. These findings therefore provide the basis for methods to identify and triage subjects based on their tumor ISG+ DC profile, and/or to treat subjects to induce or enhance the cross-dressing phenomenon for beneficial effect.

Accordingly, this disclosure provides, inter alia, compositions comprising ISG+ DC cells, methods of detecting such cells and measuring their levels in a subject or in a tissue (e.g., a tumor) with the subject, methods of enhancing activity and/or increasing number of such cells, and methods of identifying subjects that would benefit from enhancing activity and/or number of such cells, and methods of treating particular conditions (e.g., a cancer) by enhancing activity and/or number of such cells.

Thus, in one aspect, this disclosure provides a method of detecting and/or measuring ISG+ DC in a tumor, comprising obtaining a solid tumor sample from a subject, and detecting and/or measuring the level of interferon-stimulated gene signature dendritic cells (ISG+ DC) present in the tumor sample.

In some embodiments, ISG+ DC are detected based on transcriptional or gene expression or mRNA profile. The transcriptional profiles are typically described by the genes (or markers) that are expressed in an ISG+ DC cell or population. In some embodiments, the transcriptional or gene expression or mRNA profile is obtained using bulk-RNA-seq or scRNAseq.

The ISG+ DC may be detected and/or measuring based on a differential and/or unique transcriptional profile. In some embodiments, the profile is positive for (or comprises or consists of positive expression of) H2-Ab1, Itgax, Flt3, Znfx1, Zbp1, Trim30c, Trafd1, Sp110, Slfn9, Samhd1, Rsad2, Rnf213, Pttg1, Phf11d, Phf11a, Parp14, Nmi, Iigp1, Igtp, Ifit3b, Ifih1, Ifi209, Gbp7, Gbp3, Fam26f, Endod1, Eif2ak2, Dhx58, Ddx60, Cmpk2, Cd86, Cd69, Ccl4, AA467197 and 1600014C10Rik. As used herein, a profile that is positive for a gene (also referred to herein as a marker) means that said gene (or marker) is expressed in the cell or cell population.

In some embodiments, the transcriptional profile is positive for (or comprises or consists of positive expression of) Trim30c, Cxcl10, Slfn9, Fam26f, Ifit1bl1, Cmpk2, Ifit3b, Endod1, Gbp7, Iigp1, Ifit2, Gbp3, Gbp2, Oasl1, Rsad2, Ifit1, Ms4a4b, Cd69, Ddx60, Igtp, Casp4, Ifi206, A530064D06Rik, Ddx58, Ifit3, Slfn4, 1600014C10Rik, Znfx1, Ifih1, Nt5c3, Slfn8, Trim30b, Slfn1, Mx1, B430306N03Rik, Herc6, Tgm2, Parp9, Ifi47, Axl, Tor3a, Dhx58, Fndc3a, Daxx, Phf11d, Lpxn, Isg20, Ifi211, Ifi213, Ifi44, Phf11a, Parp14, Usp18, Usp25, Ascc3, Fgl2, Ube2l6, Dck, Rtp4, Stat2, Ifi204, Irgm1, Pttg1, Eif2ak2, Rnf34, Rnf213, Hck, Aftph, Trafd1, Oasl2, Samd91, Xaf1, Ms4a6b, Zbp1, 2810474O19Rik, Nmi, Sppl2a, Cd86, Ifi207, Cdkn1a, Pnp, Lgals3 bp, Ccnd2, Ifi203, Slfn5, Hmox2, Wfdc17, Irf7, Ms4a4c, Ifi209, Trim30a, Phf11b, Ifi35, Tor1aip1, Chmp4b, Isg15, Sp100, Ms4a6c, Sp110, Mnda1, Slfn2, Samhd1, Selenow, Sat1, and Ifitm3.

In some embodiments, the transcriptional profile is positive for (or comprises or consists of positive expression of) Cxcl10, Ifit3 Rsad2/Viperin, Ifit1, Ifit1b11, Ifit2, Isg15, Ifit3b, Usp18, and Ifi204 expression.

The ISG+ DC may also be negative for Batf3 and IRF8 (Batf3– and IRF8–), at the mRNA and protein level.

In some embodiments, ISG+ DC are detected based on protein profile. In some embodiments, the protein profile includes XCR1, BDCA-3, and MHC Class II. In some embodiments, the ISG+ DC are XCR1−, BDCA-3−, and MHC Class II+, and they may be detected and/or measured based on this profile.

In some embodiments, the ISG+ DC are CD11c+, AXL+, DDX58+, DHX58+, IFIH1+, STING+ and TLR3−, TLR9− and they may be additionally detected and/or detected based on this profile.

In some embodiments, the protein profile is a cell surface protein profile. In some embodiments, the protein profile is obtained using flow cytometry. In some embodiments, the protein profile is obtained using CyTOF.

In some embodiments, the solid tumor sample is a melanoma sample, a skin/cutaneous melanoma sample. a cervical squamous cell carcinoma sample, an endocervical adenocarcinoma sample, a liver cancer sample, a hepatocellular carcinoma sample, or a sarcoma sample.

In some embodiments, the solid tumor sample is obtained by resection or biopsy.

In another aspect, this disclosure provides a method of treating a subject having a solid cancer, comprising administering, to a subject having a malignant tumor characterized as having neg/low ISG+ DC level, an ISG+ DC inducing agent in an effective amount.

In some embodiments, the method further comprises identifying the subject having a malignant tumor characterized as having neg/low ISG+ DC level.

In some embodiments, the malignant tumor is characterized as having neg/low ISG+ DC level using by measuring gene expression of H2-Ab1, Itgax, Flt3, Znfx1, Zbp1, Trim30c, Trafd1, Sp110, Slfn9, Samhd1, Rsad2, Rnf213, Pttg1, Phf11d, Phf11a, Parp14, Nmi, Iigp1, Igtp, Ifit3b, Ifih1, Ifi209, Gbp7, Gbp3, Fam26f, Endod1, Eif2ak2, Dhx58, Ddx60, Cmpk2, Cd86, Cd69, Ccl4, AA467197 and 1600014C10Rik.

In some embodiments, the malignant tumor is characterized as having neg/low ISG+ DC level using by measuring gene expression of Trim30c, Cxcl10, Slfn9, Fam26f, Ifit1b11, Cmpk2, Ifit3b, Endod1, Gbp7, Iigp1, Ifit2, Gbp3, Gbp2, Oasl1, Rsad2, Ifit1, Ms4a4b, Cd69, Ddx60, Igtp, Casp4, Ifi206, A530064D06Rik, Ddx58, Ifit3, Slfn4, 1600014C10Rik, Znfx1, Ifih1, Nt5c3, Slfn8, Trim30b, Slfn1, Mx1, B430306N03Rik, Herc6, Tgm2, Parp9, Ifi47, Axl, Tor3a, Dhx58, Fndc3a, Daxx, Phf11d, Lpxn, Isg20, Ifi211, Ifi213, Ifi44, Phf11a, Parp14, Usp18, Usp25, Ascc3, Fgl2, Ube2l6, Dck, Rtp4, Stat2, Ifi204, Irgm1, Pttg1, Eif2ak2, Rnf34, Rnf213, Hck, Aftph, Trafd1, Oasl2, Samd91, Xaf1, Ms4a6b, Zbp1, 2810474O19Rik, Nmi, Sppl2a, Cd86, Ifi207, Cdkn1a, Pnp, Lgals3 bp, Ccnd2, Ifi203, Slfn5, Hmox2, Wfdc17, Irf7, Ms4a4c, Ifi209, Trim30a, Phf11b, Ifi35, Tor1aip1, Chmp4b, Isg15, Sp100, Ms4a6c, Sp110, Mnda1, Slfn2, Samhd1, Selenow, Sat1, and Ifitm3.

In some embodiments, the malignant tumor is characterized as having neg/low ISG+ DC level using by measuring gene expression of Cxcl10, Ifit3 Rsad2/Viperin, Ifit1, Ifit1b11, Ifit2, Isg15, Ifit3b, Usp18, and Ifi204.

In some embodiments, the malignant tumor is characterized as having neg/low ISG+ DC level using by protein expression of one or more or all of XCR1, BDCA-3, and/or MHC Class II, wherein the ISG+ DC are XCR1−, BDCA-3−, and MHC Class II+.

In some embodiments, the ISG+ DC are CD11c+, AXL+, DDX58+, DHX58+, IFIH1+, STING+ and TLR3−, TLR9−.

In some embodiments, the ISG+ DC inducing agent is administered intratumorally.

In some embodiments, the ISG+ DC inducing agent is dsRNA or an analog thereof. In some embodiments, the ISG+ DC inducing agent is polyI:C or an analog thereof.

In some embodiments, the ISG+ DC inducing agent is a RIG-1 agonist.

In some embodiments, the ISG+ DC inducing agent is a MDA5 agonist.

In some embodiments, the ISG+ DC inducing agent is an MAVS pathway activator.

In some embodiments, the ISG+ DC inducing agent is an TLR3 agonist.

In some embodiments, the ISG+ DC inducing agent is an TLR7/8 agonist.

In some embodiments, the ISG+ DC inducing agent is an TLR9 agonist.

In some embodiments, the ISG+ DC inducing agent is type I interferon.

In some embodiments, a combination of two or more ISG+ DC inducing agents is administered to the subject.

In some embodiments, the method further comprises administering one or more secondary agents to the subject in an effective amount.

In some embodiments, the secondary agent is a checkpoint inhibitor. In some embodiments, the checkpoint inhibitor is a PD1/PDL1 inhibitor, a CTLA4 inhibitor, or a TIM3 inhibitor.

In some embodiments, the PD1/PDL1 inhibitor is an anti-PD1 or anti-PDL1 antibody or antigen-binding antibody fragment thereof In some embodiments, the CTLA4 inhibitor is an anti-CTLA4 antibody or antigen-binding antibody fragment thereof In some embodiments, the TIM3 inhibitor is an anti-TIM3 antibody or antigen-binding antibody fragment thereof In some embodiments, the secondary agent is a cGAS/STING agonist.

In some embodiments, the secondary agent is an antagonist of T cell co-stimulatory molecules.

In some embodiments, the one or more secondary agents are administered systemically or locally.

In some embodiments, the subject is human.

In some embodiments, the subject has not received an anti-cancer therapy.

In some embodiments, the subject has received an anti-cancer therapy.

In still another aspect, this disclosure provides a composition comprising an isolated cell population enriched for ISG+ DC, wherein ISG+ DC represent about 1% of the population.

In still another aspect, this disclosure provides a composition comprising isolated interferon-stimulated gene signature dendritic cells (ISG+ DC) coated with stabilized dsRNA.

In still another aspect, this disclosure provides a composition comprising isolated interferon-stimulated gene signature dendritic cells (ISG+ DC) coated with stabilized polyI:C.

In some embodiments of the foregoing compositions, the composition further comprises (a) tumor cells and/or (b) nanoparticles comprising peptide-MHC Class I complexes.

In some embodiments of the foregoing compositions, the peptide is or is derived from a tumor-specific antigen. In some embodiments of the foregoing compositions, the peptide is or is derived from a shared tumor antigen. In some embodiments of the foregoing compositions, the nanoparticle is a lipid vesicle.

In still another aspect, this disclosure provides composition comprising a nanoparticle comprising on its surface peptide-MHC Class I complexes, and dsRNA or an analog thereof. In some embodiments, the nanoparticle is a lipid vesicle capable of fusing with a cell.

In still another aspect, this disclosure provides a method for screening a cancer (e.g., tumor, tumor microenvironment (TME), etc.) sample for the presence of IFN (e.g., type I IFN), wherein the presence and/or level of IFN is used to inform a treatment regimen. The presence and/or level of IFN (e.g., type I IFN) in the sample may also be used as a surrogate for the presence and/or level of ISG+ DC in the sample. Subjects presenting with no or little tumor derived IFN may be treated, for example, with IFN (e.g., type I IFN) and/or dsRNA and/or a sting agonist. Subjects presenting with tumor derived IFN may be treated in another manner, including for example a potentially less aggressive manner, on the premise that the tumor may naturally regress partially or fully. For example, a "wait and see" approach of monitoring the subject and the tumor may be prescribed rather than a more aggressive regimen. The presence and/or level of IFN in a sample may be measured using protein or mRNA assays, including functional assays.

These and other aspects and embodiments of this disclosure will be described in greater detail herein.

BRIEF DESCRIPTION OF DRAWINGS

Non-limiting embodiments of the present invention will be described by way of example with reference to the accompanying Figures, which are schematic and are not intended to be drawn to scale. In the Figures:

FIG. 1A shows tumor outgrowth ($mm^2$) of MC38-SIY (circles) and MC57-SIY (squares) in wild-type (WT) C57BL/6 mice. Data are representative of two independent experiments with MC38-SIY n=3; MC57-SIY n=4 mice.

FIG. 1O shows tumor outgrowth ($mm^2$) of 1969-SIY in WT (black), Rag2−/− (dotted), and Batf3−/− (striped) mice. Data are representative of one independent experiment with WT n=2; Rag2−/− n=4, and Batf3−/− n=2 mice.

FIGS. 2A-2M show that functional assays and single-cell RNA-sequencing identify a novel DC subset characterized by a strong type-I-interferon gene signature.

FIG. 2A shows tumor outgrowth ($mm^2$) of MC57-SIY in WT (black squares) or STING−/− (striped squares) mice. Data are representative of three independent experiments with WT n=3; STING−/− n=3 mice.

FIG. 2B shows tumor outgrowth ($mm^2$) of MC57-SIY in WT (black squares) or Ifnar1−/− (striped squares) mice. Data are representative of two independent experiments with WT n=5; Ifnar1−/− n=2-5 mice.

FIG. 2C shows the percentage of T cell proliferation after 72 hour co-culture of naïve 2C TCR transgenic CD8+ T cells with tumor antigen-presenting cell compartments sorted from WT (black squares) and Batf3−/− (striped squares) mice bearing MC57-SIY tumors at day 5 post-tumor inoculation. Line indicates mean.

FIG. 2D shows the number of IFNγ-producing splenocytes from CD11c-depleted (DT-treated) or non-depleted (PBS-treated) CD11c-DTR bone marrow chimeric mice earing MC57-SIY tumors at day 5 following tumor inoculation. Data are pooled from individual mice (n=6) from two independent experiments.

FIG. 2E shows a t-SNE plot (top) of 6276 single-cell RNA-sequenced CD45+ cells from pooled MC57-SIY tumors at day 7 post-tumor inoculation in Rag2−/− mice (n=5) (top). Each dot represents a single cell. Flt3+ (blue dots), Itgax+ (red dots), and Flt3+ Itgax+ (purple dots) cells are highlighted and indicate DC clusters. FIG. 2E also shows a t-SNE plot (bottom) only of the 824 cells within the DC clusters.

FIG. 2F is a heatmap showing top 10 DEG for each of the DC clusters identified in FIG. 2E. DC cluster 0 top 10 DEG are: Ffar2, Cd72, H2-Eb1, H2-DMb2, Ltb, Ifngr1, Dab2, Il1r2, H2-Oa, Ifitm1. DC cluster 1 (ISG-DC+) top 10 DEG are: Cxcl10, Ifit3, Rsad2, Ifit1, Ifi204, Ifit2, Ifit1b11, Ifit3b, Isg15, Usp18. DC cluster 2 (DC2/moDC) top 10 DEG are: Cd209a, Ahnak, Vim, Emp3, S100a10, Ier2, Plec, Clec10a, Fos, Tppp3. DC cluster 3 (DC1) top 10 DEG are: Xcr1, Cd24a, Rab7b, Irf8, Naaa, Id2, Cst3, Ppt1, Stmn1, Hmgb2. DC cluster 4 (migratory DC) top 10 DEG are: Ccr7, Fscn1, Serpinb6b, Cd63, Serpinb9, Tbc1d4, Ccl22, Ramp3, Tmem123, Ccl5. DC cluster 5 (pDC_1) top 10 DEG are: Pi16, Cyp7b1, Lefty1, Cd7, Apod, Fcgrt, Itm2c, Cdkn2d, Tcf4, Cd209d. DC cluster 6 (pDC_2) top 10 DEG are: C1qc, C1qa, Ccl2, Ccl7, C1qb, Apoe, Pf4, Lyz2, Ccl6, Ccl12. DC cluster 7 top 10 DEG are: Iglc3, Ly6d, Gm21762, Klk1, Ccr9, Siglech, Cox6a2, Slpi, Cts1, Pltp.

FIG. 2G shows the average log fold change (avg_log FC) of Axl expression in each cluster compared to all other clusters combined. * indicates identification of Axl as a significant differentially expressed marker gene for the given cluster.

FIG. 2H shows representative flow cytometric analysis of AXL expression in the CD11c+ DC compartment in MC57-SIY tumors from $Rag2^{-/-}$ and $Batf3^{-/-}$ mice at day 11 and day 5 post-tumor inoculation, respectively. Data are representative of two independent experiments with $Rag2^{-/-}$ n=3-4; $Batf3^{-/-}$ n=2-3 mice.

FIG. 2I shows quantification of AXL expression as a percentage of CD11c+ cells in MC57-SIY tumors from $Rag2^{-/-}$ and $Batf3^{-/-}$ mice at day 11 and day 5 of tumor growth, respectively. Data are pooled from individual mice ($Rag2^{-/-}$ n=7; $Batf3^{-/-}$ n=5) from two independent experiments.

FIG. 2J shows tumor outgrowth (mm$^2$) of MC57-SIY in WT (black), CD11c-Cre x $Irf8^{fl/fl}$ (dotted), and CD11c-Cre x $Irf4^{fl/fl}$ (striped) mice. Data are representative of one independent experiment with WT n=3; CD11c-Cre x $Irf8^{fl/fl}$ n=4, and CD11c-Cre x $Irf4^{fl/fl}$ n=3 mice.

FIG. 2K shows a t-SNE plot (left) of 6276 scRNA-seq CD45+ cells from pooled MC57-SIY tumors at day 7 post-tumor implantation in $Rag2^{-/-}$ mice (n=5). Each dot represents a single cell. Clusters corresponding to dendritic cells, monocytes/macrophages, granulocytes, fibroblasts, and natural killer cells are indicated. FIG. 2K also shows t-SNE plots (right) highlighting select marker genes used to broadly identify cell clusters.

FIG. 2L shows representative flow cytometric gating strategy for Ly6C+ monocytes, F4/80+ macrophages, CD11c+ DC, CD103+ DC1, CD11b+ DC2, and ISG+ DC.

FIG. 2M shows the number of ISG+ DC in 50 mg of MC57-SIY (squares), 1969-SIY (triangles), and MC38-SIY (circles) tumors at day 11 following tumor implantation in $Rag2^{-/-}$ mice. Data are representative of two independent experiments with n=3-4 mice.

FIG. 3A shows the percentage of T cell proliferation of naïve 2C TCR transgenic CD8+ T cells co-cultured with ISG+ DC, CD103+ DC1, and CD11b+ DC2 for 72 hours (left). DC were sorted from $Rag2^{-/-}$ mice bearing MC57-SIY tumors at day 11 post-tumor inoculation. FIG. 3A also shows a representative example of T cell proliferation peaks following co-culture with DC (right).

FIG. 3B shows the number of IFNγ-producing splenocytes from WT or $Batf3^{-/-}$ (denoted as 'KO') mice implanted with MC57-SIY WT, $β2M^{-/-}$, or 4% PFA-fixed tumor cells at day 7 post-tumor inoculation. Data are pooled from individual mice (n=3-8) from three independent experiments.

FIG. 3C shows representative flow cytometric analysis of tumor-derived $H-2K^b$:SIIN expression on CD11c+ DC subsets in Balb/c mice bearing MC57-SIY tumors at day 5 post-tumor inoculation.

FIG. 3D shows quantification of $H-2K^b$:SIIN expression on CD11c+ DC subsets in Balb/c mice bearing MC57-SIIN-SIY (first squares in each doublet) or MC57-SIY (second squares in each doublet) tumors at day 5 following tumor implantation. Data are pooled from two independent experiments with n=3 mice.

FIG. 3E is an immunofluorescence image of $H-2K^b$:SIIN cross-dressed Balb/c-derived ISG+ DC following a 24 hour co-culture with MC57-SIIN-SIY tumor cells. The image is representative of two independent experiments.

FIG. 3F is a schematic of experimental design for systemic immunity study in FIG. 3G.

FIG. 3G shows tumor outgrowth (mm$^2$) of MC38-SIY in $Batf3^{-/-}$ mice that were pre-inoculated 6 days earlier with MC57-SIY (bottom plot, striped circles) or PBS (top plot, black circles) on the contralateral flank. Numbers in parentheses indicate the number of mice with complete reduction of tumor burden. Data are pooled from individual mice (PBS n=5; MC57-SIY n=7) from two independent experiments.

FIG. 3H shows the percentage of T cell proliferation of naïve 2C TCR transgenic CD8+ T cells co-cultured with ISG+ DC, CD103+ DC1, and CD11b+ DC2 for 72 hours (left). DC were sorted from $Rag2^{-/-}$ mice bearing 1969-SIY tumors at day 11 post-tumor inoculation.

FIG. 3H also shows a representative example of T cell proliferation peaks following co-culture with DC (right).

FIG. 3I shows the percentage of T cell proliferation of naïve 2C TCR transgenic CD8+ T cells co-cultured with ISG+ DC, CD103+ DC1, and CD11b+ DC2 for 72 hours (left). DC were sorted from $Rag2^{-/-}$ mice bearing MC38-SIY tumors at day 11 post-tumor inoculation.

FIG. 3I also shows a representative example of T cell proliferation peaks following co-culture with DC.

FIG. 3J shows tumor outgrowth (mm$^2$) of MHC class I-sufficient MC57-SIY ($β2M^{+/+}$, bottom curve, black squares) and MHC class I-deficient MC57-SIY ($β2M^{-/-}$, top curve, striped squares) in WT mice. Data are representative of two independent experiments with n=3 mice.

FIG. 3K shows orthogonal views of an immunofluorescence microscopy image of Balb/c-derived ISG+ DC harboring intracellular $H-2K^b$:SIIN+ vesicles following a 24 hour co-culture with MC57-SIIN-SIY tumor cells. The image is representative of two independent experiments.

FIG. 4A depicts violin plots showing expression distribution of selected pattern recognition receptors (PRRs) in the DC clusters. Each dot represents a single cell.

FIG. 4B shows expression level of selected type-I-IFN response genes in GM-CSF-differentiated BM-DCs from WT or $Mavs^{-/-}$ mice that were unstimulated or cultured for 24 hours with MC57 tumor-conditioned media. Data are pooled from two independent experiments.

FIG. 4C shows ELISpot quantification of IFNγ-producing splenocytes from WT or Batf3$^{-/-}$ (denoted as 'KO') mice implanted with Poly(I:C)-coated or uncoated MC38-SIY WT, β2M$^{-/-}$, or 4% PFA-fixed tumor cells day 7 post-tumor inoculation. Data are pooled from individual mice (n=3-11) from four independent experiments.

FIG. 4D shows TCGA pan-cancer distribution of ISG$^+$ DC signature expression correlation scores. Each dot represents a single patient sample and the horizontal grey line marks the median value of the scaled (0, 1 min-max normalization) ISG$^+$ DC signature score per cancer type. Red dots indicate samples with the highest standardized scores (top z-score 1), while blue dots indicate samples with the lowest scores (bottom z-score ≤−1). Overlap significance of samples that ranked highly for ISG$^+$ DC signature (red dots) with samples that ranked highly (z-score ≥1) for a 160-gene T cell-inflamed signature is indicated with *p<0.05, p<0.001, *p<0.0001, and ****p<10$^{-10}$ (Hypergeometric test; n.s.=not significant).

FIG. 4E shows ELISpot quantification of IFNγ-producing splenocytes from WT or Batf3−/− (denoted as 'KO') mice implanted with Poly(I:C)-coated or uncoated MC38-SIY WT, β2M−/−, or 4% PFA-fixed tumor cells at day 7 post-tumor inoculation. Data shown are pooled from four independent experiments (WT ntotal=11; Batf3−/− ntotal=10 mice per group except "4% PFA-fixed cells" group with ntotal=3 mice). *p<0.05, p<0.01, *p<0.001, ****p<0.0001, ns=not significant; MWU test. Unless stated otherwise, data are shown as mean±s.e.m.

FIG. 4F shows ELISpot quantification of IFNγ-producing splenocytes from WT or Batf3−/− (denoted as 'KO') mice implanted with PRR agonist-coated or uncoated MC38-SIY tumor cells at day 7 post-tumor inoculation. Data are pooled from three independent experiments (ntotal=9 mice per group). *p<0.05, p<0.01, *p<0.001, ****p<0.0001, ns=not significant; MWU test. Unless stated otherwise, data are shown as mean±s.e.m.

FIG. 4G is a diagram of the working model.

FIG. 4H illustrates expression level, shown as fold change over unstimulated, of selected type-I-IFN response genes in GM-CSF-differentiated WT BM-DCs that were cultured for 24 hours with MC57 or MC38 tumor-conditioned media. Data are pooled from two independent experiments.

FIG. 4I is an immunofluorescence image of a Balb/c-derived ISG$^+$ DC harboring H-2K$^b$:SIIN$^+$ vesicles and H-2K$^b$:SIIN$^+$ DAPI$^+$ vesicles following a 24 hour co-culture with MC57-SIIN-SIY tumor cells. The image is representative of two independent experiments.

FIG. 4J depicts Kaplan-Meier plots displaying five-year survival probability of CESC, LIHC, SARC, and SKCM patients in the TCGA cohort. Data are stratified by high (top z-score ≥1, top curve in each plot) or low (bottom z-score ≤−1, bottom curve in each plot) scores based on expression correlation with a 160-gene T cell-inflamed signature (top panels) or the ISG$^+$ DC signature (bottom panels).

Figure 1A:
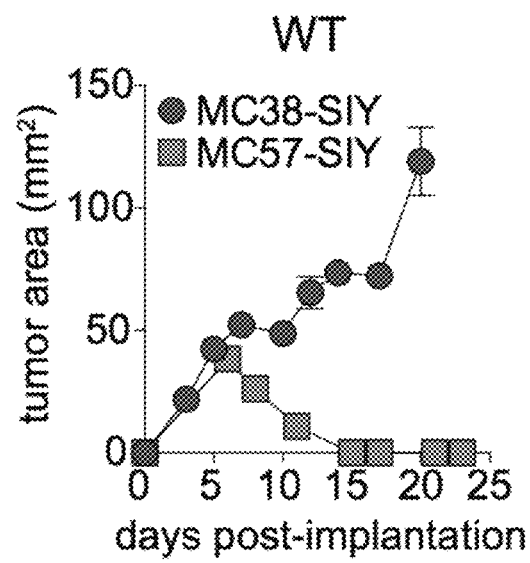
FIGS. 1A-1O show that regression of an immunogenic fibrosarcoma is independent of Batf3-driven, cross-presenting dendritic cells.

The color versions of the Figures are available in the file wrapper of the priority application 63/039,166 filed on Jun. 15, 2020, the entire contents of which are incorporated by reference herein.

DETAILED DESCRIPTION OF INVENTION

Productive T cell responses are required for tumor clearance, but factors promoting highly functional T cells within the tumor are poorly characterized. Tumor-resident antigen-presenting cells, such as dendritic cells (DC), have the capacity to shape anti-tumor T cell responses. By comparing DC subsets of spontaneously regressing tumors with those of progressing tumors, a novel stimulatory DC subset was identified, such subset characterized by an interferon-stimulated gene signature that was distinct from cross-presenting Batf3-driven DC1. This novel subset is referred to as ISG+ DC herein.

ISG+ DC are sensitized via engagement of cytosolic dsRNA receptors and they in turn activate CD8$^+$ T cells by cross-dressing with tumor-derived peptide-MHC complexes. Cross-dressing ISG+ DC can be induced by exogenous addition of a dsRNA analog to elicit protective systemic anti-tumor T cell responses. This novel subset of DC and its unique functional properties may be exploited in to enhance anti-tumor immunity.

Accordingly, this disclosure is based on the surprising discovery of a novel class of dendritic cells, the presence and/or activation of which in a tumor microenvironment correlates with tumor regression, particularly in response to secondary therapies such as but not limited to checkpoint inhibitor therapy. This novel class of dendritic cells, referred to herein as interferon-stimulated gene signature dendritic cells or ISG+ DCs, have unique mRNA and protein expression profiles that render them distinct from other DC subsets. These cells are also able to present tumor antigen in the context of MHC Class I in a manner that itself is distinct from conventional antigen cross-presentation (i.e., internalization and digestion of tumor cells, tumor cell debris and/or tumor antigens). Instead, these cells present tumor antigen in the context of MHC Class I in a manner referred to herein as "cross-dressing", a phenomenon that has not been heretofore described between DCs and non-immune cells such as tumor cells.

Accordingly, this disclosure provides, inter alia, compositions comprising ISG+ DC cells, methods of detecting such cells and measuring their levels in a subject or in a tissue (e.g., a tumor) with the subject, methods of enhancing activity and/or increasing number of such cells, and methods of identifying subjects that would benefit from enhancing activity and/or number of such cells, and methods of treating particular conditions (e.g., a cancer) by enhancing activity and/or number of such cells.

ISG+ DC

ISG+ DC, as their name implies, are a stimulatory class of dendritic cells (DCs). They are functionally defined as capable of producing type I-IFN and cross-dressing, meaning they are able to present pre-formed functional tumor peptide—MHC complexes derived from adjacent tumor cells. Such cross-dressing is believed to occur through a process of membrane exchange using cellular vesicles from tumor cells. Such ISG+ DC presenting tumor peptide-MHC complexes are then able to activate CD8$^+$ T cells in the tumor microenvironment, thereby inducing or contributing to an T cell inflamed phenotype. Cross-dressing is not dependent on internalization and digestion of tumor cells, tumor cell debris or tumor antigens in order to present the tumor antigen on the ISG+ DC surface.

ISG+ DC are also capable of sensing and responding to dsRNA such as dsRNA from tumor cells.

ISG+ DC may be characterized by their expression profiles, including gene and protein expression profiles. ISG+ DC may be characterized by an interferon-stimulated gene (ISG) signature, referring to a subset of genes that are differentially and, in some cases, uniquely expressed by ISG+ DC. This disclosure provides various ISG signatures including a 35-gene ISG-DC signature described herein that was used in the TCGA analysis, the extended (105 gene) ISG+ signature (see below), and those found in Tables 2 and 3, as provided herein.

ISG+ DC may also be defined as DC that do not express the transcription factors Batf3 and IRF8. Neither of these factors is required for cross-dressing as provided herein, although they may be required for cross-presentation and so would be expected to be transcribed in cross-presenting DC but not ISG+ DC.

The ISG+ DC may be defined and/or identified using a 35 gene signature consisting of H2-Ab1, Itgax, Flt3, Znfx1, Zbp1, Trim30c, Trafd1, Sp110, Slfn9, Samhd1, Rsad2, Rnf213, Pttg1, Phf11d, Phf11a, Parp14, Nmi, Iigp1, Igtp, Ifit3b, Ifih1, Ifi209, Gbp7, Gbp3, Fam26f, Endod1, Eif2ak2, Dhx58, Ddx60, Cmpk2, Cd86, Cd69, Ccl4, AA467197 and 1600014C10Rik. Another set of 105 markers that may be used to define and/or identify ISG+ DC comprises the following markers: Trim30c, Cxcl10, Slfn9, Fam26f, Ifit1b11, Cmpk2, Ifit3b, Endod1, Gbp7, Iigp1, Ifit2, Gbp3, Gbp2, Oasl1, Rsad2, Ifit1, Ms4a4b, Cd69, Ddx60, Igtp, Casp4, Ifi206, A530064D06Rik, Ddx58, Ifit3, Slfn4, 1600014C10Rik, Znfx1, Ifih1, Nt5c3, Slfn8, Trim30b, Slfn1, Mx1, B430306N03Rik, Herc6, Tgm2, Parp9, Ifi47, Axl, Tor3a, Dhx58, Fndc3a, Daxx, Phf11d, Lpxn, Isg20, Ifi211, Ifi213, Ifi44, Phf11a, Parp14, Usp18, Usp25, Ascc3, Fgl2, Ube2l6, Dck, Rtp4, Stat2, Ifi204, Irgm1, Pttg1, Eif2ak2, Rnf34, Rnf213, Hck, Aftph, Trafd1, Oasl2, Samd91, Xaf1, Ms4a6b, Zbp1, 2810474O19Rik, Nmi, Sppl2a, Cd86, Ifi207, Cdkn1a, Pnp, Lgals3 bp, Ccnd2, Ifi203, Slfn5, Hmox2, Wfdc17, Irf7, Ms4a4c, Ifi209, Trim30a, Phf11b, Ifi35, Tor1aip1, Chmp4b, Isg15, Sp100, Ms4a6c, Sp110, Mnda1, Slfn2, Samhd1, Selenow, Sat1, and Ifitm3.

Figure 2A:
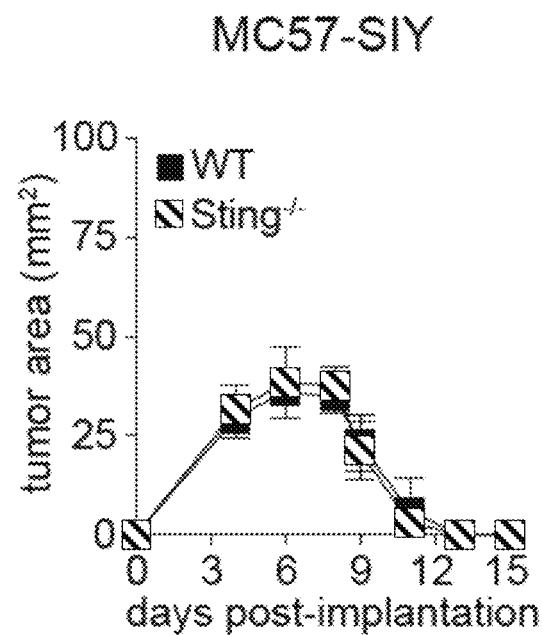
Figure 2B:
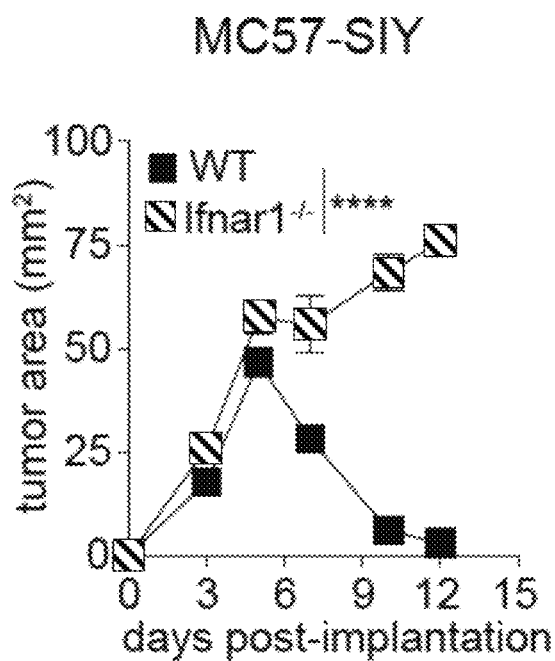
Figure 2C:
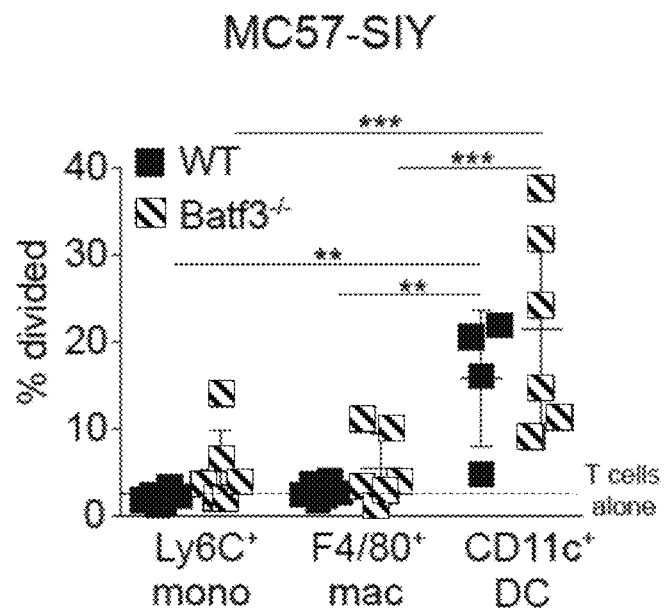
Figure 2D:
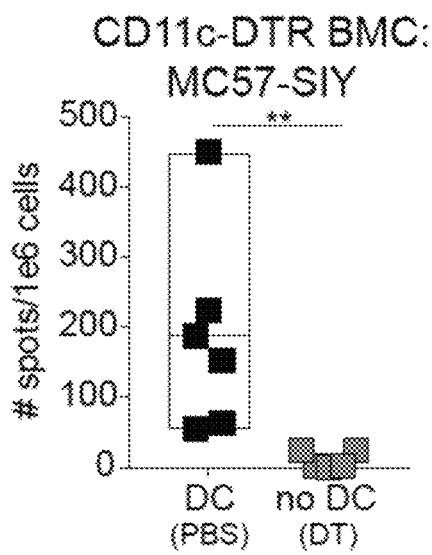
Figure 2E:
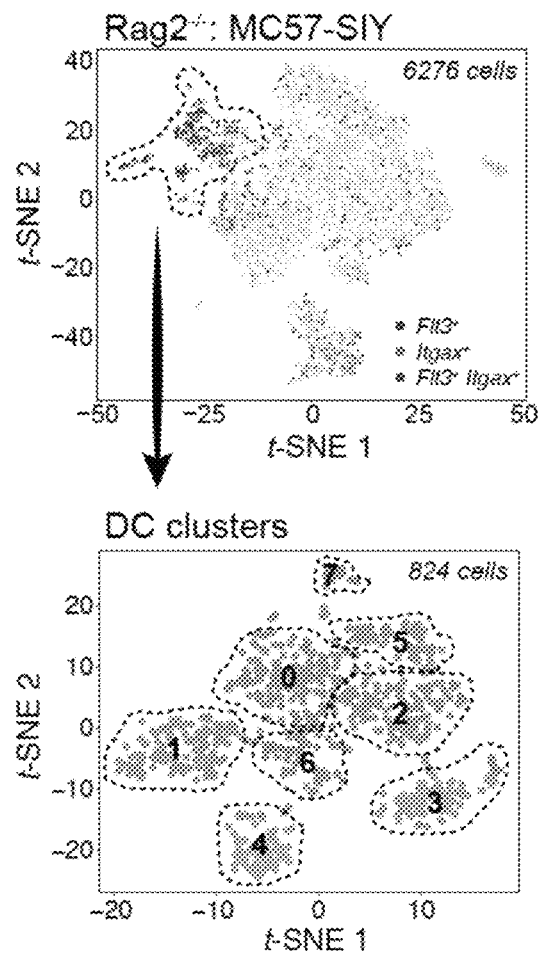
Figure 2F:
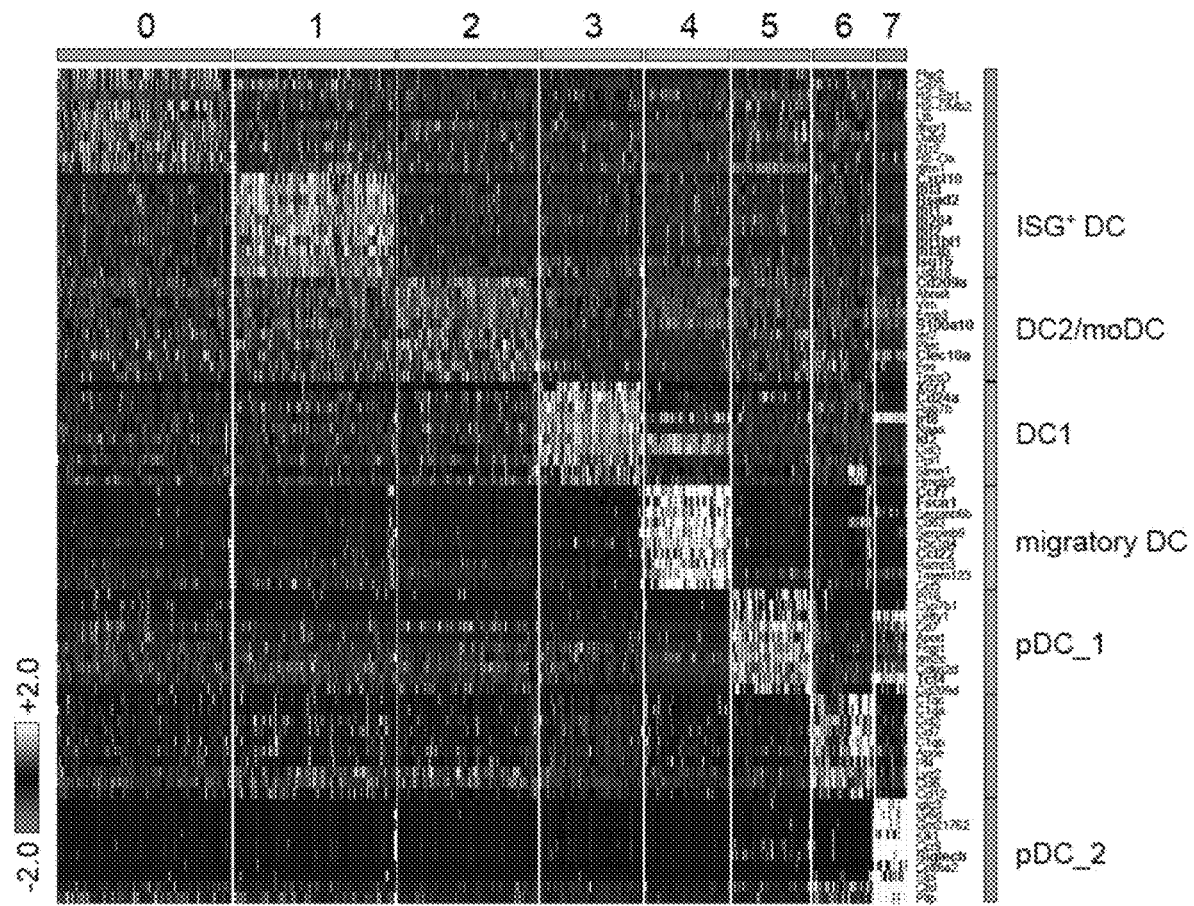

ISG+ DC lack significant transcriptional similarity to conventional DC subsets, including DC1, DC2/monocyte-derived DC (moDC), migratory DC, and pDCs, as shown in FIGS. 2E and 2F.

Table 3 provides a list of significant marker genes expressed differentially and uniquely in the ISG+ DC cluster (cluster 1) relative to the remaining 7 identified DC clusters, and annotation of their subcellular localization. These genes are referred to herein as differentially expressed genes (DEG). The Table ranks these genes according to an enrichment score that is expressed as the percent expression of the gene in the 7 non-ISG+ DC clusters analyzed herein over percent expression of the gene in the ISG+ DC cluster. The genes at the top of the list are positively and differentially expressed in the ISG+ DC cluster to a greater extent than those at the bottom of the list. The genes are rank ordered as follows: Trim30c, Cxcl10, Slfn9, Fam26f, Ifit1b11, Cmpk2, Ifit3b, Endod1, Gbp7, Iigp1, Ifit2, Gbp3, Gbp2, Oasl1, Rsad2, Ifit1, Ms4a4b, Cd69, Ddx60, Igtp, Casp4, Ifi206, A530064D06Rik, Ddx58, Ifit3, Slfn4, 1600014C10Rik, Znfx1, Ifih1, Nt5c3, Slfn8, Trim30b, Slfn1, Mx1, B430306N03Rik, Herc6, Tgm2, Parp9, Ifi47, Axl, Tor3a, Dhx58, Fndc3a, Daxx, Phf11d, Lpxn, Isg20, Ifi211, Ifi213, Ifi44, Phf11a, Parp14, Usp18, Usp25, Ascc3, Fgl2, Ube2l6, Dck, Rtp4, Stat2, Ifi204, Irgm1, Pttg1, Eif2ak2, Rnf34, Rnf213, Hck, Aftph, Trafd1, Oasl2, Samd91, Xaf1, Ms4a6b, Zbp1, 2810474O19Rik, Nmi, Sppl2a, Cd86, Ifi207, Cdkn1a, Pnp, Lgals3 bp, Ccnd2, Ifi203, Slfn5, Hmox2, Wfdc17, Irf7, Ms4a4c, Ifi209, Trim30a, Phf11b, Ifi35, Tor1aip1, Chmp4b, Isg15, Sp100, Ms4a6c, Sp110, Mnda1, Slfn2, Samhd1, Selenow, Sat1, and Ifitm3. Their enrichment scores range from 0.167 (top) to 0.939 (bottom). Some but not all of these genes are interferon-stimulated genes (ISG). This marker set, or a subset thereof, may be used as a gene signature for ISG+ DC.

ISG+ DC may also be defined and/or identified, based on subsets of these genes. For example, ISG+ DC may be defined and/or identified based on expression of genes having an enrichment score of less than or equal to 0.5. As shown in Table 3, these genes are Trim30c, Cxcl10, Slfn9, Fam26f, Ifit1b11, Cmpk2, Ifit3b, Endod1, Gbp7, Iigp1, Ifit2, Gbp3, Gbp2, Oasl1, Rsad2, Ifit1, Ms4a4b, Cd69, Ddx60, Igtp, Casp4, Ifi206, A530064D06Rik, Ddx58, Ifit3, Slfn4, 1600014C10Rik, Znfx1, Ifih1, Nt5c3, Slfn8, Trim30b, Slfn1, Mx1, B430306N03Rik, Herc6, Tgm2, Parp9, Ifi47, Axl, Tor3a, Dhx58, Fndc3a, Daxx, Phf11d, Lpxn and Isg20.

ISG+ DC may be defined and/or identified based on expression of genes having an enrichment score of less than or equal to 0.45, 0.40, 0.35, 0.30, 0.25, or 0.20. Genes falling into each of these subsets are provided in Table 3.

In other instances, the ISG+ DC may be characterized by the following DEGs: Cxcl10, Ifit3 Rsad2/Viperin, Ifit1, Ifit1b11, Ifit2, Isg15, Ifit3b, Usp18, and Ifi204, all of which are interferon-stimulated genes (ISG). These genes were identified as being DEGs for ISG+ DC as compared to other DC clusters by filtering on genes expressed in more than 25% of cells in the cluster and a minimum 0.5-fold difference in expression level between the ISG+ DC cluster and other DC clusters. As shown in Table 2, these genes have a minimum avg_log FC threshold of 1.3 using Seurat SubsetData function analysis (see Materials and Methods, herein).

Of these various gene markers, CD69 and AXL are cell membrane proteins. CD69 has an enrichment score of 0.350 and AXL has an enrichment score of 0.474. Cell surface expression of these markers may be used in addition to the various marker subsets described above to define and/or identify ISG+ DC. Axl is an IFN-inducible receptor tyrosine kinase, and its expression uniquely and significantly distinguishes ISG+ DC from other known DC subsets, as shown in FIG. 2G and Table 3.

ISG+ DC may be further characterized based on expression of Ddx58, Dhx58 and Ifih1, all of which are pattern recognition receptors (PRRs). ISG+ DC also express STING which is more broadly expressed in all DC clusters analyzed.

ISG+ DC are unique and distinct from other DC classes such as AS-DC described by Villani et al. Science, 356: 6335, 2017 and published PCT application WO2018/035364 which reportedly express Axl but are found in blood of healthy subjects.

ISG+ DC have been found exclusively in non-blood tissues, particularly in solid cancers or tumors and their corresponding microenvironments.

TABLE 1

Top 20 DEG for 16 clusters identified from scRNA-seq of the CD45+ immune infiltrate of regressor MC57-SIY tumors in Rag2−/− mice.

| cluster | gene | avg_logFC | p_val_adj |
|---|---|---|---|
| 0 | C1qa | 1.7827483 | 3.25E−214 |
| | Ms4a7 | 1.7128027 | 0 |
| | C1qb | 1.6409811 | 7.86E−202 |
| | C1qc | 1.5318735 | 1.23E−227 |
| | Lgmn | 1.2776955 | 0 |
| | Apoe | 1.2613257 | 3.30E−237 |
| | Cd72 | 1.0383933 | 2.42E−205 |
| | Ccl12 | 0.9730476 | 1.30E−191 |
| | Trem2 | 0.9707807 | 3.35E−262 |
| | Dab2 | 0.9526733 | 3.72E−247 |

TABLE 1-continued

Top 20 DEG for 16 clusters identified from scRNA-seq of the CD45+ immune infiltrate of regressor MC57-SIY tumors in Rag2−/− mice.

| cluster | gene | avg_logFC | p_val_adj |
|---|---|---|---|
|  | Ccl7 | 0.9502527 | 1.04E-183 |
|  | Cxcl16 | 0.902741 | 6.27E-252 |
|  | Aif1 | 0.8870459 | 7.68E-239 |
|  | Mrc1 | 0.8490206 | 2.39E-180 |
|  | Pf4 | 0.8334967 | 1.93E-246 |
|  | Ctsl | 0.8299461 | 2.05E-171 |
|  | Rnase4 | 0.829605 | 2.48E-227 |
|  | Fcgr2b | 0.8220888 | 2.74E-187 |
|  | Adgre1 | 0.811822 | 2.01E-192 |
|  | Ecm1 | 0.8086945 | 1.75E-195 |
| 1 | Ccl6 | 0.7526458 | 4.50E-103 |
|  | Vcan | 0.6983796 | 3.90E-81 |
|  | Ccl9 | 0.6565901 | 9.50E-92 |
|  | Fn1 | 0.5818291 | 1.02E-44 |
|  | S100a4 | 0.570185 | 1.61E-113 |
|  | Pid1 | 0.5696696 | 2.34E-103 |
|  | S100a10 | 0.527195 | 2.73E-83 |
|  | Ccr2 | 0.5036539 | 3.36E-88 |
|  | Clec4a2 | 0.5029837 | 5.58E-59 |
|  | Tgfbi | 0.4894501 | 1.89E-64 |
|  | Pkm | 0.4829249 | 1.11E-87 |
|  | Ahnak | 0.4802793 | 6.90E-55 |
|  | Anxa2 | 0.4795158 | 4.36E-65 |
|  | Crip1 | 0.4759648 | 9.92E-69 |
|  | C5ar1 | 0.4727068 | 4.18E-47 |
|  | Msr1 | 0.4620189 | 7.13E-56 |
|  | Chil3 | 0.4619573 | 2.43E-34 |
|  | Lyz2 | 0.4531941 | 1.94E-71 |
|  | Vim | 0.4469377 | 6.65E-55 |
|  | Hif1a | 0.4468832 | 4.41E-37 |
| 2 | Ifi204 | 0.7735724 | 6.24E-166 |
|  | Ifi209 | 0.7700601 | 4.18E-144 |
|  | Ifi211 | 0.7614971 | 7.32E-131 |
|  | Isg15 | 0.7554112 | 3.81E-160 |
|  | Chil3 | 0.7443973 | 1.34E-65 |
|  | Ifi47 | 0.7436558 | 1.46E-131 |
|  | Ifit1 | 0.7400161 | 5.77E-106 |
|  | Ifit3 | 0.7265544 | 2.32E-157 |
|  | Plac8 | 0.7026573 | 2.39E-114 |
|  | Slfn4 | 0.6982973 | 6.97E-95 |
|  | Slfn5 | 0.6906737 | 1.55E-127 |
|  | Vcan | 0.6812052 | 6.82E-72 |
|  | Ms4a6d | 0.6729934 | 6.55E-99 |
|  | Ly6c2 | 0.6607128 | 4.00E-85 |
|  | Ms4a4c | 0.660401 | 6.11E-115 |
|  | Ifi205 | 0.6522749 | 1.38E-113 |
|  | Ifi203 | 0.6472541 | 1.18E-109 |
|  | Ifi213 | 0.6409834 | 1.98E-99 |
|  | Fcgr1 | 0.6396519 | 1.36E-114 |
|  | Mndal | 0.6245722 | 2.01E-97 |
| 3 | H2-Ab1 | 2.292941 | 2.30E-291 |
|  | H2-Eb1 | 2.2846538 | 0 |
|  | H2-Aa | 2.2679913 | 0 |
|  | Cd209a | 2.1087589 | 0 |
|  | Ifitm1 | 2.0873382 | 7.70E-235 |
|  | Cd74 | 2.0122475 | 1.30E-244 |
|  | H2-DMb1 | 1.7137161 | 2.01E-299 |
|  | Klrd1 | 1.3855408 | 4.40E-267 |
|  | Ciita | 1.2703688 | 0 |
|  | H2-DMa | 1.1884669 | 1.22E-188 |
|  | Napsa | 1.1642674 | 3.77E-172 |
|  | Syngr2 | 1.0765111 | 1.90E-152 |
|  | Ckb | 0.9817773 | 9.54E-119 |
|  | Cbfa2t3 | 0.9528586 | 3.67E-247 |
|  | Ccnd1 | 0.9277466 | 7.89E-130 |
|  | Lsp1 | 0.7764612 | 3.12E-126 |
|  | Gpr171 | 0.7619331 | 4.30E-154 |
|  | Ccnd2 | 0.7615807 | 2.57E-71 |
|  | Gm2a | 0.7557925 | 5.52E-90 |
|  | Olfm1 | 0.7496458 | 1.54E-132 |
| 4 | Cxcl100 | 2.6767814 | 0 |
|  | Rsad2 | 2.211094 | 0 |
|  | Ifit1bl1 | 1.9266606 | 0 |
|  | Ifit3 | 1.8546206 | 2.07E-291 |
|  | Ccl4 | 1.8355127 | 1.08E-182 |
|  | Ifit2 | 1.7805039 | 0 |
|  | Ifit1 | 1.7502973 | 5.19E-274 |
|  | Cmpk2 | 1.6743157 | 0 |
|  | Ifit3b | 1.4936626 | 0 |
|  | Isg15 | 1.4394337 | 2.94E-232 |
|  | Ifi205 | 1.4027532 | 3.91E-230 |
|  | Ccl12 | 1.4023208 | 1.55E-99 |
|  | Gbp2 | 1.3169703 | 3.58E-199 |
|  | Usp18 | 1.2797858 | 1.52E-203 |
|  | Mx1 | 1.2754923 | 4.58E-210 |
|  | Oasl1 | 1.2574342 | 5.29E-214 |
|  | Fgl2 | 1.2324102 | 1.66E-183 |
|  | Slfn4 | 1.1360049 | 5.37E-154 |
|  | Phf11b | 1.1177666 | 3.46E-156 |
|  | Cd69 | 1.1142276 | 1.36E-163 |
| 5 | Mgst1 | 1.3491707 | 2.20E-208 |
|  | Hp | 1.2292916 | 9.18E-195 |
|  | Gngt2 | 1.2130015 | 1.27E-81 |
|  | Lyz2 | 1.1048023 | 2.64E-150 |
|  | Nr4a1 | 1.0882873 | 1.13E-130 |
|  | Smpdl3a | 1.0496294 | 5.44E-120 |
|  | Ifitm6 | 0.9920443 | 3.91E-126 |
|  | Msrb1 | 0.9786975 | 4.61E-152 |
|  | Chil3 | 0.9221313 | 2.83E-41 |
|  | Gm9733 | 0.8874743 | 1.02E-107 |
|  | Cybb | 0.8676914 | 1.35E-117 |
|  | Cd300a | 0.8567043 | 5.30E-104 |
|  | Ier2 | 0.8386535 | 1.78E-75 |
|  | Adgre5 | 0.8293568 | 1.93E-88 |
|  | Pou2f2 | 0.799531 | 1.14E-62 |
|  | Itgal | 0.7723968 | 1.79E-82 |
|  | Gsr | 0.7311544 | 3.10E-102 |
|  | Btg2 | 0.7268551 | 2.02E-38 |
|  | Cytip | 0.7195813 | 1.12E-83 |
|  | Nadk | 0.6716448 | 7.54E-58 |
| 6 | Gzma | 3.3521801 | 0 |
|  | Nkg7 | 3.1195917 | 0 |
|  | Gzmb | 2.9946207 | 0 |
|  | AW112010 | 2.7523008 | 0 |
|  | Ctla2a | 2.4435588 | 0 |
|  | Xcl1 | 2.4074022 | 0 |
|  | Ms4a4b | 2.3614188 | 0 |
|  | Ccl5 | 2.2328076 | 4.92E-268 |
|  | Gimap4 | 2.176829 | 0 |
|  | Ptprcap | 2.1362379 | 0 |
|  | Klra7 | 2.1257151 | 0 |
|  | Il2rb | 2.0771458 | 0 |
|  | Klre1 | 2.0680631 | 0 |
|  | Prf1 | 1.9983974 | 0 |
|  | Ctsw | 1.954803 | 0 |
|  | Klrb1c | 1.9052856 | 0 |
|  | Ncr1 | 1.8256775 | 0 |
|  | Klrd1 | 1.8020089 | 0 |
|  | Trbc1 | 1.7369401 | 0 |
|  | Gimap6 | 1.6956815 | 0 |
| 7 | Thbs1 | 1.5712841 | 4.40E-161 |
|  | Dmkn | 1.3979668 | 1.67E-188 |
|  | Cd14 | 1.3016386 | 6.91E-140 |
|  | Chil3 | 1.2108802 | 1.30E-98 |
|  | Vim | 0.9741006 | 5.26E-147 |
|  | Lyz2 | 0.9648533 | 4.89E-134 |
|  | Mmp19 | 0.9463119 | 6.83E-116 |
|  | Clec4e | 0.9345213 | 2.01E-130 |
|  | Smox | 0.930905 | 3.37E-112 |
|  | Vcan | 0.9256781 | 4.11E-129 |
|  | Cd44 | 0.9216152 | 1.66E-121 |
|  | Mgst1 | 0.8815192 | 5.05E-128 |
|  | Clec4d | 0.8704299 | 1.05E-106 |
|  | Hp | 0.86617 | 2.95E-117 |
|  | Actg1 | 0.8450354 | 1.59E-160 |
|  | Srgn | 0.841497 | 5.55E-137 |
|  | Ier3 | 0.8166592 | 1.52E-53 |
|  | Plaur | 0.7763359 | 1.15E-77 |

TABLE 1-continued

Top 20 DEG for 16 clusters identified from scRNA-seq of the CD45+ immune infiltrate of regressor MC57-SIY tumors in Rag2−/− mice.

| cluster | gene | avg_logFC | p_val_adj |
|---|---|---|---|
|  | Gda | 0.7579251 | 4.93E−92 |
|  | Ifitm6 | 0.7066204 | 2.05E−66 |
| 8 | Pf4 | 2.7038031 | 1.17E−159 |
|  | Hmox1 | 2.6488427 | 4.36E−161 |
|  | Mt1 | 2.0546891 | 6.15E−125 |
|  | Arg1 | 1.9683049 | 2.30E−105 |
|  | Prdx1 | 1.7209931 | 5.05E−67 |
|  | Fth1 | 1.6230885 | 1.13E−86 |
|  | Ctsl | 1.5935942 | 1.82E−107 |
|  | Ftl1 | 1.4725413 | 1.33E−93 |
|  | Cd36 | 1.4653664 | 1.09E−174 |
|  | Fabp5 | 1.3710695 | 1.36E−27 |
|  | Creg1 | 1.2512295 | 4.16E−60 |
|  | Blvrb | 1.2022514 | 3.46E−99 |
|  | Mrc1 | 1.1391003 | 2.63E−60 |
|  | Bnip3 | 1.1251804 | 6.69E−77 |
|  | Ctsd | 1.111074 | 3.50E−93 |
|  | Cd63 | 1.1086815 | 5.73E−91 |
|  | Ctsb | 1.0734412 | 2.33E−99 |
|  | Clec4n | 1.0306254 | 5.40E−32 |
|  | Ninj1 | 0.9993545 | 2.52E−80 |
|  | Slc48a1 | 0.9951225 | 5.68E−101 |
| 9 | Txk | 1.7320442 | 6.19E−172 |
|  | Gzma | 1.6793038 | 3.38E−154 |
|  | Ms4a4b | 1.6082792 | 2.46E−95 |
|  | Il2rb | 1.5938652 | 8.61E−217 |
|  | Klre1 | 1.53819 | 1.57E−163 |
|  | Nkg7 | 1.5337039 | 2.95E−188 |
|  | Gzmb | 1.4559493 | 5.38E−157 |
|  | AW112010 | 1.4297332 | 3.09E−82 |
|  | Ccl5 | 1.4013747 | 3.83E−59 |
|  | Trbc1 | 1.3830778 | 3.33E−144 |
|  | Gimap4 | 1.3574776 | 5.24E−161 |
|  | Ctla2a | 1.2747582 | 6.78E−131 |
|  | Klrk1 | 1.2480119 | 8.56E−58 |
|  | Ptprcap | 1.2412209 | 3.22E−143 |
|  | Prf1 | 1.2301935 | 2.20E−133 |
|  | Gimap3 | 1.2004804 | 7.32E−137 |
|  | Serpinb9 | 1.1444809 | 2.25E−86 |
|  | Lck | 1.1384479 | 5.54E−120 |
|  | Gimap6 | 1.133596 | 2.78E−115 |
|  | Klrb1c | 1.1123396 | 1.47E−114 |
| 10 | Naaa | 1.9498715 | 3.87E−56 |
|  | Cst3 | 1.918764 | 1.96E−43 |
|  | H2-Ab1 | 1.5960951 | 3.26E−49 |
|  | Cd24a | 1.5872654 | 2.11E−187 |
|  | Stmn1 | 1.5826093 | 2.21E−81 |
|  | H2-Eb1 | 1.5268223 | 4.73E−54 |
|  | Irf8 | 1.5059366 | 2.20E−31 |
|  | H2-Aa | 1.4972672 | 1.36E−44 |
|  | Cd74 | 1.3653794 | 6.20E−34 |
|  | Id2 | 1.3497209 | 8.11E−34 |
|  | Hmgb2 | 1.2115115 | 6.44E−16 |
|  | Ckb | 1.1526356 | 2.05E−45 |
|  | Xcr1 | 1.1031669 | 0 |
|  | Wdfy4 | 1.0706747 | 6.11E−85 |
|  | H2-DMb1 | 1.0647325 | 2.13E−41 |
|  | H2afz | 1.0323053 | 9.27E−33 |
|  | Plbd1 | 1.0055944 | 2.30E−26 |
|  | Batf3 | 1.0034243 | 3.08E−99 |
|  | Cldnd1 | 0.9952001 | 1.27E−25 |
|  | Sept3 | 0.9797424 | 0 |
| 11 | S100a8 | 6.1303878 | 0 |
|  | S100a9 | 5.9747534 | 0 |
|  | Cxcl2 | 3.7512157 | 2.92E−82 |
|  | G0s2 | 3.6701192 | 0 |
|  | Retnlg | 3.4188594 | 0 |
|  | Il1b | 2.9413251 | 3.20E−60 |
|  | Ptgs2 | 2.9151039 | 3.86E−174 |
|  | Slpi | 2.8998688 | 1.09E−62 |
|  | Il1r2 | 2.5374639 | 1.14E−91 |
|  | Hdc | 2.4472169 | 3.51E−103 |
|  | Ier3 | 2.3717467 | 6.56E−29 |
|  | Cxcr2 | 2.2652434 | 0 |

TABLE 1-continued

Top 20 DEG for 16 clusters identified from scRNA-seq of the CD45+ immune infiltrate of regressor MC57-SIY tumors in Rag2−/− mice.

| cluster | gene | avg_logFC | p_val_adj |
|---|---|---|---|
|  | Ifitm1 | 2.219175 | 1.43E−22 |
|  | Dusp1 | 2.1476422 | 1.70E−52 |
|  | Slc7a11 | 2.1335886 | 7.19E−82 |
|  | Csf3r | 2.071519 | 6.14E−84 |
|  | Cd9 | 2.0283941 | 2.13E−27 |
|  | Msrb1 | 1.8878929 | 1.91E−35 |
|  | Grina | 1.876833 | 1.09E−28 |
|  | Il1rn | 1.8571144 | 1.80E−17 |
| 12 | Ccr7 | 3.2258987 | 0 |
|  | Ccl5 | 2.7295943 | 6.49E−52 |
|  | Fscn1 | 2.5500352 | 0 |
|  | Ccl22 | 2.492224 | 0 |
|  | Tbc1d4 | 2.4711473 | 0 |
|  | Tmem123 | 2.3076795 | 1.07E−90 |
|  | Ramp3 | 2.2978628 | 5.75E−202 |
|  | Socs2 | 2.2345435 | 0 |
|  | Cacnb3 | 2.1370109 | 0 |
|  | Cst3 | 2.1088095 | 9.32E−45 |
|  | Traf1 | 2.0908789 | 2.11E−81 |
|  | Cd63 | 2.0542608 | 9.57E−61 |
|  | Serpinb6b | 2.0219616 | 1.19E−111 |
|  | Gadd45b | 2.0058467 | 6.84E−93 |
|  | Il4i1 | 1.9960243 | 0 |
|  | Serpinb9 | 1.9880588 | 1.54E−106 |
|  | Cd83 | 1.9854676 | 9.92E−130 |
|  | Samsn1 | 1.9152758 | 5.10E−61 |
|  | Relb | 1.874565 | 6.13E−196 |
|  | Syngr2 | 1.8736868 | 8.05E−48 |
| 13 | Crabp1 | 2.7171418 | 1.75E−144 |
|  | Mt2 | 2.4707015 | 1.32E−74 |
|  | Col3a1 | 2.3796619 | 0 |
|  | Serpinh1 | 2.3485238 | 0 |
|  | Cd63 | 2.2839514 | 1.46E−43 |
|  | Col1a2 | 2.0781612 | 0 |
|  | Pcolce | 2.0093716 | 0 |
|  | Cst6 | 1.9968488 | 0 |
|  | Prdx4 | 1.9947246 | 1.74E−21 |
|  | Wfdc2 | 1.8929552 | 0 |
|  | Rhox5 | 1.83172 | 0 |
|  | Cav1 | 1.7759647 | 0 |
|  | Pebp1 | 1.6586347 | 3.32E−21 |
|  | Igfbp4 | 1.6229877 | 2.08E−146 |
|  | Gm10036 | 1.5980483 | 5.91E−40 |
|  | Cald1 | 1.597427 | 0 |
|  | Col6a1 | 1.5873703 | 0 |
|  | Rpl38 | 1.5771197 | 2.96E−21 |
|  | Rps2 | 1.54068 | 2.77E−16 |
|  | Tpm1 | 1.5021766 | 1.17E−51 |
| 14 | Siglech | 2.9602517 | 0 |
|  | Ly6d | 2.9263601 | 0 |
|  | Ccr9 | 2.6682657 | 0 |
|  | Klk1 | 2.5349007 | 0 |
|  | Iglc3 | 2.520546 | 0 |
|  | Gm21762 | 2.3221474 | 0 |
|  | Cox6a2 | 2.3020238 | 8.13E−272 |
|  | Irf8 | 2.2891128 | 8.30E−21 |
|  | Rnase6 | 2.204766 | 9.04E−19 |
|  | Pltp | 2.1596356 | 7.15E−31 |
|  | Tcf4 | 2.1248139 | 1.79E−23 |
|  | Lag3 | 2.0870977 | 7.22E−158 |
|  | Rpgrip1 | 1.9912552 | 1.73E−46 |
|  | Cd8b1 | 1.9512815 | 0 |
|  | Runx2 | 1.9399723 | 4.43E−92 |
|  | Bcl11a | 1.8645223 | 6.90E−92 |
|  | Dnajc7 | 1.8487397 | 1.21E−16 |
|  | Gm30211 | 1.8171636 | 0 |
|  | Jaml | 1.7765411 | 1.70E−39 |
|  | Igkc | 1.7669278 | 0 |
| 15 | Stmn1 | 2.5642298 | 1.43E−82 |
|  | Pclaf | 2.5176428 | 1.53E−133 |
|  | Hmgb2 | 2.4152425 | 2.30E−18 |
|  | Xcl1 | 2.3620718 | 4.56E−39 |
|  | Gzma | 2.1539635 | 5.78E−31 |
|  | Top2a | 1.9215044 | 3.75E−122 |

TABLE 1-continued

Top 20 DEG for 16 clusters identified from scRNA-seq of the CD45+ immune infiltrate of regressor MC57-SIY tumors in Rag2−/− mice.

| cluster | gene | avg_logFC | p_val_adj |
|---|---|---|---|
| | Gzmb | 1.8875891 | 2.93E−37 |
| | Tubb5 | 1.856707 | 1.98E−15 |
| | Nkg7 | 1.8117789 | 2.62E−36 |
| | Prf1 | 1.6638082 | 9.86E−53 |
| | Mki67 | 1.645791 | 1.76E−154 |
| | Ptprcap | 1.6404656 | 3.43E−36 |
| | Birc5 | 1.6381665 | 3.63E−105 |
| | Klre1 | 1.5744663 | 9.10E−41 |
| | Cks1b | 1.5384957 | 1.14E−51 |
| | Dut | 1.5139114 | 1.60E−77 |
| | Car2 | 1.4966708 | 1.72E−52 |
| | Thy1 | 1.4884176 | 5.89E−55 |
| | AW112010 | 1.4631815 | 1.15E−12 |
| | Cenpa | 1.3976726 | 2.32E−20 |

TABLE 2

Top 10 DEG for the eight DC clusters subsetted from scRNA-seq of the CD45+ immune infiltrate of regressor MC57-SIY tumors in Rag2−/− mice.

| cluster | DC subset | gene | avg_logFC | p_val_adj |
|---|---|---|---|---|
| 0 | Cluster 0 | H2-DMb2 | 1.0277875 | 8.01E−25 |
| | | Ffar2 | 0.9867109 | 4.03E−37 |
| | | Cd72 | 0.9862125 | 6.65E−31 |
| | | Il1r2 | 0.8963569 | 6.68E−17 |
| | | Dab2 | 0.8512954 | 7.84E−21 |
| | | Ltb | 0.841076 | 5.14E−23 |
| | | Ifitm1 | 0.8093051 | 6.10E−07 |
| | | H2-Oa | 0.8019474 | 1.56E−14 |
| | | Ifngr1 | 0.7836985 | 6.46E−23 |
| | | H2-Eb1 | 0.7645667 | 1.10E−29 |
| 1 | ISG+ DC | Cxcl10 | 2.6660829 | 5.01E−66 |
| | | Ifit3 | 1.9187944 | 3.56E−59 |
| | | Rsad2 | 1.7728777 | 1.09E−56 |
| | | Ifit1bl1 | 1.7476784 | 4.59E−57 |
| | | Ifit1bl1 | 1.5316667 | 1.46E−49 |
| | | Ifit2 | 1.4499578 | 1.57E−51 |
| | | Isg15 | 1.436346 | 3.37E−48 |
| | | Ifit3b | 1.3644485 | 1.28E−49 |
| | | Usp18 | 1.3536117 | 1.17E−43 |
| | | Ifi204 | 1.3434437 | 6.16E−56 |
| 2 | DC2/moDC | Cd209a | 1.0830578 | 5.81E−24 |
| | | Vim | 0.847628 | 1.25E−20 |
| | | Ahnak | 0.7785227 | 2.20E−22 |
| | | Clec10a | 0.6787764 | 1.07E−06 |
| | | Fos | 0.6765369 | 0.1756774 |
| | | Ier2 | 0.6645905 | 4.26E−09 |
| | | Plec | 0.6618258 | 1.85E−08 |
| | | S100a10 | 0.6323881 | 3.23E−14 |

TABLE 2-continued

Top 10 DEG for the eight DC clusters subsetted from scRNA-seq of the CD45+ immune infiltrate of regressor MC57-SIY tumors in Rag2−/− mice.

| cluster | DC subset | gene | avg_logFC | p_val_adj |
|---|---|---|---|---|
| | | Emp3 | 0.6322872 | 4.26E−18 |
| | | Nr4a1 | 0.6208068 | 0.3797349 |
| 3 | DC1 | Naaa | 1.8827541 | 4.12E−41 |
| | | Cd24a | 1.5037106 | 1.77E−51 |
| | | Irf8 | 1.4750945 | 1.42E−41 |
| | | Id2 | 1.4328144 | 9.46E−37 |
| | | Cst3 | 1.3017342 | 4.04E−35 |
| | | Ppt1 | 1.2333197 | 1.69E−28 |
| | | Xcr1 | 1.161159 | 1.08E−75 |
| | | Rab7b | 1.1585658 | 2.99E−43 |
| | | Wdfy4 | 1.0541174 | 1.36E−28 |
| | | Psap | 0.9974196 | 1.55E−28 |
| 4 | migratory DC | Ccl5 | 3.685416 | 1.44E−42 |
| | | Ccr7 | 3.0021025 | 8.69E−112 |
| | | Cd63 | 2.7199006 | 1.41E−81 |
| | | Fscn1 | 2.6750827 | 2.53E−103 |
| | | Serpinb6b | 2.4298285 | 3.23E−102 |
| | | Ccl22 | 2.3828883 | 3.80E−76 |
| | | Ramp3 | 2.3376415 | 4.93E−63 |
| | | Serpinb9 | 2.3373732 | 9.16E−80 |
| | | Tmem123 | 2.2216801 | 7.61E−45 |
| | | Tbc1d4 | 2.2046663 | 9.52E−77 |
| 5 | pDC_1 | Cd7 | 1.6568913 | 4.52E−32 |
| | | Pi16 | 1.4682399 | 3.16E−58 |
| | | Fcgrt | 1.457142 | 1.96E−23 |
| | | Cd209d | 1.4453212 | 3.86E−12 |
| | | Apod | 1.3965263 | 9.10E−28 |
| | | Cyp7b1 | 1.3952819 | 8.95E−45 |
| | | Tcf4 | 1.2805581 | 3.30E−19 |
| | | Itm2c | 1.2011164 | 3.29E−22 |
| | | Lefty1 | 1.0047811 | 8.09E−38 |
| | | Cdkn2d | 0.9879321 | 8.57E−20 |
| 6 | Cluster 6 | C1qb | 2.3582104 | 3.57E−25 |
| | | C1qa | 2.3125427 | 1.25E−28 |
| | | Apoe | 2.2411524 | 2.20E−24 |
| | | C1qc | 1.9729959 | 1.69E−33 |
| | | Ccl7 | 1.8244365 | 1.89E−27 |
| | | Pf4 | 1.8206523 | 1.00E−14 |
| | | Ccl2 | 1.7623787 | 1.83E−30 |
| | | Ccl6 | 1.6116814 | 4.58E−15 |
| | | Lyz2 | 1.5520665 | 1.62E−16 |
| | | Ccl12 | 1.4441865 | 3.35E−15 |
| 7 | pDC_2 | Ly6d | 2.8621421 | 1.80E−132 |
| | | Siglech | 2.8343572 | 1.99E−90 |
| | | Ctsl | 2.6971385 | 1.22E−32 |
| | | Iglc3 | 2.607889 | 2.74E−152 |
| | | Klk1 | 2.5294624 | 1.32E−108 |
| | | Ccr9 | 2.4851419 | 2.10E−97 |
| | | Slpi | 2.3908673 | 4.97E−57 |
| | | Cox6a2 | 2.3780332 | 5.75E−81 |
| | | Gm21762 | 2.3252388 | 2.38E−130 |
| | | Pltp | 2.0999402 | 9.12E−23 |

*bolded text indicates overlap with literature-reported markers for a given DC subset

TABLE 3

Unique, significant, and positive marker genes in the ISG+ DC cluster (cluster 1) and annotation of their subcellular localization.

| gene | avg_logFC | pct.1 (% expression in ISG+ DC cluster) | pct.2 (% expression in all other clusters) | enrichment score (pct.2/pct.1 ratio) | p_val_adj | subcellular location |
|---|---|---|---|---|---|---|
| Trim30c | 0.63840881 | 0.395 | 0.066 | 0.167 | 5.92E−26 | nucleus |
| Cxcl10 | 2.66608288 | 0.758 | 0.13 | 0.172 | 5.01E−66 | secreted |
| Slfn9 | 0.59820062 | 0.401 | 0.072 | 0.180 | 1.93E−24 | cytoplasm, nucleus |
| Fam26f | 0.77265141 | 0.446 | 0.081 | 0.182 | 1.69E−28 | n/a |
| Ifit1bl1 | 1.53166672 | 0.694 | 0.144 | 0.207 | 1.46E−49 | cytoplasm, nucleus |
| Cmpk2 | 1.11574964 | 0.624 | 0.138 | 0.221 | 9.28E−42 | cytoplasm, mitochondria |

TABLE 3-continued

Unique, significant, and positive marker genes in the ISG+ DC cluster (cluster 1) and annotation of their subcellular localization.

| gene | avg_logFC | pct.1 (% expression in ISG+ DC cluster) | pct.2 (% expression in all other clusters) | enrichment score (pct.2/pct.1 ratio) | p_val_adj | subcellular location |
|---|---|---|---|---|---|---|
| Ifit3b | 1.36444847 | 0.694 | 0.157 | 0.226 | 1.28E-49 | cytosol/nucleus |
| Endod1 | 0.64119395 | 0.427 | 0.097 | 0.227 | 8.14E-22 | n/a |
| Gbp7 | 0.90481167 | 0.675 | 0.178 | 0.264 | 6.58E-39 | cytoplasm, nucleus |
| Iigp1 | 0.8345871 | 0.261 | 0.073 | 0.280 | 3.26E-08 | cytosplasm, endoplasmic reticulum |
| Ifit2 | 1.4499578 | 0.809 | 0.241 | 0.298 | 1.57E-51 | cytoplasm, endoplasmic reticulum |
| Gbp3 | 0.70374315 | 0.439 | 0.136 | 0.310 | 6.03E-17 | cytoplasmic vesicle |
| Gbp2 | 1.08338024 | 0.586 | 0.184 | 0.314 | 1.72E-25 | cytoplasmic vesicle |
| Oasl1 | 0.97248342 | 0.669 | 0.219 | 0.327 | 7.96E-31 | cytoplasm, nucleus |
| Rsad2 | 1.77287766 | 0.873 | 0.288 | 0.330 | 1.09E-56 | endoplasmic reticulum, mitochondria |
| Ifit1 | 1.74767845 | 0.866 | 0.295 | 0.341 | 4.59E-57 | cytoplasm |
| Ms4a4b | 0.62141078 | 0.599 | 0.207 | 0.346 | 3.44E-22 | n/a |
| Cd69 | 0.70039806 | 0.363 | 0.127 | 0.350 | 1.09E-09 | plasma membrane |
| Ddx60 | 0.66975202 | 0.522 | 0.184 | 0.352 | 8.81E-17 | cytoplasm |
| Igtp | 0.75182288 | 0.669 | 0.237 | 0.354 | 2.88E-28 | n/a |
| Casp4 | 0.56457568 | 0.414 | 0.15 | 0.362 | 4.93E-11 | cytoplasm, endoplasmic reticulum |
| Ifi206 | 0.89688317 | 0.675 | 0.247 | 0.366 | 8.88E-29 | n/a |
| A530064D06Rik | 0.52853655 | 0.465 | 0.174 | 0.374 | 6.98E-13 | n/a |
| Ddx58 | 0.80920097 | 0.72 | 0.283 | 0.393 | 1.33E-28 | cytoplasm |
| Ifit3 | 1.9187944 | 0.904 | 0.376 | 0.416 | 3.56E-59 | cytoplasm, mitochondria |
| Slfn4 | 0.85198846 | 0.376 | 0.157 | 0.418 | 6.67E-07 | cytoplasm |
| 1600014C10Rik | 0.76482671 | 0.592 | 0.25 | 0.422 | 1.33E-18 | endoplasmic reticulum, mitochondria |
| Znfx1 | 0.61462596 | 0.586 | 0.252 | 0.430 | 3.34E-15 | n/a |
| Ifih1 | 1.03476048 | 0.79 | 0.34 | 0.430 | 5.16E-33 | cytosol |
| Nt5c3 | 0.87045564 | 0.662 | 0.288 | 0.435 | 1.45E-22 | cytoplasm, endoplasmic reticulum |
| Slfn8 | 0.87701852 | 0.707 | 0.31 | 0.438 | 7.19E-26 | nucleus |
| Trim30b | 0.59903162 | 0.561 | 0.246 | 0.439 | 1.77E-13 | n/a |
| Slfn1 | 0.99058227 | 0.79 | 0.348 | 0.441 | 2.24E-30 | n/a |
| Mx1 | 0.99191158 | 0.815 | 0.363 | 0.445 | 1.66E-31 | nucleus |
| B430306N03Rik | 0.53553825 | 0.51 | 0.228 | 0.447 | 4.07E-10 | n/a |
| Herc6 | 0.89257474 | 0.72 | 0.322 | 0.447 | 9.79E-25 | cytoplasm, nucleus |
| Tgm2 | 0.54417639 | 0.471 | 0.217 | 0.461 | 5.41E-07 | secreted |
| Parp9 | 0.5407171 | 0.561 | 0.259 | 0.462 | 7.89E-13 | cytoplasm, nucleus |
| Ifi47 | 1.20647357 | 0.879 | 0.415 | 0.472 | 1.32E-43 | endoplasmic reticulum |
| Axl | 0.55295783 | 0.439 | 0.208 | 0.474 | 2.11E-06 | plasma membrane |
| Tor3a | 0.82349939 | 0.79 | 0.375 | 0.475 | 2.76E-29 | endoplasmic reticulum |
| Dhx58 | 0.61635778 | 0.618 | 0.294 | 0.476 | 9.06E-15 | cytoplasm |
| Fndc3a | 0.56145457 | 0.599 | 0.286 | 0.477 | 5.74E-14 | cytoplasmic vesicle |
| Daxx | 0.80266141 | 0.739 | 0.36 | 0.487 | 6.89E-25 | cytoplasm, nucleus |
| Phf11d | 1.16950345 | 0.796 | 0.391 | 0.491 | 2.58E-32 | nucleus |
| Lpxn | 0.53003349 | 0.561 | 0.28 | 0.499 | 2.03E-11 | podosome |
| Isg20 | 1.17329337 | 0.828 | 0.414 | 0.500 | 3.26E-35 | nucleus, cytoplasm |
| Ifi211 | 1.02852415 | 0.841 | 0.424 | 0.504 | 5.74E-34 | nucleus, cytoplasm |
| Ifi213 | 1.00047687 | 0.86 | 0.438 | 0.509 | 4.62E-35 | n/a |
| Ifi44 | 0.6677373 | 0.529 | 0.27 | 0.510 | 1.71E-09 | cytoplasm |
| Phf11a | 0.82653012 | 0.783 | 0.418 | 0.534 | 2.68E-23 | nucleus |
| Parp14 | 0.86221037 | 0.815 | 0.438 | 0.537 | 4.30E-22 | cytoplasm, nucleus |
| Usp18 | 1.35361173 | 0.892 | 0.481 | 0.539 | 1.17E-43 | cytoplasm, nucleus |
| Usp25 | 0.5799601 | 0.662 | 0.357 | 0.539 | 4.25E-13 | cytoplasm, endoplasmic reticulum |
| Ascc3 | 0.5816161 | 0.58 | 0.315 | 0.543 | 4.21E-09 | cytoplasm, nucleus |
| Fgl2 | 1.13933634 | 0.86 | 0.469 | 0.545 | 6.49E-32 | secreted |
| Ube2l6 | 0.6969352 | 0.783 | 0.429 | 0.548 | 1.20E-20 | n/a |
| Dck | 0.63011498 | 0.739 | 0.405 | 0.548 | 9.84E-19 | cytoplasm, nucleus |
| Rtp4 | 1.0563531 | 0.911 | 0.507 | 0.557 | 3.47E-41 | cytoplasm |
| Stat2 | 0.6790359 | 0.79 | 0.444 | 0.562 | 4.54E-18 | cytoplasm, nucleus |
| Ifi204 | 1.34344365 | 0.955 | 0.538 | 0.563 | 6.16E-56 | cytoplasm, nucleus |
| Irgm1 | 0.74494496 | 0.777 | 0.441 | 0.568 | 5.68E-19 | lysosome, phagocytic vesicle |
| Pttg1 | 0.61386903 | 0.682 | 0.388 | 0.569 | 7.80E-14 | cytoplasm, nucleus |
| Eif2ak2 | 0.61675007 | 0.605 | 0.345 | 0.570 | 1.31E-09 | cytoplasm |
| Rnf34 | 0.5714857 | 0.586 | 0.337 | 0.575 | 3.55E-09 | cytoplasm, nucleus |
| Rnf213 | 0.63332771 | 0.758 | 0.438 | 0.578 | 2.26E-16 | cytoplasm |
| Hck | 0.61704772 | 0.796 | 0.466 | 0.585 | 1.71E-15 | lysosome |
| Aftph | 0.54493195 | 0.631 | 0.37 | 0.586 | 2.47E-09 | cytoplasm, nucleus |
| Trafd1 | 0.68946689 | 0.771 | 0.457 | 0.593 | 1.19E-19 | n/a |
| Oasl2 | 0.78438431 | 0.911 | 0.54 | 0.593 | 3.25E-30 | cytoplasm, nucleus |

TABLE 3-continued

Unique, significant, and positive marker genes in the ISG+ DC cluster (cluster 1) and annotation of their subcellular localization.

| gene | avg_logFC | pct.1 (% expression in ISG+ DC cluster) | pct.2 (% expression in all other clusters) | enrichment score (pct.2/pct.1 ratio) | p_val_adj | subcellular location |
|---|---|---|---|---|---|---|
| Samd9l | 0.87484563 | 0.86 | 0.517 | 0.601 | 9.03E−27 | endosome |
| Xaf1 | 0.84898177 | 0.904 | 0.555 | 0.614 | 3.13E−33 | nucleus, mitochondria |
| Ms4a6b | 1.02818089 | 0.949 | 0.598 | 0.630 | 8.18E−41 | plasma membrane |
| Zbp1 | 1.08274508 | 0.904 | 0.591 | 0.654 | 1.01E−35 | cytoplasm, nucleus |
| 2810474O19Rik | 0.52668385 | 0.656 | 0.429 | 0.654 | 7.83E−07 | nucleus |
| Nmi | 0.58937436 | 0.707 | 0.466 | 0.659 | 9.20E−10 | cytoplasm |
| Sppl2a | 0.5371044 | 0.688 | 0.472 | 0.686 | 6.74E−07 | endosome, lysosome |
| Cd86 | 0.65813341 | 0.65 | 0.448 | 0.689 | 2.90E−06 | plasma membrane |
| Ifi207 | 0.7382636 | 0.885 | 0.613 | 0.693 | 1.81E−22 | n/a |
| Cdkn1a | 0.50417096 | 0.707 | 0.495 | 0.700 | 6.53E−05 | cytoplasm, cytosol nucleus |
| Pnp | 0.88094807 | 0.892 | 0.631 | 0.707 | 7.69E−29 | cytoplasm, nucleus |
| Lgals3bp | 0.55566591 | 0.758 | 0.537 | 0.708 | 7.35E−12 | n/a |
| Ccnd2 | 0.81616034 | 0.898 | 0.643 | 0.716 | 2.15E−20 | cytoplasm, nucleus |
| Ifi203 | 1.05113987 | 0.968 | 0.702 | 0.725 | 1.85E−37 | cytoplasm, nucleus |
| Slfn5 | 1.0676689 | 0.981 | 0.724 | 0.738 | 1.86E−45 | nucleus |
| Hmox2 | 0.56929035 | 0.777 | 0.576 | 0.741 | 2.19E−12 | endoplasmic reticulum |
| Wfdc17 | 0.61821661 | 0.924 | 0.694 | 0.751 | 1.26E−12 | n/a |
| Irf7 | 1.04776945 | 0.975 | 0.733 | 0.752 | 2.74E−33 | cytoplasm, nucleus |
| Ms4a4c | 1.15157617 | 0.962 | 0.735 | 0.764 | 1.19E−45 | n/a |
| Ifi209 | 0.94339101 | 0.93 | 0.715 | 0.769 | 4.91E−33 | cytoplasm, nucleus |
| Trim30a | 0.68744399 | 0.962 | 0.745 | 0.774 | 6.87E−24 | cytoplasm, nucleus |
| Phf11b | 1.01542558 | 0.911 | 0.709 | 0.778 | 3.66E−31 | n/a |
| Ifi35 | 0.53877912 | 0.86 | 0.676 | 0.786 | 8.01E−14 | nucleus |
| Tor1aip1 | 0.56060254 | 0.873 | 0.687 | 0.787 | 4.88E−15 | nucleus |
| Chmp4b | 0.6017866 | 0.828 | 0.652 | 0.787 | 2.34E−14 | cytoplasm, endosome |
| Isg15 | 1.43634598 | 0.949 | 0.748 | 0.788 | 3.37E−48 | secreted, cytoplasm, nucleus |
| Sp100 | 0.67691389 | 0.962 | 0.763 | 0.793 | 5.72E−27 | cytoplasm, nucleus |
| Ms4a6c | 0.72983164 | 0.975 | 0.777 | 0.797 | 9.96E−29 | plasma membrane |
| Sp110 | 0.59860205 | 0.854 | 0.682 | 0.799 | 6.47E−15 | nucleus |
| Mndal | 1.00023684 | 0.949 | 0.759 | 0.800 | 9.23E−33 | cytoplasm, nucleus |
| Slfn2 | 0.82911451 | 0.962 | 0.807 | 0.839 | 3.67E−35 | n/a |
| Samhd1 | 0.8106214 | 0.949 | 0.802 | 0.845 | 5.15E−25 | nucleus, plasma membrane |
| Selenow | 0.52113239 | 0.93 | 0.84 | 0.903 | 3.43E−12 | cytoplasm, plasma membrane |
| Sat1 | 0.55173701 | 0.847 | 0.768 | 0.907 | 2.79E−06 | cytosplasm |
| Ifitm3 | 0.59369026 | 0.975 | 0.916 | 0.939 | 1.45E−27 | cytoplasm, nucleus, plasma membrane |

Detection and/or Measurement of ISG+ DC

ISG+ DC have been found thus far almost exclusively in solid tumor microenvironments. Solid tumor samples may be harvested from subjects using a variety of techniques including resection and biopsy such as but not limited to core biopsy. Solid tumor samples may be digested in order to produce partially or completely disaggregated cell populations including but not limited to dissociated single cell suspensions. Alternatively, they may be sectioned and stained for the presence of target mRNA or protein.

Gene expression profiles (i.e., mRNA profiles) may be detected RNA sequencing (RNAseq) techniques such as bulk RNA sequencing (bulk-RNA-seq) techniques and single cell RNA sequencing (scRNAseq) techniques, among others. See for example Zilionis et al. Immunity, 50:1317-1334, 2019 which uses the inDrop scRNA-seq platform to perform transcriptomic analysis on single cell suspensions from lung cancer biopsies. Other methods for analyzing the transcriptional profile of a population of cells for the presence of ISG+ DC include RNA-FISH, microarrays (e.g., spotted oligonucleotide arrays), serial and cap analysis of gene expression (SAGE/CAGE), as well as others known in the art. Similar approaches may be used to detect and quantify ISG+ DC in solid cancer and tumor samples in the methods of this disclosure based on their expression of one or more of the gene subsets provided above. For example, the ISG+ DC may be distinguished from other DC clusters based on expression of Cxcl10, Ifit3 Rsad2/Viperin, Ifit1, Ifit1b11, Ifit2, Isg15, Ifit3b, Usp18, and Ifi204.

It will be understood that ISG+ DC may be defined and/or identified by a gene signature that comprises or consists of or consists essentially of any of the gene (or marker) sets provided herein or subsets thereof.

Protein expression profiles may be detected using techniques such as flow cytometry (e.g., FACS), CyTOF (using target-specific binding partners labeled with heavy metal ions), among others. ISG+ DC may be identified and thus detected and measured based on their cell surface expression profile, which may include cell surface proteins identified using scRNAseq data, provided herein. ISG+ DC may be defined and/or identified based on protein expression as XCR1−, BDCA-3− and MHC Class II+.

Gene or protein expression may also be analyzed using histochemistry. As examples, mRNA species may be detected via hybridization with gene-specific probes and proteins may be detected via antibodies that bind specifically to the protein of interest.

Detection of ISG+ DC from a population using either gene or protein expression profiles may be preceded by pre-selecting a DC population. Such pre-selection may be based on expression of DC markers such as H2-Ab1, Flt3 or Itgax. Alternatively, such pre-selection may be based on expression of immune cell markers such as but not limited to CD45.

Subjects in Need of Enhanced ISG+ DC Activity and/or Number

Subjects to be treated according to this disclosure have or at risk of having a solid cancer or tumor. Solid cancers or tumors of particular interest include liver/hepatic cancer, melanoma and sarcoma.

Certain aspects of this disclosure relate to the identification and/or treatment of subjects whose solid cancer or tumor(s) have undetectable or low levels of ISG+ DC. The methods for detecting and measuring ISG+ DC are described herein.

If the solid tumor is found to contain undetectable levels of ISG+ DC, the tumor will be considered negative for ISG+ DC. Regardless, these subjects would still be treated according to this disclosure, as such treatment may effect recruitment of ISG+ DC into the tumor microenvironment. Alternatively, tumors that show undetectable levels of ISG+ DC may nevertheless contain ISG+ DC but at very low levels that border on background. It is contemplated that even such low levels of ISG+ DC would still respond to the therapies provided herein.

Similarly, if the solid tumor is found to have low levels of ISG+ DC, the tumor will be treated with the agents provided herein to stimulate and/or proliferate the existing resident ISG+ DC and/or recruit ISG+ DC into the tumor. ISG+ DC level may be expressed for example in terms of number of ISG+ DC per certain number of tumor cells (i.e., frequency) or number of ISG+ DC per certain mass of tumor. The ISG+ DC cell presence may be determined based on a transcriptional signature, using for example single cell sequencing techniques. One such transcriptional signature consists of the gene markers in Table 2 (i.e., Cxcl10, Ifit3 Rsad2/Viperin, Ifit1, Ifit1b11, Ifit2, Isg15, Ifit3b, Usp18, and Ifi204).

As used herein, a solid cancer or tumor has a low level of ISG+ DC when the level of ISG+ DC is below the $50^{th}$ percentile, meaning that a solid cancer or tumor has a low level of ISG+ DC if 50% of similarly analyzed solid cancers or tumors have a higher ISG+ DC level. Low ISG+ DC level may also include equal to or below the $45^{th}$ percentile, equal to or below the $40^{th}$ percentile, equal to or below the $35^{th}$ percentile, equal to or below the $30^{th}$ percentile, equal to or below the $25^{th}$ percentile, equal to or below the $20^{th}$ percentile, equal to or below the $15^{th}$ percentile, equal to or below the $10^{th}$ percentile, equal to or below the $5^{th}$ percentile, or equal to or below the $1^{st}$ percentile. The ISG+ DC level distribution may be obtained by analysis of all solid tumors or tumors of a specific type. Thus, to ascertain whether a subject has a low ISG+ DC level, the ISG+ DC level of a representative plurality of tumors is determined, and this in turn dictates ISG+ DC levels corresponding to particular percentiles. determination of whether an ISG+ DC level is low will depend upon the distribution of ISG+DC levels in a population of tumors, typically tumors of the same type. Solid tumors of similar type will be assessed for their ISG+ DC content, and a population distribution will be generated from which low ISG+ DC levels will be set. A neg/low ISG+ DC content or level can be defined as described above for low ISG+ DC content or level, with the understanding that a negative content or level is an undetectable content or level (e.g., at or below background).

As used herein, the term "about" indicates a range within 10% of an indicated value.

Figure 4A:
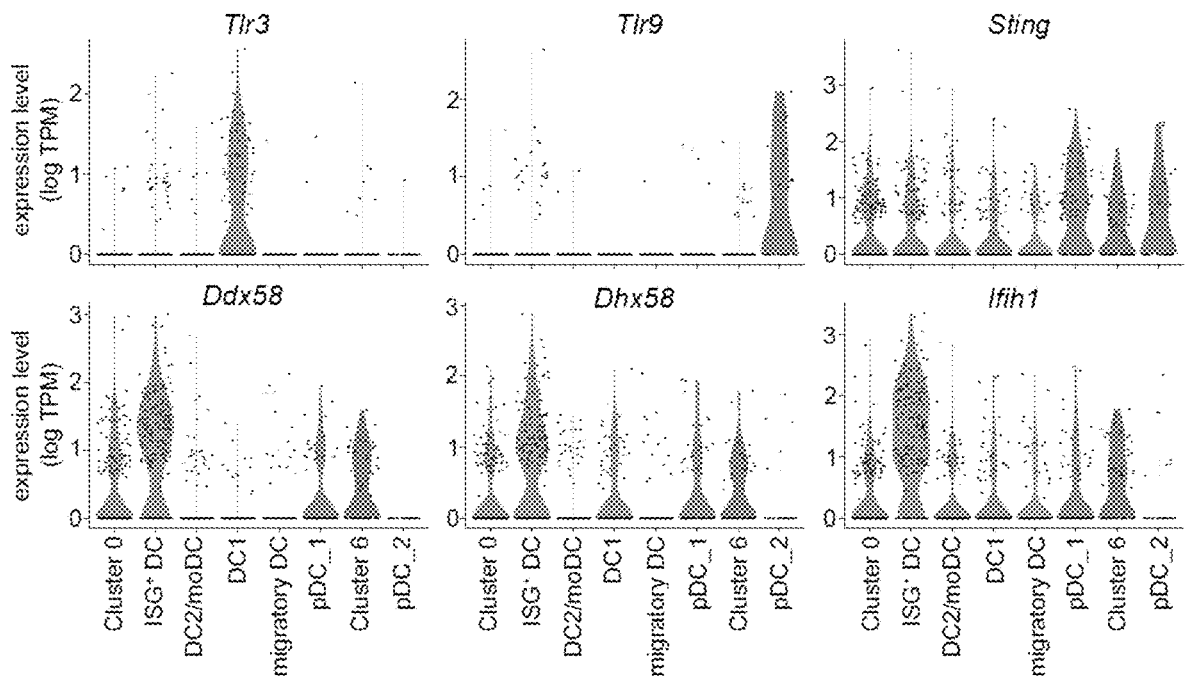
FIGS. 4A-4J show that ISG+ DC activated by tumor-derived dsRNA can restore tumor-reactive T cell responses against the progressor tumor in the absence of conventional cross-presentation.
Figure 4B:
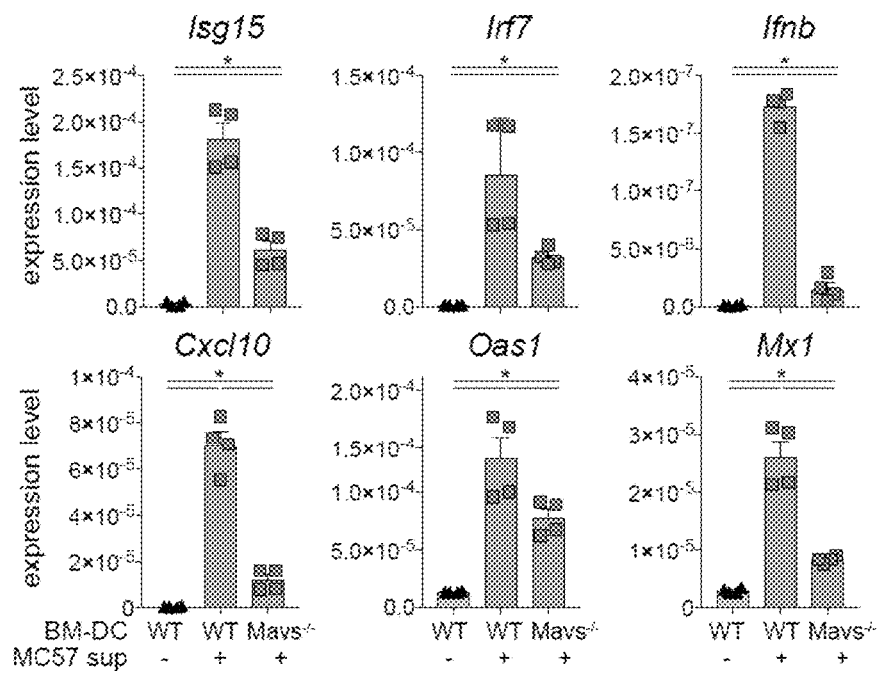
Figure 4C:
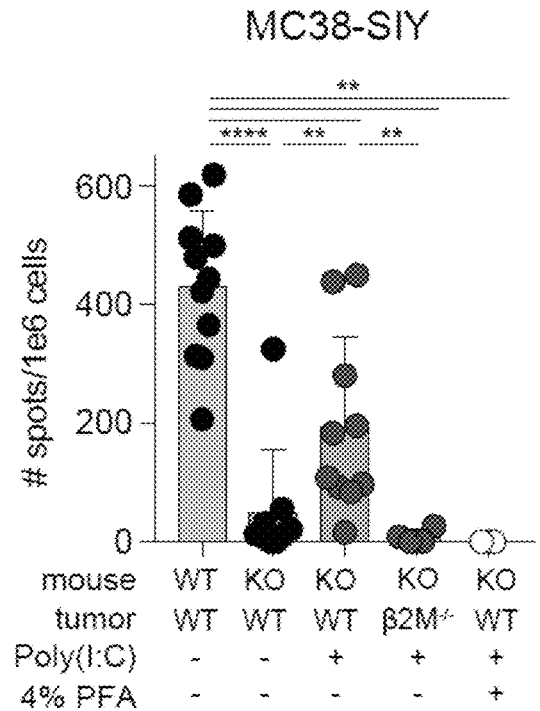
Figure 4D:
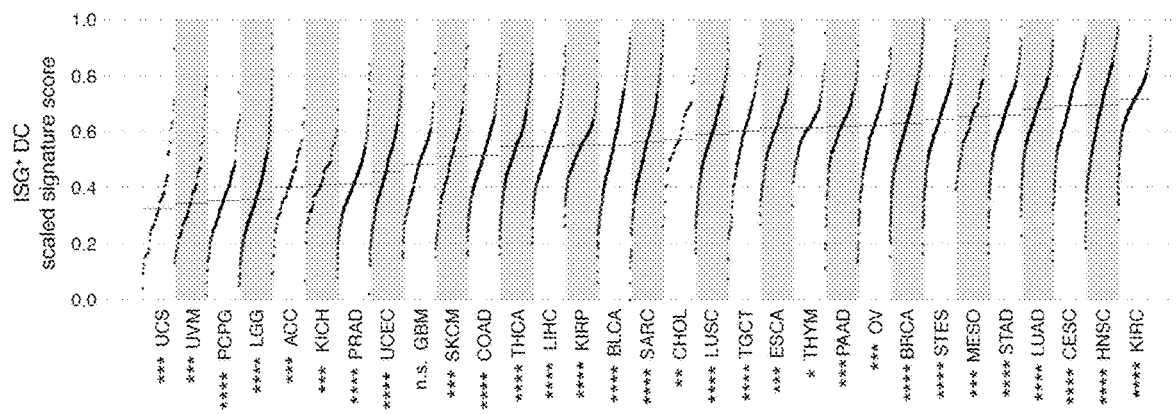
Figure 4E:
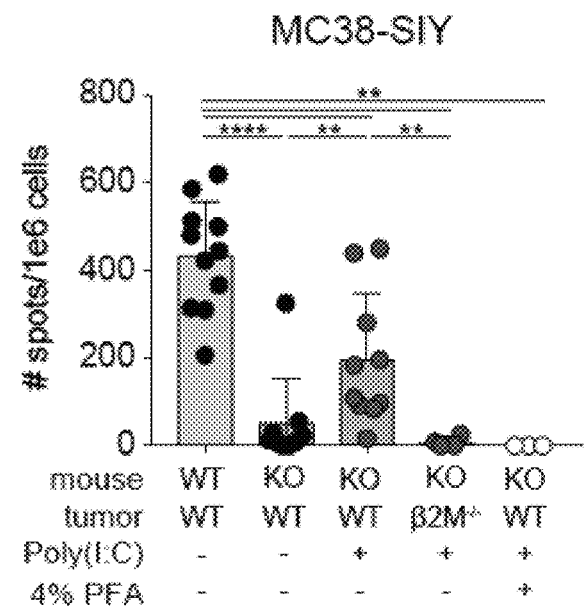
Figure 4F:
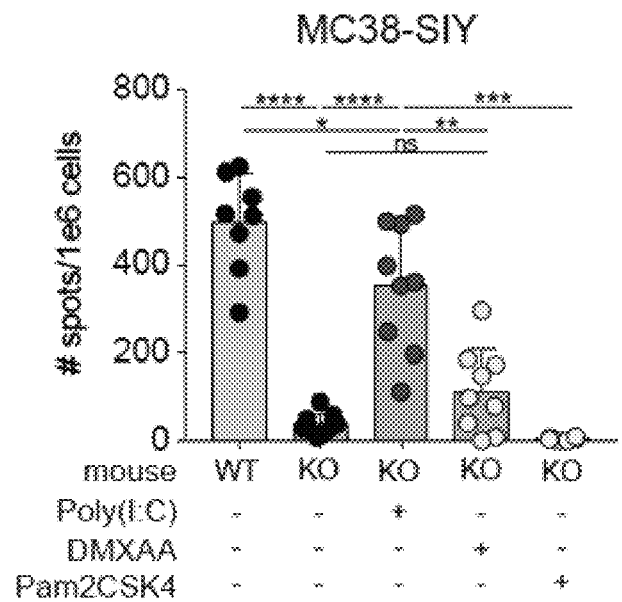
Figure 4G:
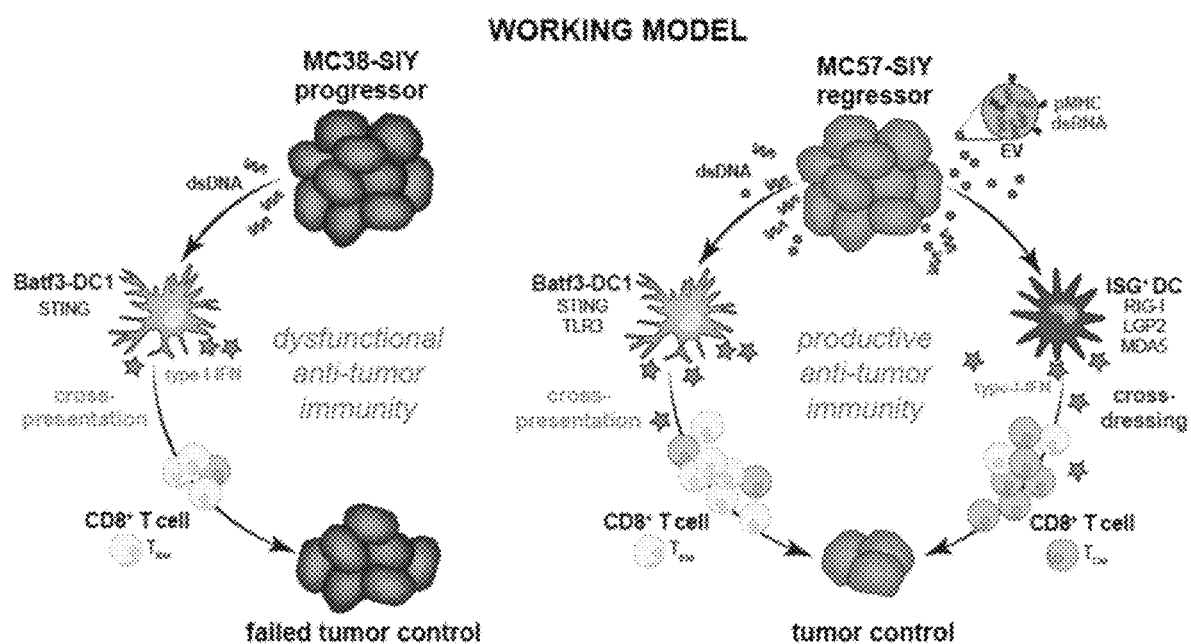
Figure 4H:
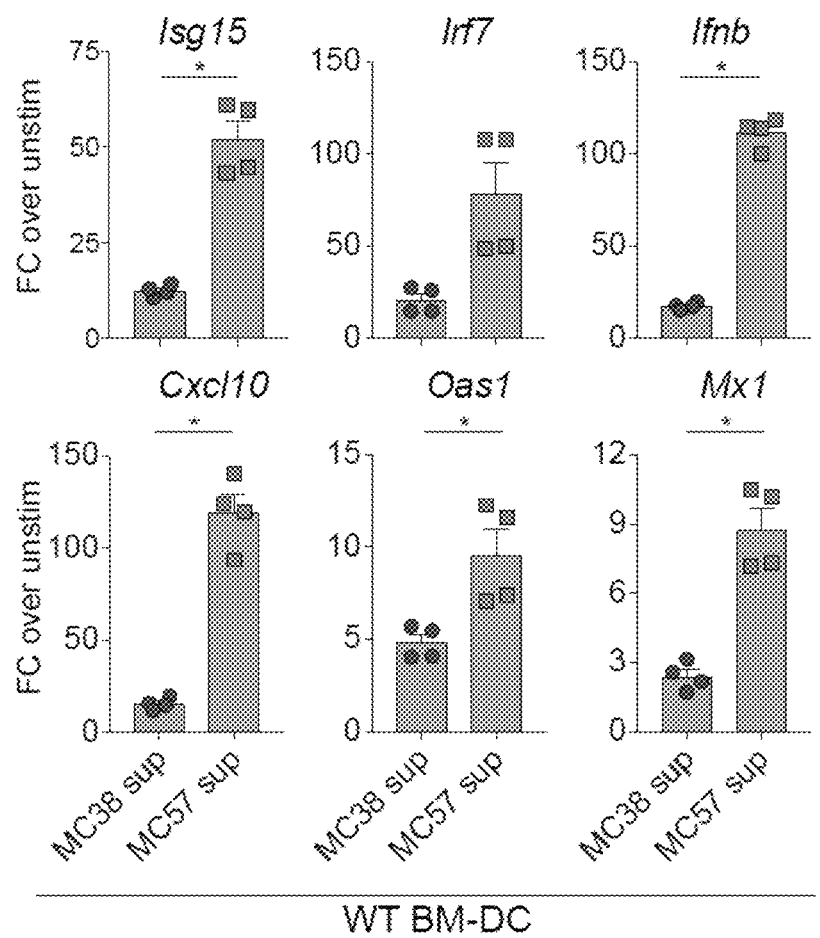
Figure 4I:
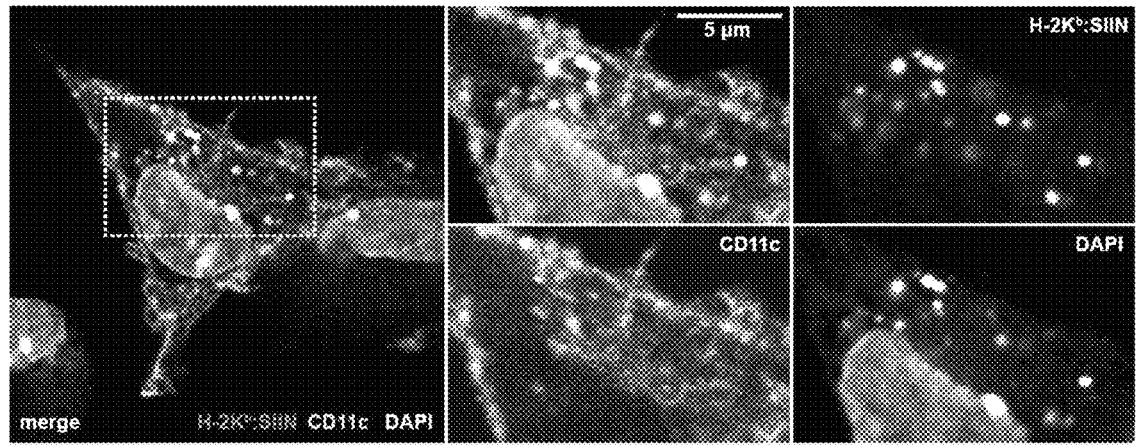
Figure 4J:
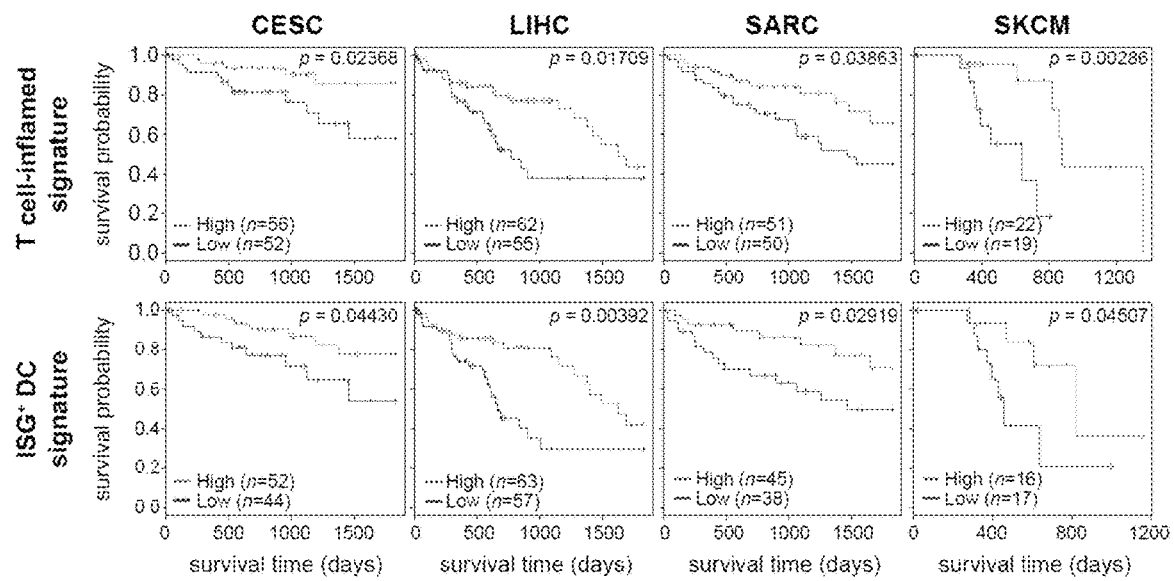

Subjects to be treated according to this disclosure may present with a solid cancer or tumor and then be further identified by measuring the level of ISG+ DC in their solid cancer or tumor following a resection or biopsy. Such subjects include those having cervical cancer such as cervical squamous cell carcinoma and endocervical adenocarcinoma (CESC), liver cancer such as hepatocellular carcinoma (LIHC), sarcoma (SARC), or melanoma such as skin/cutaneous melanoma (SKCM). As noted in the Examples, within the TCGA cohort for LIHC and SARC, patient stratification using the ISG+ DC signature resulted in increased significance of survival difference between the two patient groups. FIG. 4J provides Kaplan-Meier of 5-year survival probability of patients having CESC, LIHC, SARC and SKCM patients in the TCGA cohort. When the data are stratified by high (top z-score ≥1, red curve) or low (bottom z-score ≤-1, blue curve) scores based on expression correlation with the 160-gene T cell-inflamed signature (top panels) or the ISG+ DC signature (bottom panels), patients having a more robust T cell-inflamed signature or an ISG+ DC signature have better outcomes 5 years out.

Other subjects to be treated according to this disclosure may present with kidney clear cell carcinoma (KIRC), head and neck cancer (HNSC), lung adenocarcinoma (LUAD), stomach cancer (STAD), mesothelioma (MESO), esophageal carcinoma (STES), breast cancer (BRCA), ovarian cancer (OV), pancreatic cancer (PAAD), thymoma (THYM), esophageal cancer (ESCA), testicular cancer (TGCT), lung squamous cell carcinoma (LUSC), bile duct cancer (CHOL), bladder cancer (BLCA), kidney papillary cell carcinoma (KIRP), thyroid cancer (THCA), colon cancer (COAD), glioblastoma (GBM), uterine corpus endometrial carcinoma (UCEC), prostate adenocarcinoma (PRAD), kidney chromophobe (KICH), adrenocortical carcinoma (ACC), brain lower grade glioma (LGG), pheochromocytoma and paraganglioma (PCPG), uveal melanoma (UVM) and uterine carcinosarcoma (USC). As shown in FIG. 4D, 30 solid tumor types were found to have a significant correlation between the ISG+ DC transcriptional signature consisting of Cxcl10, Ifit3 Rsad2/Viperin, Ifit1, Ifit1b11, Ifit2, Isg15, Ifit3b, Usp18, and Ifi204 and a previously defined 160-gene T cell-inflamed signature (29).

Still other subjects may have Hodgkin lymphoma, lung cancer, renal cell cancer or other type of kidney cancer, skin cancer, oral cancer, throat cancer, rectal cancer, anal cancer, and colorectal cancer.

Subjects are typically mammalian subjects including but not limited to humans, domestic animals, agricultural animals, zoo animals, sport animals, companion animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes, etc. In certain embodiments, the subject is a human subject. In certain embodiments, the subject is a human in need of a cancer treatment.

Methods for Inducing/Recruiting ISG+ DC in ISG+ DC neg/low Tumors

This disclosure further contemplates the treatment of subjects having low or no (neg/low) ISG+ DC levels. These subjects may be treated with a single agent (e.g., a stand-alone therapy) or with a combination of two or more agents.

Certain of these agents may be used to increase ISG+ DC numbers, induce ISG+ DC activity, and/or recruit ISG+ DC in ISG+ DC neg/low tumors (or microenvironments). This class of agents may be referred to broadly herein as "ISG+ DC inducing agents". Examples of ISG+ DC inducing agents include dsRNA species and analogs thereof, poly I:C and analogs thereof, RIG-1 agonists, MDA5 agonists, MAVS pathway activators (including upstream and downstream activators), TLR3 agonists, TLR7/8 agonists, TLR9 agonists. ISG+ DC inducing agents may also include inhibitors of ADAR1, since loss of this RNA-editing enzyme is associated with production and accumulation of dsRNA species by tumors. Any of the foregoing agents may be used alone or in combination with another or others (e.g., combinations of 2, 3, 4, 5, 6, or more). Examples of agents within each of these classes are provided in Table 4.

These ISG+ DC inducing agents may be delivered systemically or locally including to or near the tumor microenvironment.

ISG+ DC inducing agents may be used in combination with other agents including but not limited to checkpoint inhibitor agents. These agents include but are not limited to anti-PD1/PDL1 blocking antibodies, anti-CTLA4 blocking antibodies, and anti-TIM3 blocking antibodies. Examples are provided in Table 4.

ISG+ DC inducing agents may be used in combination with cGAS/STING agonists and/or antagonists of co-stimulatory molecules of T cells (e.g., tumor necrosis factor receptor superfamily member 4 ligand (OX40L), cluster of differentiation 80 (CD80), interleukin 15 (IL15), or a combination thereof). Examples are provided in Table 4.

ISG+ DC inducing agents may also be used in combination with more traditional chemotherapeutic agents.

The disclosure contemplates that subjects in need of treatment may be first administered an ISG+ DC inducing agent followed by a secondary agent such as but not limited to those described herein. Treatment with the ISG+ DC inducing agent may involve a single or multiple administrations spaced over hours, days, or weeks. For example, the ISG+ DC inducing agent may be administered 1, 2, 3, 4, 5 or 6 days, or 1, 2 or 3 weeks, or 1, 2, 3 or more months before administration of the secondary agent(s). Alternatively, the ISG+ DC inducing agent may be administered substantially simultaneously with the secondary agent(s). The administration schedules of these two agent classes may be the same and/or they may be overlapping in whole or in part.

The two classes of agents may synergize with each other, intending that their combined anti-tumor effect may be greater than their additive individual effects. Alternatively, the use of the ISG+ DC inducing agent may be combined with lower doses of the secondary agents because the tumor is more responsive to the secondary agent following treatment with ISG+DC inducing agent.

TABLE 4

Examples of Therapeutic Agents polyI:C and analogues
    Romidepsin (Anwar et al., Med Res Rev. 2019 May; 39(3): 1053-1090)
    Pembrolizumab (Anwar et al., Med Res Rev. 2019 May; 39(3): 1053-1090)
    NY-ESO-1 (Anwar et al., Med Res Rev. 2019 May; 39(3): 1053-1090)
    DCVac-001 (Anwar et al., Med Res Rev. 2019 May; 39(3): 1053-1090)
    Hiltonol (Anwar et al., Med Res Rev. 2019 May; 39(3): 1053-1090)
RIG-I agonists
    5'ppp-dsRNA (US20170239336, US20180256691, US20190336615)
    polyribonucleic acid (RNA) (US20200061097)
    Stem Loop RNAs (SLRs), specifically Stem Loop RNA 14 (SLR14), as disclosed in US20200061097
    Double-stranded RNA (dsRNA) (US20200061097)
    Merck/Rigontec RGT100 (US20200061097)
    low molecular weight Poly(I:C) (US20120238540, US20140288044, US20150352108)
    RIG-I-like (RLR) agonists disclosed in US20200063141
MDA5 agonists
    Double-stranded RNA (dsRNA) (US20090081157)
        5'ppp-dsRNA (US20200054689)
        high molecular weight Poly(I:C) (US20120238540, US20140288044, US20150352108, US20110076296)
upstream activators of the MAVS pathway
    see US20190099470, US 20180092989, 20130005028
downstream activators of the MAVS pathway
    RIG-1 (Wu et al. Curr Opin Virol. 2015 June; 12: 91-98, Schenten Adv Immunol. 2011; 109: 87-124. doi: 10.1016/B978-0-12-387664-5.00003-0.)
    MDA5 (Wu et al. Curr Opin Virol. 2015 June; 12: 91-98, Schenten Adv Immunol. 2011; 109: 87-124. doi: 10.1016/B978-0-12-387664-5.00003-0.)
    Other RIG-1 like receptors (Wu et al. Curr Opin Virol. 2015 June; 12: 91-98)
TLR3 agonists
    dsRNA (US20110076296, US20120238540)
    polyadenylic-polyuridylic acid (PolyAU) (US20110076296, US20200063141)
    polyinosinic-polycytidylic acid (Poly(I:C)) (US20120238540, US20140288044, US20150352108, US20200069795, (US20200063141)
    HILTONOL ® (poly ICLC) (US20200063141, US20200061173, Anwar et al., Med Res Rev. 2019 May; 39(3): 1053-1090)
    RIBOXXIM ® (RGIC ®100) (US20200063141)
    RIBOXXON ® (RGIC ®50 bioconjugate) (US20200063141)
    RIBOXXOL ® (RGIC ®50) (US20200063141)
    ARNAX (Adv Drug Deliv Rev. 2019 July; 147: 37-43. doi: 10.1016/j.addr.2019.07.008. Epub 2019 Jul. 11)
TLR7 agonists
    Resiquimod/R848 (TLR 7/8 agonist) (US20190336615, US20200063141, US20200017451, Anwar et al., Med Res Rev. 2019 May; 39(3): 1053-1090)
    GS-9620 (Vesatolimod) (US20200063141, US20200017451, Anwar et al., Med Res Rev. 2019 May; 39(3): 1053-1090))
    Imiquimod/R837 (ALDARA ™) (US20200063141, US20200017451, Anwar et al., Med Res Rev. 2019 May; 39(3): 1053-1090))
    Single stranded RNA (ssRNA) (US20200063141)

TABLE 4-continued

| | Examples of Therapeutic Agents |
|---|---|
| | loxoribine (a guanosine analogue derivatized at positions N7 and C8) (US20200063141) |
| | MEDI9197 (TLR7/8 agonist) (US20200054689, US20200017451, US20200031930) |
| | imidazoquinoline compounds (e.g., imiquimod and resiquimod), or derivatives (US20200063141, Anwar et al., Med Res Rev. 2019 May; 39(3): 1053-1090) |
| | GSK-2245035 (US20200017451, Anwar et al., Med Res Rev. 2019 May; 39(3): 1053-1090, Aryan et al., Int Arch Allergy Immunol. 2014; 164(1): 46-63. doi: 10.1159/000362553. Epub 2014 May 21) |
| | GSK-2245053 (Anwar et al., Med Res Rev. 2019 May; 39(3): 1053-1090) |
| | DSR-6434, DSP-3025, IMO-4200, MCT-465, 3M-051, SB-9922, 3M-052, Limtop, TMX-30X, TMX-202, RG-7863, RG-7795, and additional compounds disclosed in US20100143301, US20110098248, and US20090047249 (Gilead Sciences) (US20200017451) |
| | 852A (Anwar et al., Med Res Rev. 2019 May; 39(3): 1053-1090) |
| | RO7020531 (Anwar et al., Med Res Rev. 2019 May; 39(3): 1053-1090) |
| | RO6864018 (Anwar et al., Med Res Rev. 2019 May; 39(3): 1053-1090) |
| | IMO-8400 (TLR 7/8/9 agonist) (Anwar et al., Med Res Rev. 2019 May; 39(3): 1053-1090) |
| | CPG-52364 (TLR 7/8/9 agonist) (Anwar et al., Med Res Rev. 2019 May; 39(3): 1053-1090) |
| | CL307, PF-4878691, isatoribine, SM-324405, SM-324406, AZ12441970, and AZ12443988 (US20200031930) |
| | AZD8848 (Aryan et al., Int Arch Allergy Immunol. 2014; 164(1): 46-63. doi: 10.1159/000362553. Epub 2014 May 21) |
| | CL097 (TLR7/8 agonist) (Du et al., Vaccine. 2010 Aug. 31; 28(38): 6273-81. doi: 10.1016/j.vaccine.2010.06.117. Epub 2010 Jul. 15) |
| | Gardiquimod (Du et al., Vaccine. 2010 Aug. 31; 28(38): 6273-81. doi: 10.1016/j.vaccine.2010.06.117. Epub 2010 Jul. 15, Buitendijk et al., AIDS Res Hum Retroviruses. 2013 June; 29(6): 907-918.) |
| TLR8 agonists | |
| | MEDI9197 (TLR7/8 agonist) (US20200054689, Anwar et al., Med Res Rev. 2019 May; 39(3): 1053-1090), US20200031930) |
| | Motolimod/VTX-2337 (US20200017451, Anwar et al., Med Res Rev. 2019 May; 39(3): 1053-1090, US20200031930) |
| | CL075 (US20200031930, Du et al., Vaccine. 2010 Aug. 31; 28(38): 6273-81. doi: 10.1016/j.vaccine.2010.06.117. Epub 2010 Jul. 15) |
| | SSRNA (Anwar et al., Med Res Rev. 2019 May; 39(3): 1053-1090) |
| | Resiquimod/R848 (TLR 7/8 agonist) (US20200017451, Anwar et al., Med Res Rev. 2019 May; 39(3): 1053-1090)) |
| | 3M-051, 3M-052, MCT-465, IMO-4200, VTX-763 (US20200017451) |
| | VTX-1463 (US20200017451, Aryan et al., Int Arch Allergy Immunol. 2014; 164(1): 46-63. doi: 10.1159/000362553. Epub 2014 May 21) |
| | IMO-8400 (TLR 7/8/9 agonist) (Anwar et al., Med Res Rev. 2019 May; 39(3): 1053-1090) |
| | CPG-52364 (TLR 7/8/9 agonist) (Anwar et al., Med Res Rev. 2019 May; 39(3): 1053-1090) |
| | Additional compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics) (US20200017451) |
| TLR9 agonists | |
| | CpG DNA polymers; (CpGs) (US20200061097, US20200069795, US20200063141, Anwar et al., Med Res Rev. 2019 May; 39(3): 1053-1090) |
| |     CpG oligodeoxynucleotides (CpG ODNs) (US20200063141, US20200061173, Anwar et al., Med Res Rev. 2019 May; 39(3): 1053-1090) |
| |         Class A CpG ODN (CpG-A ODN) (US20200063141) |
| |         Class B CpG ODN (CpG-B ODN) (US20200063141) |
| |         Class C CpG ODN (CpG-B ODN) (US20200063141) |
| | Checkmate CMP-001 (US20200061097) |
| | plasmid DNA (i.e. non-coding plasmid DNA) (US20200069795) |
| | IC31 (US20200061173) |
| | BB-001, BB-006, IMO-2055, IMO-3100, IR-103, IMO-9200, agatolimod, DIMS-9054, DV-1079, DV-1179, litenimod (US20200017451) |
| | IMO-2125 (US20200017451, US20200061097, Anwar et al., Med Res Rev. 2019 May; 39(3): 1053-1090) |
| | AZD-1419 (Dynavax) (US20200017451, Anwar et al., Med Res Rev. 2019 May; 39(3): 1053-1090, Aryan et al., Int Arch Allergy Immunol. 2014; 164(1): 46-63. doi: 10.1159/000362553. Epub 2014 May 21) |
| | CYT-003-QbG10 (US20200017451, Anwar et al., Med Res Rev. 2019 May; 39(3): 1053-1090, Aryan et al., Int Arch Allergy Immunol. 2014; 164(1): 46-63. doi: 10.1159/000362553. Epub 2014 May 21) |

TABLE 4-continued

| | Examples of Therapeutic Agents |
|---|---|
| | CYT-003 (US20200017451, Anwar et al., Med Res Rev. 2019 May; 39(3): 1053-1090) |
| | Leftolimod (MGN-1703) (US20200017451, Anwar et al., Med Res Rev. 2019 May; 39(3): 1053-1090) |
| | IMO-8400 (TLR 7/8/9 agonist) (US2020001745, Anwar et al., Med Res Rev. 2019 May; 39(3): 1053-1090) |
| | CPG-52364 (TLR 7/8/9 agonist) (Anwar et al., Med Res Rev. 2019 May; 39(3): 1053-1090) |
| | CPG-7907 (Anwar et al., Med Res Rev. 2019 May; 39(3): 1053-1090) |
| | CPG-10104 (Anwar et al., Med Res Rev. 2019 May; 39(3): 1053-1090) |
| | EMD 1201081 (cetuximab) (Anwar et al., Med Res Rev. 2019 May; 39(3): 1053-1090) |
| | SD-101 (Anwar et al., Med Res Rev. 2019 May; 39(3): 1053-1090) |
| | AEV0675 (Coley Pharmaceuticals) (Aryan et al., Int Arch Allergy Immunol. 2014; 164(1): 46-63. doi: 10.1159/000362553. Epub 2014 May 21) |
| | SAR21609 (Coley Pharmaceuticals) (Aryan et al., Int Arch Allergy Immunol. 2014; 164(1): 46-63. doi: 10.1159/000362553. Epub 2014 May 21) |
| | IMO2134 (Idera Pharmaceutics) (Aryan et al., Int Arch Allergy Immunol. 2014; 164(1): 46-63. doi: 10.1159/000362553. Epub 2014 May 21) |
| | Amb a1-1018 ISS (Aryan et al., Int Arch Allergy Immunol. 2014; 164(1): 46-63. doi: 10.1159/000362553. Epub 2014 May 21) |
| cGAS agonists | |
| | Cyclic GMP-AMP synthase (US 20200031930, US20190382492) |
| | Cyclic di-GMP (Li et al., J Hematol Oncol. 2019; 12: 35) |
| | 3'3'-cGAMP (Li et al., J Hematol Oncol. 2019; 12: 35) |
| | 2'3'-cGAMP (Li et al., J Hematol Oncol. 2019; 12: 35) |
| | ML RR-S2 CDG (Li et al., J Hematol Oncol. 2019; 12: 35) |
| | ML RR-S2 cGAMP (Li et al., J Hematol Oncol. 2019; 12: 35) |
| | ML RR-S2 CDA (ADU-S100) (Li et al., J Hematol Oncol. 2019; 12: 35) |
| | DMXAA (Li et al., J Hematol Oncol. 2019; 12: 35) |
| | DiABZI (Li et al., J Hematol Oncol. 2019; 12: 35) |
| Sting agonists | |
| | cyclic dinucleotide (US20170239336, US20180256691, US20190336615) |
| |     cyclic di-GMP (cyclic dimeric guanosine 5'-monophosphate) (US20200054689) |
| |     cyclic di-AMP (cyclic dimeric adenosine 5'-monophosphate) (US20200054689) |
| |     cyclic GMP-AMP (cGAMP) (US20200054689) |
| | structures of Sting agonists in paragraph [0385] of US20190336615 |
| | Merck MK-1454 or Aduro/Novartis Adu-S100 (US20200061097) |
| | ML RR-S2 CDA or ADU-S100 (binds both human and mouse STING) (US20200054689) |
| | Benzo[b]thiophene compounds (specific compounds disclosed in U.S. Pat. No. 10,414,747) |
| anti-PD1/PDL1 blocking antibodies | |
| | Libtayo (cemiplimab, anti-PD-1) |
| | Opdivo (nivolumab, anti-PD-1) |
| | Keytruda (pembrolizumab, anti-PD-1) |
| | Bavencio (avelumab, anti-PD-L1) |
| | Imfinzi (durvalumab, anti-PD-L1) |
| | Tecentriq (atezolizumab (anti-PD-L1)) |
| | In experimental phase: |
| |     Spartalizumab (PDR001) (Novartis) |
| |     Camrelizumab (SHR1210) (Jiangsu HengRui Medicine Co.) |
| |     Sintilimab (IBI308) (Innovent and Eli Lilly) |
| |     Tislelizumab (BGB-A317) |
| |     Toripalimab (JS 001) |
| |     Nivolumab (BMS-936558) (Bristol Meyers Squibb) |
| |     AMP-224 (GlaxoSmithKline) |
| |     AMP-514 (GlaxoSmithKline) |
| |     KN035 |
| |     CK-301 (Checkpoint Therapeutics) |
| |     AUNP12 (Aurigene and Laboratoires) |
| |     CA-170 (Aurigene/Curis) |
| |     BMS-986189 (Bristol-Myers Squibb) |
| anti-CTLA4 blocking antibodies (antibodies that block the interaction between CTLA4 and CD80/CD86/B7-1/B7-2) | |
| | Yervoy (ipilimumab) |
| |     (BMS-734016, MDX-010, MDX-101; Bristol-Myers Squibb) |
| |     (US20200061097) |

TABLE 4-continued

Examples of Therapeutic Agents

Tremelimumab (ticilimumab, CP-675,206; MedImmune LLC) (US20200061097)
anti-Tim3 blocking antibodies (antibodies that block the interaction between Tim3 and HMGB1)
    MGB453 (Novartis) (US20200063141, He et al. Onco Targets Ther. 2018; 11: 7005-7009)
    TSR-022 (Tesaro) (US20200063141, He et al. Onco Targets Ther. 2018; 11: 7005-7009)
    LY3321367 (Eli Lilly) (US20200063141, He et al. Onco Targets Ther. 2018; 11: 7005-7009)

The term "antibody" encompasses an immunoglobulin molecule that recognizes and specifically binds to a target, e.g., PD-1, PD-L1, CTLA-4, through at least one antigen recognition site within its variable region. The term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of an IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations.

In some embodiments of this disclosure, the antibody is a blocking antibody. "Blocking antibody" refers to an antibody which inhibits or reduces the biological activity of the antigen it binds. Blocking antibodies may but need not substantially or completely inhibit the biological activity of the antigen to which they bind. In some aspects, the biological activity is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100%.

An antigen-binding antibody fragment, as used herein, refers to a portion of the antibody that binds specifically to the target antigen.

This disclosure further contemplates compositions that mimic a tumor cell and/or its derivatives or that mimic an ISG+ DC. Such compositions may include peptide-MHC Class I complexes. The peptides of such complexes are antigenic in nature (i.e., they are presented by the MHC Class I molecule to T cells and thereby stimulate such T cells in an antigen-specific manner). Such compositions may include uncomplexed MHC Class I molecules and may be used with a second line of therapy that creates tumor cell debris (and thus tumor-derived antigenic peptides). Such second line of therapy may include localized (e.g., stereotactic) radiation, chemotherapeutics, and the like.

The MHC Class I molecules (a complex of alpha and beta2 chains) may be subject-specific (i.e., autologous). The entire peptide-MHC Class I complex may be isolated from a subject or it may be synthesized ex vivo optionally starting from a tissue fragment obtained from the subject. The MHC Class I molecules, optionally autologous in nature, may be loaded with antigenic peptides such as tumor-derived peptides, synthetic peptides derived from shared tumor antigens, synthetic peptides derived from tumor-specific neo antigens produced by single nucleotide mutations or by INDELs, and the like, prior to administration or they may be loaded with certain peptides in vivo.

Such compositions may further comprise ISG+ DC inducing agents such as dsRNA, polyI:C and the like, although such agents may be physically separate from the particles.

As used herein, "isolated" refers to a substance or entity that has been separated from at least some of the components with which it was associated (whether in nature or in an experimental setting). Isolated substances (e.g., peptides, cells, MHC Class I molecules, etc.) can have varying levels of purity relating to the substances from which they have been associated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Such peptide-MHC Class I complexes may be used, including administered, in an isolated form or as part of a nanoparticle or microparticle, typically on the surface of such particles. The particles may comprise polymers such as biodegradable or biocompatible polymers and/or lipids. Such particles may comprise, in addition to the MHC Class I-peptide complex, antibodies or antibody fragments that can target the particle to a tumor or tumor microenvironment.

Nanoparticles are typically on the order of micrometers or smaller in diameter. For example, a nanoparticle may have a diameter of 500 nm or less.

The term "polymer," as used herein, is a molecular structure comprising one or more repeat units (monomers), connected by covalent bonds. The repeat units may all be identical, or in some cases, there may be more than one type of repeat unit present within the polymer. A biodegradable polymer is a polymer that is able to degrade, chemically and/or biologically, within a physiological environment, such as within the body without significant toxic effect. A biocompatible polymer is compatible with living cells, tissues, organs or systems posing little to no risk of injury, toxicity or rejection by the immune system.

Examples of suitable biodegradable polymers include polylactide-polyglycolide, poly-(orthoesters), poly(anhydrides), di-block polymer (e.g., diblock poly(lactic)acid-polyethylene glycol copolymer, or diblock poly(lactic)-co-poly (glycolic) acid-poly(ethylene)glycol copolymer.

Lipid-based particles may be in the form of vesicles or liposomes comprising a lipid bilayer, or multilamellar vesicles.

Examples of suitable lipids include fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoyl-phosphatidylcholine; dipentadecanoylphosphatidylcholine; dilauroylphosphatdylcholine; 1,2-dipalmitoyl-sn-glycero-3-phosphatidylcholine (DPPC); distearoylphosphatidylcholine (DSPC); and diarachidonylphosphatidylcholine (DAPC); phosphatidylethanolamines, such as dioleoylphosphatidylethanolamine, 1,2-dipalmitoyl-sn-glycero-3-phosphatidylethanolamine (DPPE) and distearoyl-phosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as 1,2-dipalmitoyl-sn-glycero-3-phosphatidic acid (DPPA) and distearoylphosphatidic acid (DSPA); palmitic acid; stearic acid; arachidonic acid; and oleic acid.

Other suitable lipids include phosphatidylcholines, such as diolecylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoylphosphatidylethanolamine; phosphatidylserines; phosphatidyl-glycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methyl-amino)octadecanoyl]-2-amino-palmitic acid; 1,2-dioleoyl-sn-glycerol; 1,2-dipalmitoyl-sn-3-succinylglycerol; 1,3-dipalmitoyl-2-succinylglycerol; and 1-hexadecyl-2-palmitoyl-glycerophosphoethanolamine and palmitoylhomocysteine; lauryltrimethylammonium bromide (lauryl-=dodecyl-); cetyltrimethylammonium bromide (cetryl-=hexadecyl-); myristyltrimethylammonium bromide (myristyl-=tetradecyl-); alkyldimethylbenzylammonium chlorides, such as wherein alkyl is a C.sub.12, C.sub.14 or C.sub.16 alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1-2,3-dioleoyloxy)-propyl]-N,N,N-trimethylammonium chloride (DOTMA); 1,2-dioleoyloxy-3-(trimethylammonio)propane (DOTAP); and 1,2-dioleoyle-(4'-trimethylammonio)-butanoyl-sn-glycerol (DOTB).

As used herein, "treating" or "treatment" or "therapy" refers to partially or completely alleviating, ameliorating, improving, relieving, delaying onset of, inhibiting progression of, reducing severity of, and/or reducing incidence of a cancer. For example, "treating" cancer can refer to inhibiting survival, growth, and/or spread of a tumor or tumor cells.

The agents provided herein, including ISG+ DC inducing agents, secondary agents, cells and cellular mimics, may be used in effective amounts. An "effective amount" of an agent is that amount sufficient to effect beneficial or desired results, for example, clinical results, and, as such, an "effective amount" depends upon the context in which it is being applied. For example, in the context of administering an agent to treat a tumor, an effective amount of an agent may be an amount sufficient to reduce or decrease a size of a tumor or to inhibit a tumor growth, as compared to the response obtained without administration of the agent.

In the context of ISG+ DC inducing agents, the effective amount may be the amount sufficient to increase the number of ISG+ DC in a tumor microenvironment, by stimulating proliferation of such cells already resident in the tumor microenvironment and/or by recruiting such cells into the tumor microenvironment, or the amount sufficient to stimulate the activity of such cells (e.g., stimulating cross-dressing by such cells). Effective amounts may be determined using in vitro assays, such as those described herein, or they may be determined through clinical trials.

In some instances, in which the ISG+ DC inducing agent is administered with a secondary agent, such as a checkpoint inhibitor, the effective amount is an amount that provides an anti-tumor effect in excess of that achieved when the secondary agent is used alone or without the ISG+ DC inducing agent. Such effect may be a decreasing or stabilizing size of a tumor.

The compositions of the present disclosure may be administered intravenously, intradermally, intraarterially, intralesionally, intratumorally, intracranially, intraarticularly, intraprostatically, intrapleurally, intratracheally, intranasally, intravitreally, intravaginally, intrarectally, topically, intramuscularly, intraperitoneally, subcutaneously, subconjunctivally, intravesicularly, mucosally, intrapericardially, intraumbilically, intraocularally, orally, locally, inhalation (e.g., aerosol inhalation), injection, infusion, continuous infusion, localized perfusion, via a catheter, via a lavage, in creams, or by other method or any combination of the forgoing as would be known to one of ordinary skill in the art (see, for example, Remington's Pharmaceutical Sciences (1990), incorporated herein by reference).

In certain embodiments, particularly those involving ISG+ DC inducing agents, intratumoral administration is contemplated. Intratumoral refers to administration within a tumor.

The agents of this disclosure, including but not limited to ISG+ DC inducing agents and secondary agents, are administered as pharmaceutical compositions. Such pharmaceutical compositions include the agents provided herein, typically together with a pharmaceutically-acceptable carrier. Such compositions are nontoxic and typically sterile. The components of the pharmaceutical compositions are combined in a manner that precludes interaction that would substantially impair their desired pharmaceutical efficiency.

Moreover, for animal (e.g., human) administration, it will be understood that such compositions should meet sterility, pyrogenicity, general safety and purity standards. The compounds are generally suitable for administration to humans or mammals. Compositions and carriers suitable for use as or with lipid-based nanoparticles are disclosed in U.S. Pat. No. 7,404,969.

As used herein, the term "pharmaceutically-acceptable carrier" refers to one or more compatible solid or liquid filler, diluents or encapsulating substances which are suitable for administration to a human or other subject contemplated by the disclosure. A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The following examples are provided to illustrate specific instances of the practice of the present disclosure and are not intended to limit the scope of the invention. As will be apparent to one of ordinary skill in the art, the present invention will find application in a variety of compositions and methods.

EXAMPLES

Example 1

To identify DC subsets that are associated with productive T cell responses, the DC infiltrate of a spontaneously cleared regressor tumor (MC57-SIY fibrosarcoma) was compared with that of a progressively growing tumor (MC38-SIY colon carcinoma) (FIG. 1A). Both lines are well-established in the immuno-oncology field and express the model T cell antigen SIYRYYGL (SEQ ID NO: 23) (SIY) to track tumor-specific T cell responses. While MC38-SIY is associated with the induction of T cell dysfunction, T cell responses against MC57-SIY do not acquire the dysfunctional phenotype (3).

Figure 1B:
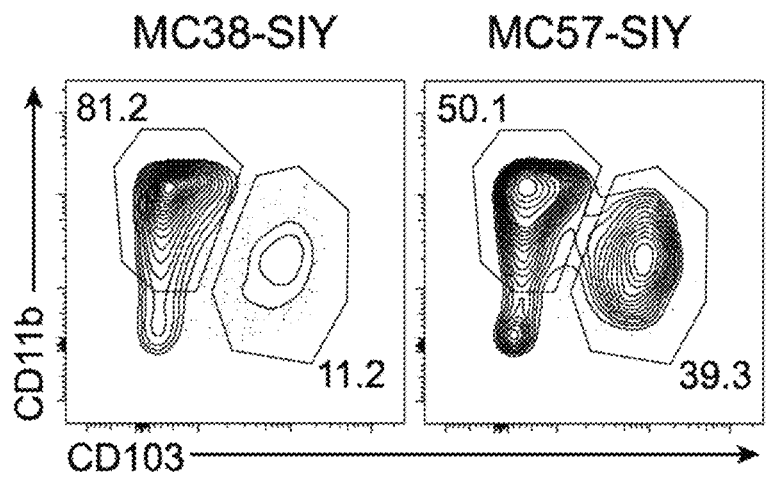
FIG. 1B shows representative flow cytometric analysis of conventional DC (cDC) subsets, CD103+ DC1 and CD11b+ DC2 (pre-gated on live CD45+ MHCII+ Ly6C− F4/80− CD11c+ CD24$^{hi}$), in MC38-SIY and MC57-SIY tumors from WT mice at day 7 following tumor inoculation.
Figure 1C:
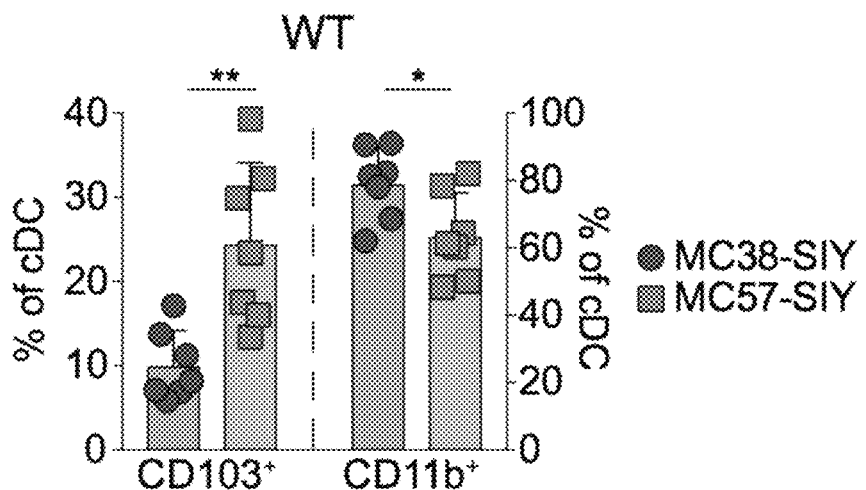
FIG. 1C shows quantification of CD103+ DC1 and CD11b+ DC2 as a percentage of cDC in MC38-SIY (circles) and MC57-SIY (squares) at day 7 post-tumor inoculation in WT mice. Data are pooled from individual mice (n=7) from two independent experiments.
Figure 1D:
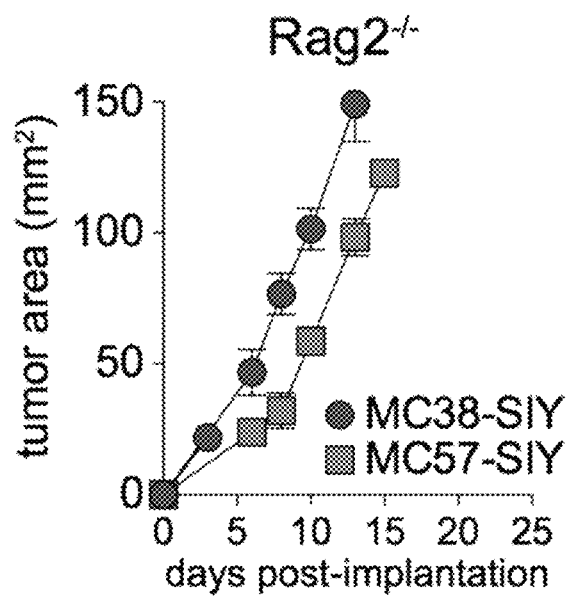
FIG. 1D shows tumor outgrowth (mm2) of MC38-SIY (circles) and MC57-SIY (squares) in Rag2−/− mice. Data are representative of two independent experiments with MC38-SIY n=3; MC57-SIY n=3 mice.
Figure 1E:
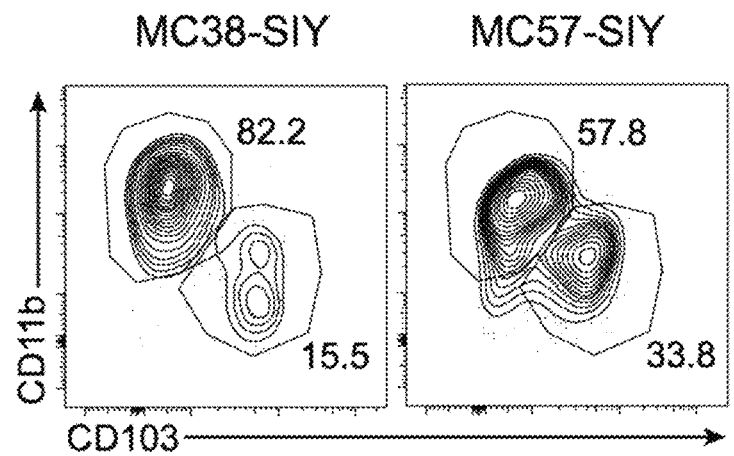
FIG. 1E shows representative flow cytometric analysis of CD103+ DC1 and CD11b+ DC2 in MC38-SIY and MC57-SIY tumors from Rag2−/− mice at day 15 post-tumor inoculation.
Figure 1F:
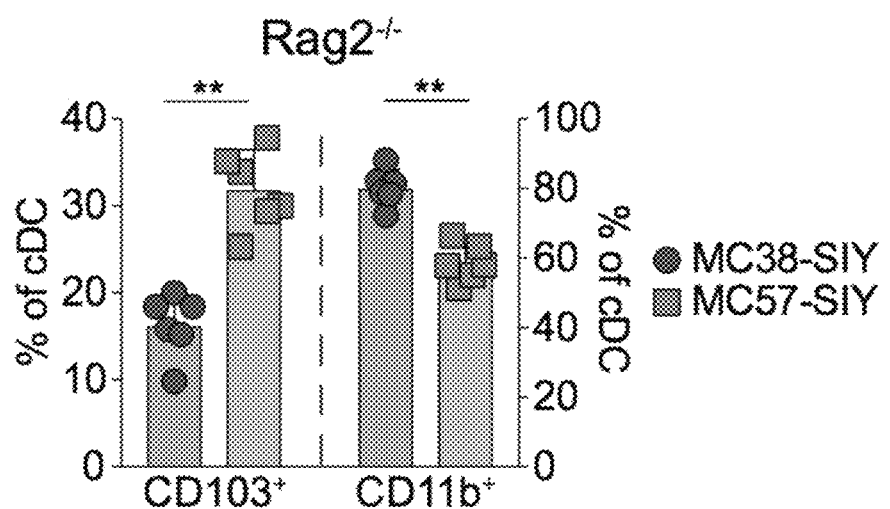
FIG. 1F shows quantification of CD103+ DC1 and CD11b+DC2 as a percentage of cDC in MC38-SIY (circles) and MC57-SIY (squares), at day 15 post-tumor challenge in Rag2−/− mice. Data are pooled from individual mice (n=6) from two independent experiments.
Figure 1G:
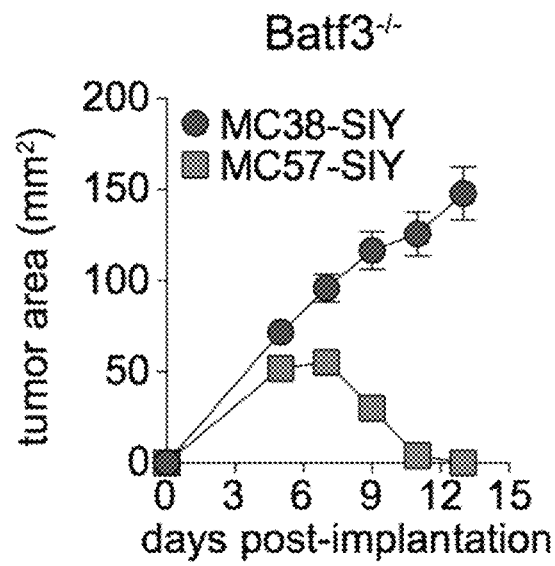
FIG. 1G shows tumor outgrowth ($mm^2$) of MC38-SIY (circles) and MC57-SIY (squares) in Batf3−/− mice. Data are representative of two independent experiments with MC38-SIY n=3; MC57-SIY n=3 mice.
Figure 1H:
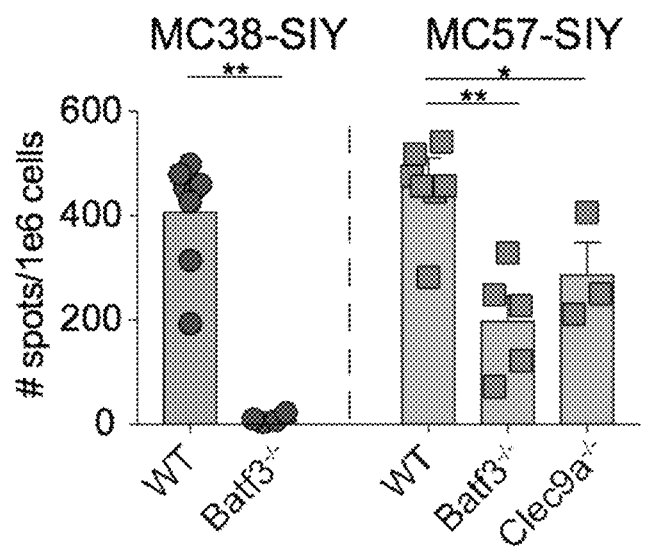
FIG. 1H shows ELISpot quantification of IFNγ-producing splenocytes from WT, Batf3−/−, and Clec9a−/− mice bearing MC38-SIY (circles) or MC57-SIY (squares) tumors at day 5 post-tumor inoculation (MC38-SIY: WT n=8; Batf3−/− n=4; MC57-SIY: WT n=6; Batf3−/− n=5; Clec9a−/− n=3 mice) from two independent experiments.
Figure 1I:
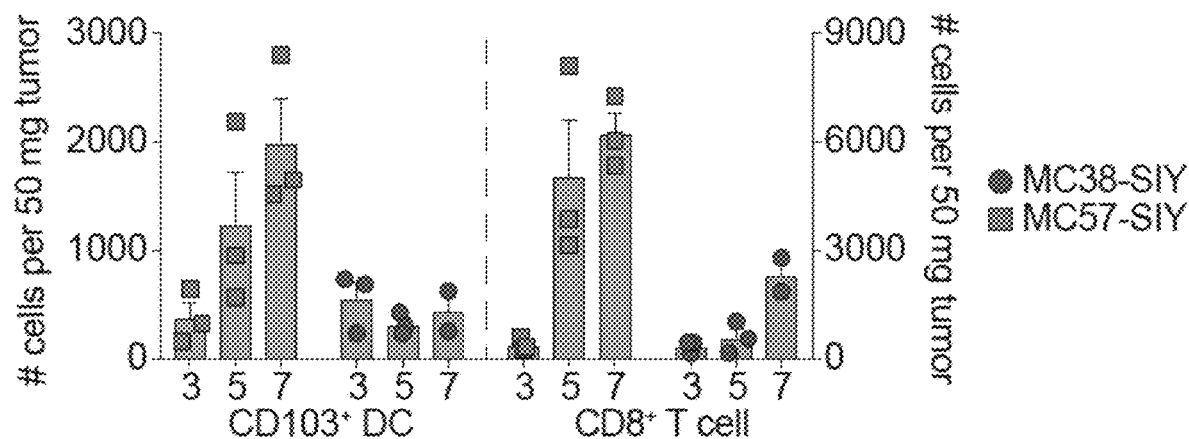
FIG. 1I shows the number of CD103+ DC1 and CD8+ T cells in 50 mg of MC38-SIY (circles) and MC57-SIY (squares) tumors at days 3, 5, and 7 following tumor implantation in WT mice. Data are representative of two independent experiments with n=3 mice.
Figure 1J:
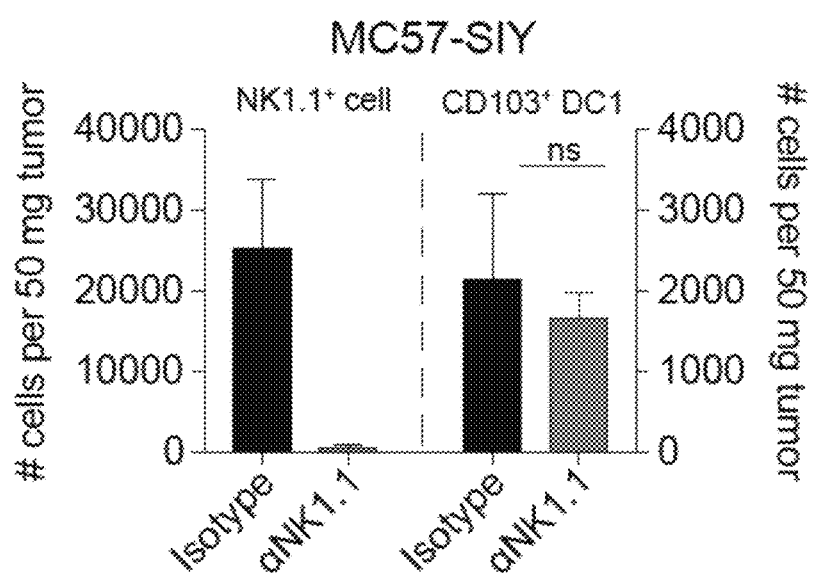
FIG. 1J shows the number of NK1.1+ cells and CD103+ DC1 in 50 mg of MC57-SIY tumors at 7 following tumor implantation in WT mice treated with anti-NK1.1 to deplete Natural Killer (NK) cells or an isotype control. Data are representative of two independent experiments with n=4 mice.
Figure 1K:
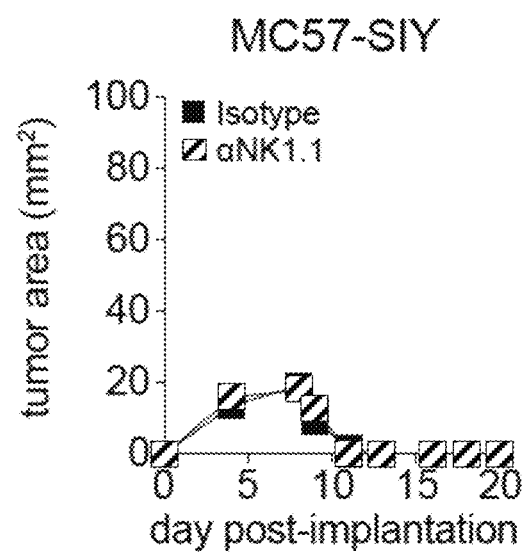
FIG. 1K shows tumor outgrowth ($mm^2$) of MC57-SIY in WT mice treated with anti-NK1.1 (striped squares) to deplete NK cells or an isotype control (black squares). Data are representative of two independent experiments with n=4 mice.

The initial analysis focused on the conventional DC compartment (defined as $CD45^+$ $MHCII^+$ $Ly6C^-$ $F4/80^-$ $CD11c^+$ $CD24^{hi}$) given its widely reported impact on anti-tumor immunity (5, 6, 8, 9). At day 7 post-tumor inoculation in wild-type (WT) C57BL/6 mice, a greater proportion of $CD103^+$ DC1 was detected in regressor tumors, whereas the DC compartment was skewed towards $CD11b^+$ DC2 in progressor tumors (FIGS. 1B-1C). This phenotype was conserved in immunodeficient $Rag2^{-/-}$ mice, suggesting that the presence of T cells had minimal impact on DC composition in the tumors (FIGS. 1D-1F). A time course study demonstrated that both DC1 and $CD8^+$ T cells were accumulating in regressor tumors, but these trends were not evident in progressor tumors (FIG. 1I). Although recent studies highlighted a role for natural killer (NK) cells in DC1 recruitment to the tumor (10, 11), it was found that antibody-mediated depletion of NK cells in WT mice had no effect on the numbers of DC1 that infiltrated the tumors (FIG. 1J), nor on the regression of MC57-SIY tumors (FIG. 1K).

Figure 1L:
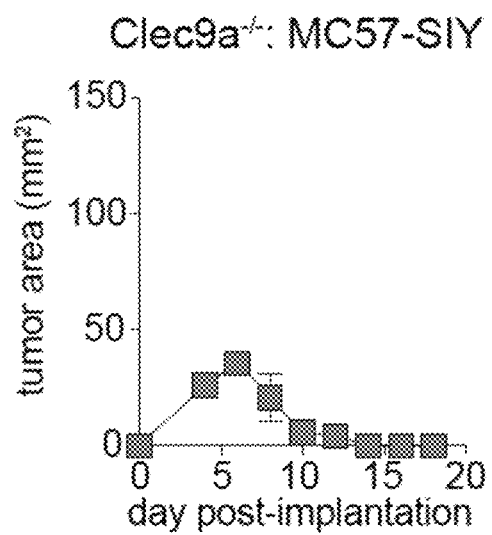
FIG. 1L shows tumor outgrowth ($mm^2$) of MC57-SIY in Clec9a−/− mice. Data are representative of two independent experiments with n=3 mice.
Figure 1M:
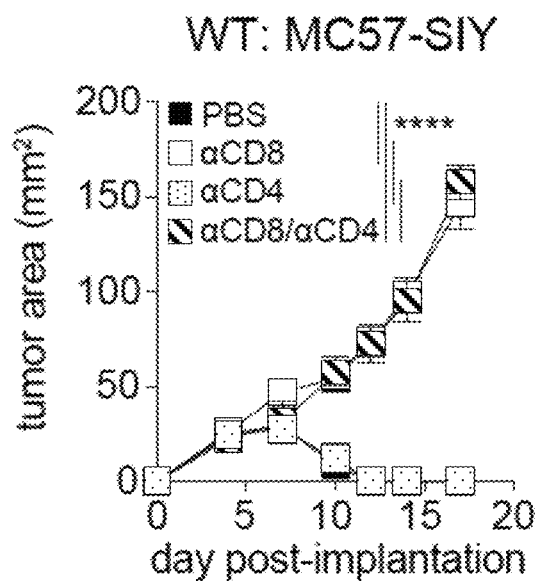
FIG. 1M shows tumor outgrowth ($mm^2$) of MC57-SIY in WT mice treated with anti-CD8 (white squares) to deplete CD8+ T cells, anti-CD4 (dotted squares) to deplete CD4+ T cells, anti-CD8 and anti-CD4 (striped squares) to deplete both CD8+ and CD4+ T cells, or PBS (black squares) as a control. Data are representative of two independent experiments with n=4 mice.
Figure 1N:
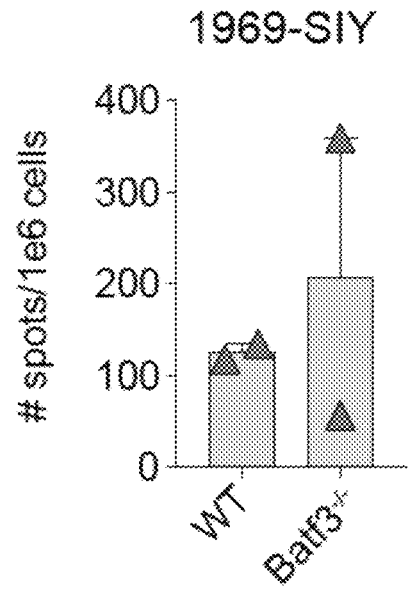
FIG. 1N shows ELISpot quantification of IFNγ-producing splenocytes from WT and Batf3−/− bearing 1969-SIY tumors at day 5 post-tumor inoculation. Data are pooled from individual mice (1969-SIY: WT n=2; Batf3−/− n=2) from one independent experiment.
Figure 1O:
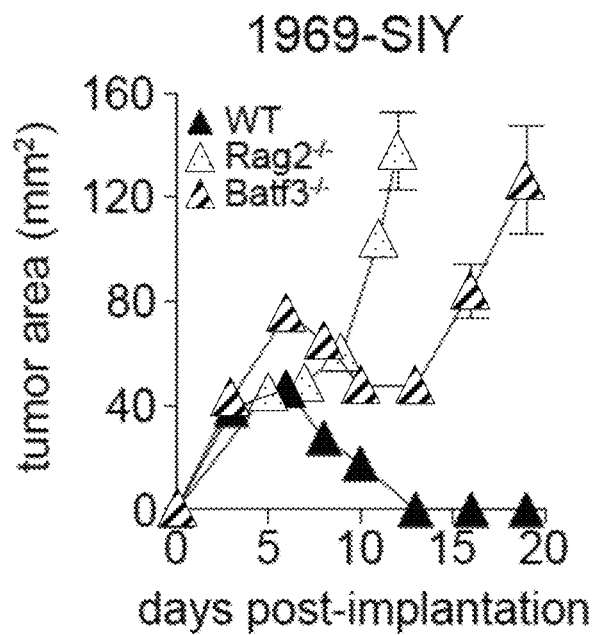

The observation of increased DC1 presence in regressor tumors prompted the evaluation of whether they were necessary for tumor rejection. The tumor lines were implanted into $Batf3^{-/-}$ mice, which lack conventional cross-presenting DC1 (12). Previous studies have suggested Batf3-driven DC1 as critically important for the induction of T cell priming responses (6, 12, 13). Consistent with the published data, the growth of progressor MC38-SIY tumors in $Batf3^{-/-}$ mice was accelerated compared to WT mice. By contrast, it was observed that regressor MC57-SIY tumors were rejected in $Batf3^{-/-}$ mice with similar kinetics as in WT mice (FIG. 1G). Using $Clec9a^{-/-}$ mice, a complementary model where DC1 are functionally impaired due to the genetic disruption of the endocytic receptor Clec9a (14), the observation that the regression of MC57-SIY tumors is independent of conventional cross-presenting DC1 was affirmed (FIG. 1L). One possibility bypassing the need for cross-presentation is tumor control by $CD4^+$ T cells (15). To assess whether regression of MC57-SIY is dependent on $CD8^+$ or $CD4^+$ T cells, each T cell subset was depleted alone or in combination and identified that tumor control was driven by $CD8^+$ T cells, making cross-presentation an essential component for the induction of anti-tumor immune responses (FIG. 1M). To further evaluate the anti-tumor T cell response induced against the tumor models, an IFNγ-Enzyme-Linked ImmunoSpot (IFNγ-ELISpot) assay was performed and it was confirmed that T cell responses against MC38-SIY tumors were completely ablated in $Batf3^{-/-}$ mice. In stark contrast, tumor-reactive T cell responses against MC57-SIY tumors were preserved in both $Batf3^{-/-}$ and $Clec9a^{-/-}$ mice, but were reduced by 57.9% and 39.2%, respectively, when compared to the responses in WT mice (FIG. 1H). To determine whether these observations were generalizable, the same experiments were performed with a second tumor model associated with productive anti-tumor T cell responses, the spontaneously rejected fibrosarcoma 1969-SIY (3). It was found that antigen-specific $CD8^+$ T cell responses were also preserved in $Batf3^{-/-}$ mice challenged with 1969-SIY tumor cells (FIG. 1N). However, in this model, $Batf3^{-/-}$ mice demonstrated only initial tumor control and ultimately failed to eliminate the tumor (FIG. 1O), suggesting that at least two antigen-presenting cell types are required for optimal anti-tumor immunity.

Previous studies indicate that engagement of the cGAS/STING pathway is critical for the activation of DC1 (16-18). Therefore, MC57-SIY cells were implanted into $STING^{-/-}$ mice and it was observed that immune clearance of the tumors was indeed independent of the cGAS/STING pathway (FIG. 2A), consistent with the observation that anti-tumor immunity against the regressor model is independent of DC1. Since a type-I-interferon (type-I-IFN) response is induced downstream of cGAS/STING signaling, it was assessed whether host type-I-IFN sensing was required for anti-tumor immunity against the regressor model. To this end, MC57-SIY cells were implanted into $Ifnar1^{-/-}$ mice and failed tumor control was subsequently observed (FIG. 2B), confirming the necessity of type-I-IFNs in tumor clearance. Collectively, these results indicate that anti-tumor immunity against MC57-SIY tumors is independent of Clec9a-mediated cross-presentation by Batf3-driven DC1 yet requires type-I-IFN sensing in a cGAS/STING-independent manner, and therefore, implies the presence of unknown cell type(s) mediating $CD8^+$ T cell activation.

Figure 2J:
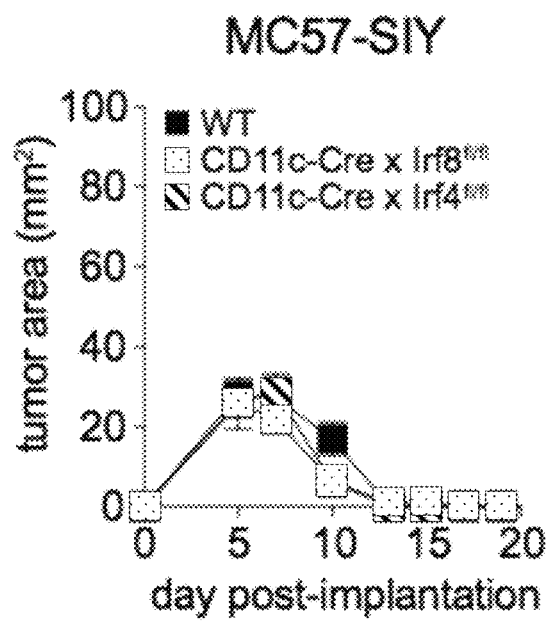

To identify the cell type(s) responsible for the induction of protective immunity against regressor MC57-SIY tumors in $Batf3^{-/-}$ mice, a functional ex vivo co-culture assay was established using naïve 2C TCR transgenic $CD8^+$ T cells that recognize the model antigen SIY on H-2K$^b$. Sorted antigen-presenting cells from SIY-expressing regressor tumors in WT and Batf3$^{-/-}$ mice were used to stimulate the T cells. Strikingly, only the CD11c$^+$ DC compartment, but not Ly6C$^+$ monocytes or F4/80$^+$ macrophages, was able to activate T cells (FIG. 2C). Specific depletion of CD11c$^+$ cells expressing diphtheria toxin receptor resulted in the complete ablation of antigen-specific T cell responses against regressor tumors (FIG. 2D), which provided additional evidence that T cell priming responses required CD11c$^+$ DC. To determine whether other classically described DC subsets, such as IRF4-driven DC2 and plasmacytoid DC (pDC), contributed to the anti-tumor immune response against MC57-SIY, the regressor line was implanted into mice lacking these subsets through CD11c+ DC-specific ablation of the transcription factors, IRF4 or IRF8, respectively. However, tumors regressed with similar kinetics as WT mice, suggesting that neither IRF4-driven DC2 nor pDC contributed significantly to the anti-tumor immune response (FIG. 2J).

Figure 2K:
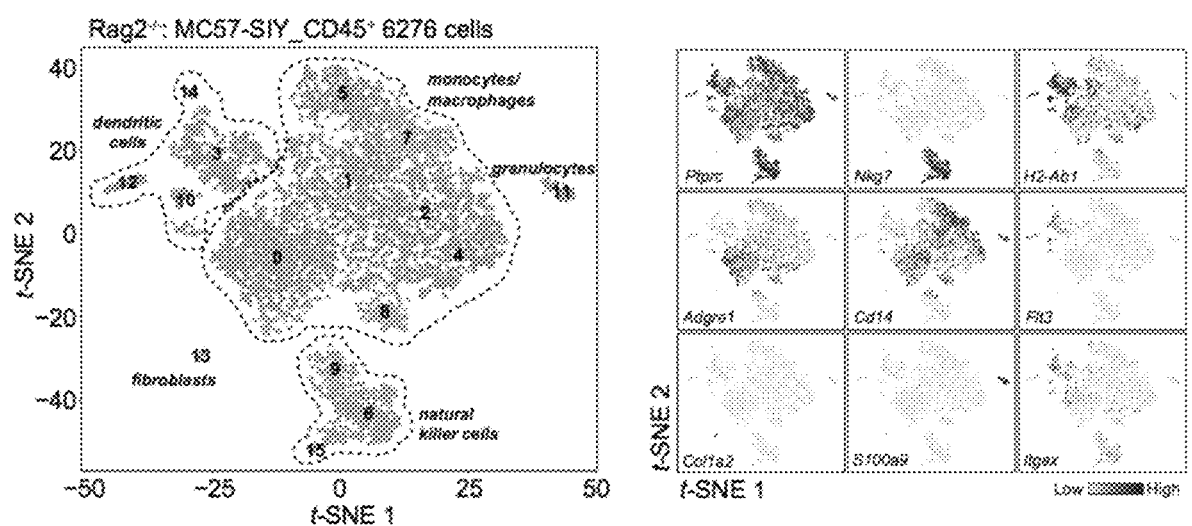

Given the limitations of the available experimental mouse models to determine which DC subset is mediating the anti-tumor immune response, it was next aimed to identify specific DC subsets using an unbiased approach. To do so, single-cell RNA-sequencing (scRNA-seq) of the CD45$^+$ immune infiltrate of regressor MC57-SIY tumors in Rag2$^{-/-}$ mice was performed (FIG. 2J, Table 1). Based on the expression of canonical DC marker genes (H2-Ab1, Flt3, Itgax) and the absence of marker genes corresponding to other lineages, a general DC cluster was identified that was then computationally isolated and re-analyzed at a higher resolution, leading to the identification of eight distinct DC clusters (FIG. 2E, FIG. 2K). The differentially expressed genes (DEG) of each DC cluster was mapped to the literature (19), and five canonically described subsets were identified: DC1 (cluster 3), DC2/monocyte-derived DC (moDC) (cluster 2), migratory DC (cluster 4), and two distinct pDC clusters (clusters 5 and 7) (FIG. 2F, Table 2). Intriguingly, the DEG analysis identified one cluster (cluster 1) comprising IFN-stimulated genes (ISG) but lacking significant transcriptional similarities to other conventional DC clusters. This cluster is referred to as 'ISG+ DC.'

Figure 2L:
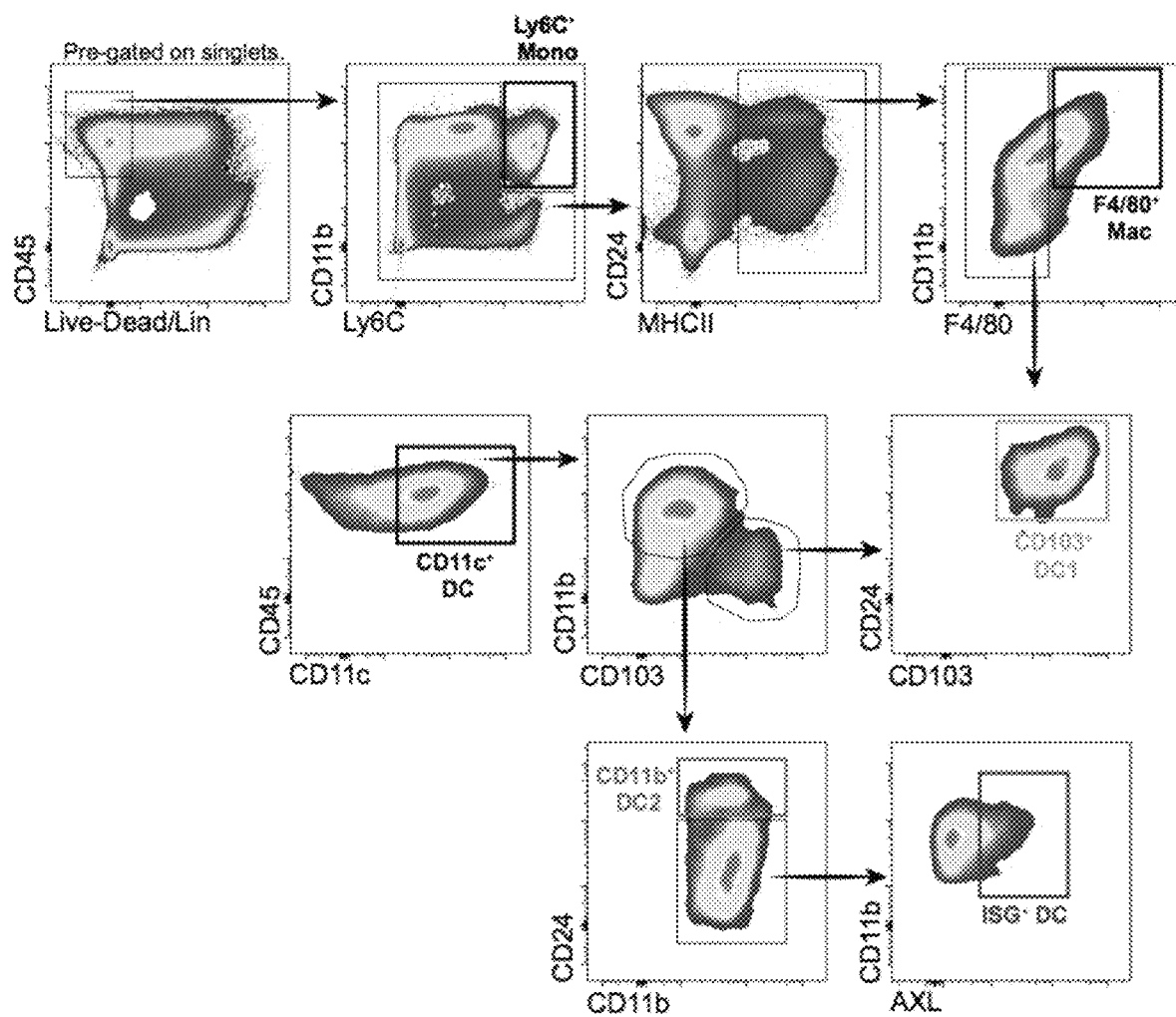
Figure 2M:
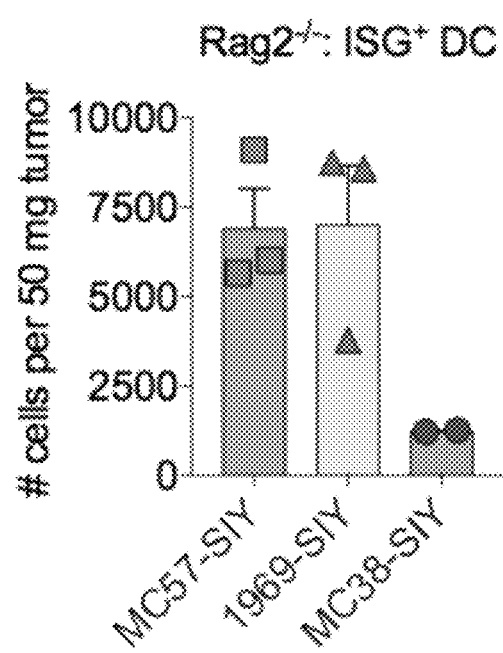

Given the knowledge that host sensing of type-I-IFNs is critical for immune-mediated clearance of MC57-SIY tumors (FIG. 2A), the contribution of ISG+ DC to the anti-tumor immune response was evaluated. In order to study the ISG+ DC cluster, Axl (an IFN-inducible receptor tyrosine kinase) (20) was identified as a surface-expressed marker that uniquely and significantly differentiated the ISG+ DC cluster from the remaining DC clusters (FIG. 2G; Table 3). AXL protein expression was validated within the CD11c+DC compartment of the regressor MC57-SIY tumor in Rag2$^{-/-}$ and Batf3' mice (FIGS. 2H-2I; FIG. 2L for representative gating strategy). Interestingly, both regressor tumor models were infiltrated with 5.6-fold (MC57-SIY) and 5.7-fold (1969-SIY) higher numbers of ISG$^+$ DC compared to progressor MC38-SIY tumors in Rag2$^{-/-}$ mice (FIG. 2M). Of note, a novel AXL-expressing DC subset (termed 'AS-DC') capable of activating T cells was recently identified in healthy human blood and peripheral tissues by scRNA-seq and mass cytometry, which is in line with the findings (21, 22). While AS-DC did not express a type-I-IFN response signature, this may reflect differences in DC activation states between healthy and diseased tissues. The ontogeny of AS-DC and ISG+ DC remains elusive.

Figure 3A:
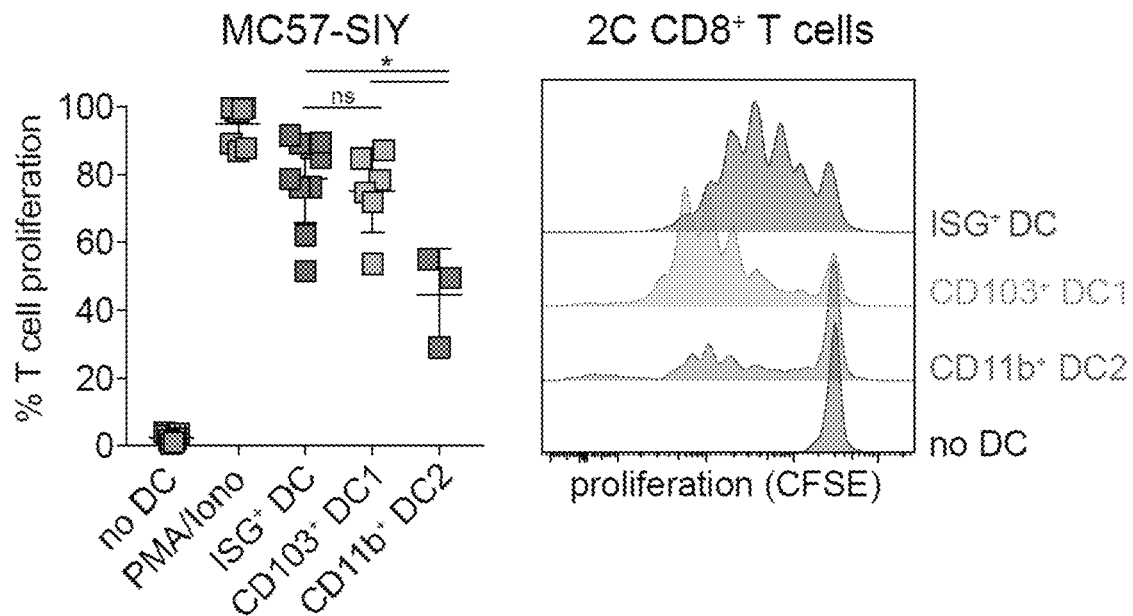
FIGS. 3A-3K show that ISG+ DC activate CD8+ T cells by cross-dressing with tumor-derived peptide-MHC complexes, leading to protective systemic immunity.
Figure 3B:
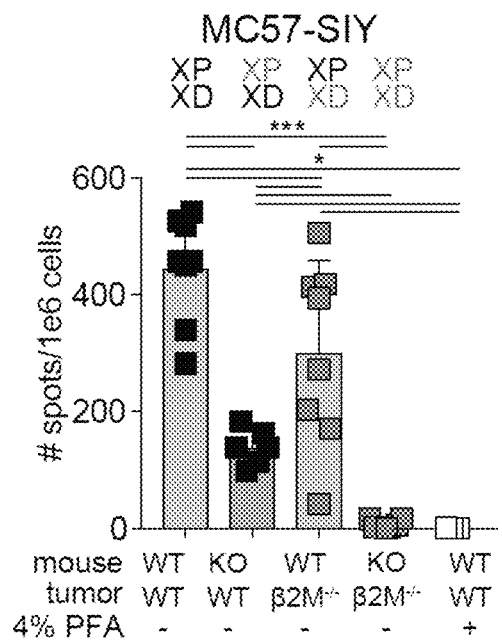
Figure 3C:
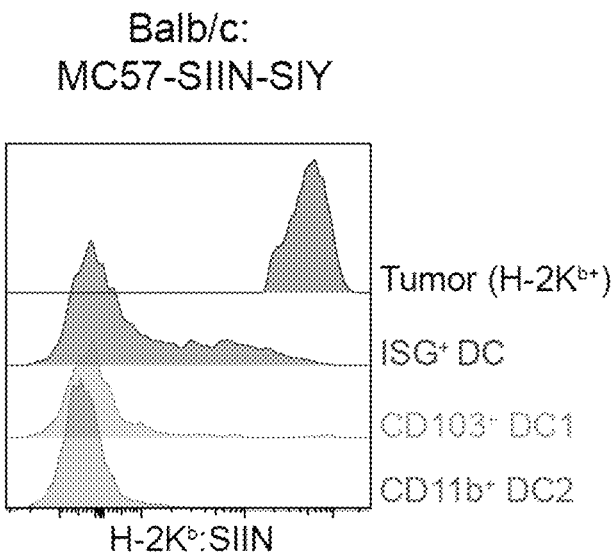
Figure 3D:
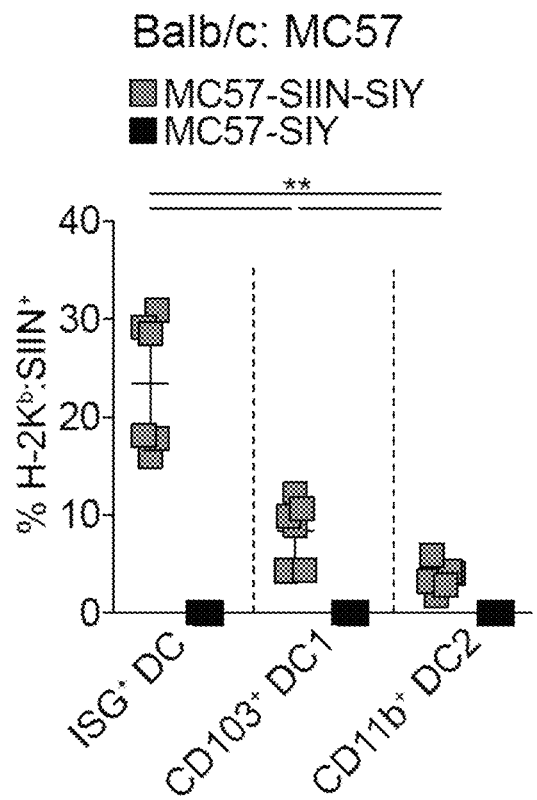
Figure 3E:
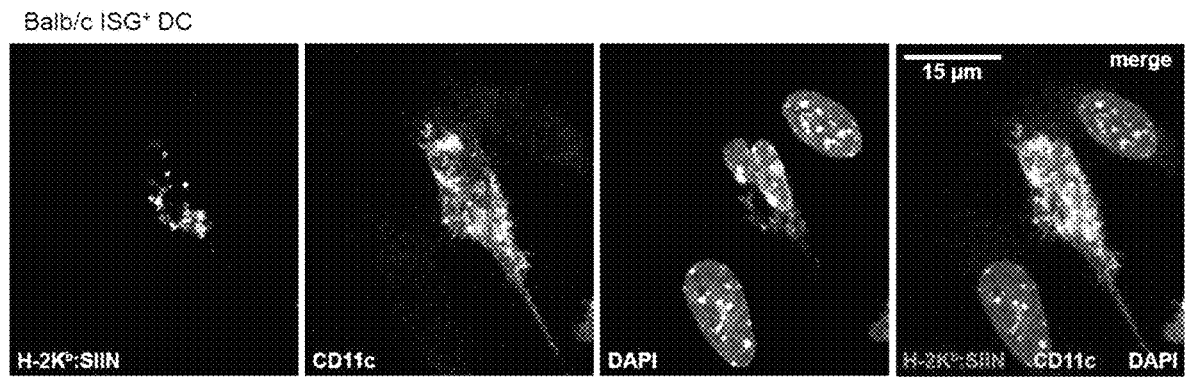

To elucidate whether ISG+DC from regressor MC57-SIY tumors were functional, their stimulatory ability was tested using the previously established ex vivo co-culture assay. It was observed that ISG+ DC could induce similar levels of T cell proliferation as DC1 (FIG. 3A). Interestingly, while similar results were observed with ISG+ DC from regressor 1969-SIY tumors (FIG. 3H), the rare ISG+ DC from progressor MC38-SIY tumors failed to induce T cell proliferation (FIG. 3I).

Next, it was sought to identify the mechanism by which ISG DC from regressor tumors were activating CD8$^+$ T cells. Three routes of antigen presentation used by DC to activate CD8$^+$ T cells have been reported: (1) direct presentation of intracellular antigens (exclusive to pathogen-infected DC); (2) cross-presentation of exogenously-derived antigens (i.e. dead-cell-debris from Clec9a-mediated endocytosis); and (3) cross-dressing with pre-formed functional peptide-MHC complexes derived from adjacent cells through membrane exchange. Although studies have described the phenomenon of cross-dressing between virally infected and non-infected DC (23), it is unknown whether it occurs between DC and non-immune cells, such as tumor cells in the TME. Given that the previous results excluded canonical cross-presentation in ISG DC-mediated T cell activation (FIGS. 1G-1H), cross-dressing was evaluated as the mechanism of antigen-presentation by ISG DC. MC57-SIY tumor cells lacking MHC class I expression were generated through CRISPR-Cas9-mediated disruption of the β-2 microglobulin (β2M) gene and its outgrowth was validated in immunocompetent mice (FIG. 3J). When MHC class I-deficient MC57-SIY tumor cells were implanted into WT mice, a 34.5% reduction was observed in tumor-reactive T cell responses compared to implantation of the MHC class I-proficient line into WT mice, which was fully attributed to cross-presentation (FIG. 3B). When MHC class I-deficient tumor cells were implanted into Batf3$^{-/-}$ mice, however, complete loss (98.4% reduction) of antigen-specific T cell responses was observed (FIG. 3B), indicating that cross-dressing is partially responsible for the induction of tumor-reactive T cells against the regressor MC57-SIY tumor in WT mice. To test for the possibility that the antigen-specific T cell responses were due to direct priming by tumor cells, the MHC class I-proficient tumor cells were fixed prior to implantation in Batf3$^{-/-}$ mice and it was observed that this failed to induce antigen-specific T cell responses (FIG. 3B).

A complementary approach was used to validate whether ISG DC are uniquely qualified for cross-dressing. The regressor MC57 tumor line was engineered to express the ovalbumin-derived model T cell antigen SIINFEKL (SIIN) in addition to SIY, which enabled the detection of surface H-2K$^b$:SIIN complexes using antibody staining. Following implantation of MC57-SIIN-SIY (H-2K$^{b+}$) into Balb/c mice (H-2K$^{d+}$), transferred H-2K$^b$:SIIN complexes were detected on the surface of Balb/c ISG DC but not appreciably on other DC subsets (FIGS. 3C-3D). Immunofluorescence microscopy studies of sorted Balb/c ISG DC co-cultured with MC57-SIIN-SIY tumor cells ex vivo confirmed the transfer of intact peptide-MHC complexes between tumor cells and ISG DC (FIG. 3E). The route of transfer appears to occur through cellular vesicles (FIG. 3K), consistent with a recent report on DC-to-DC transfer of tumor-derived antigens (24). Collectively, the data indicate that ISG DC from regressor tumors can activate CD8$^+$ T cells through means independent of conventional cross-presentation by cross-dressing with tumor-derived peptide-MHC complexes.

Figure 3F:
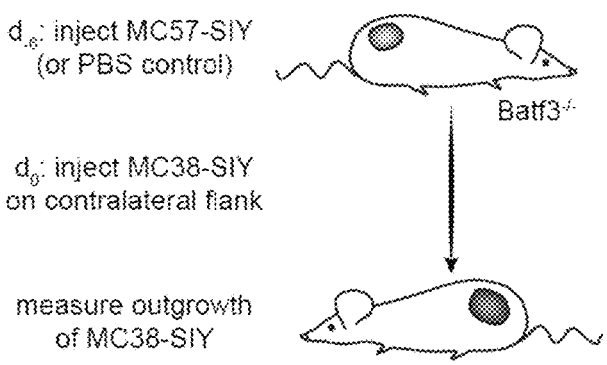
Figure 3G:
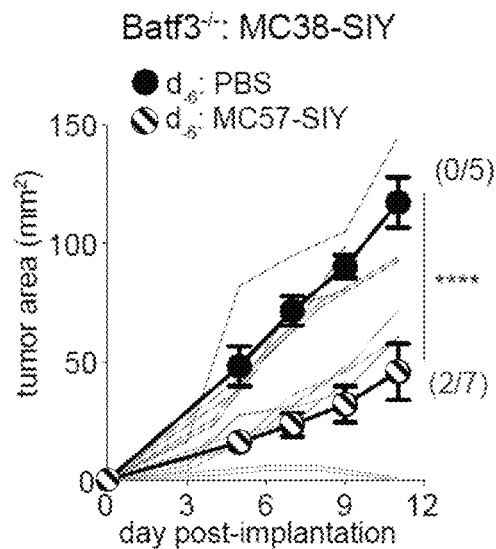
Figure 3H:
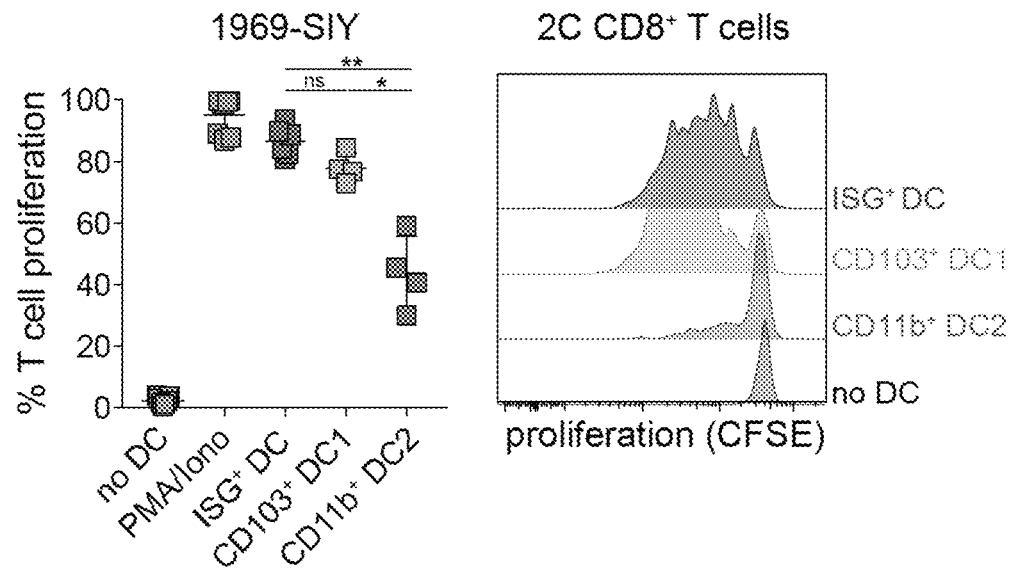
Figure 3I:
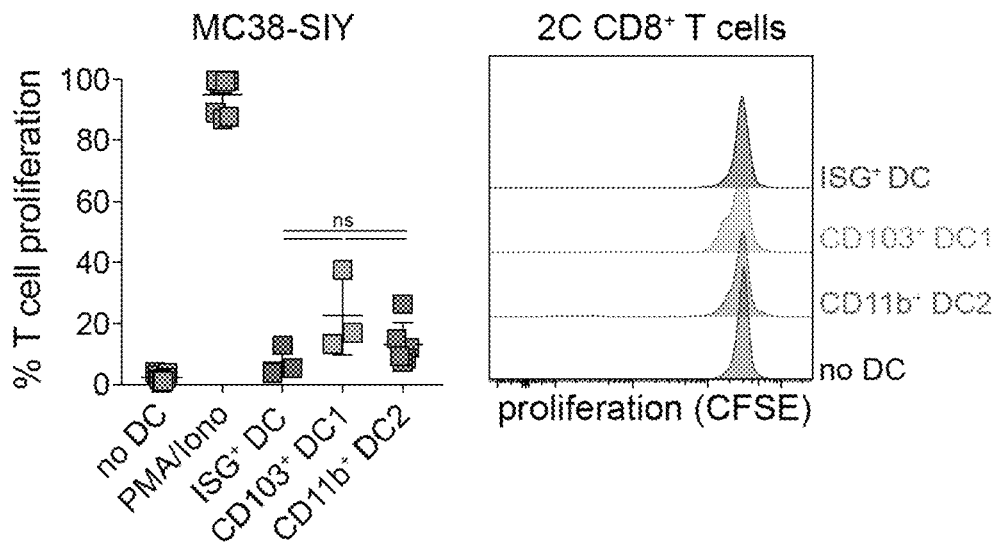
Figure 3J:
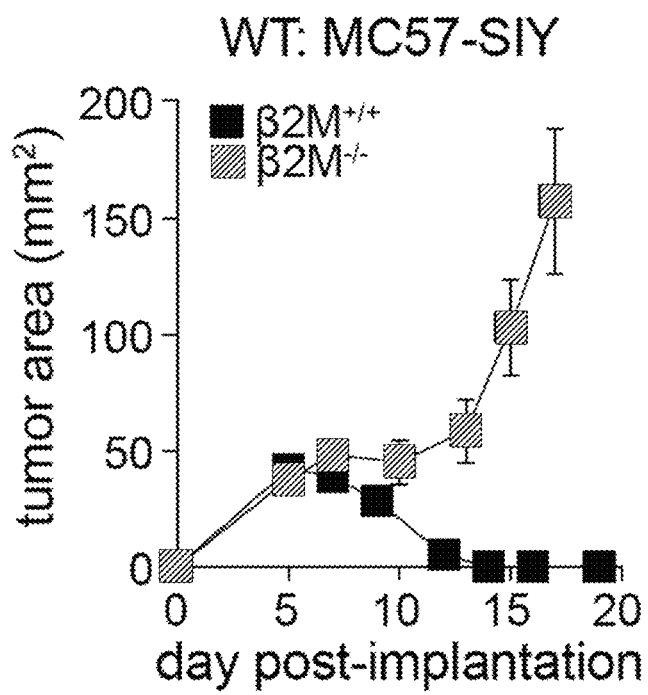
Figure 3K:
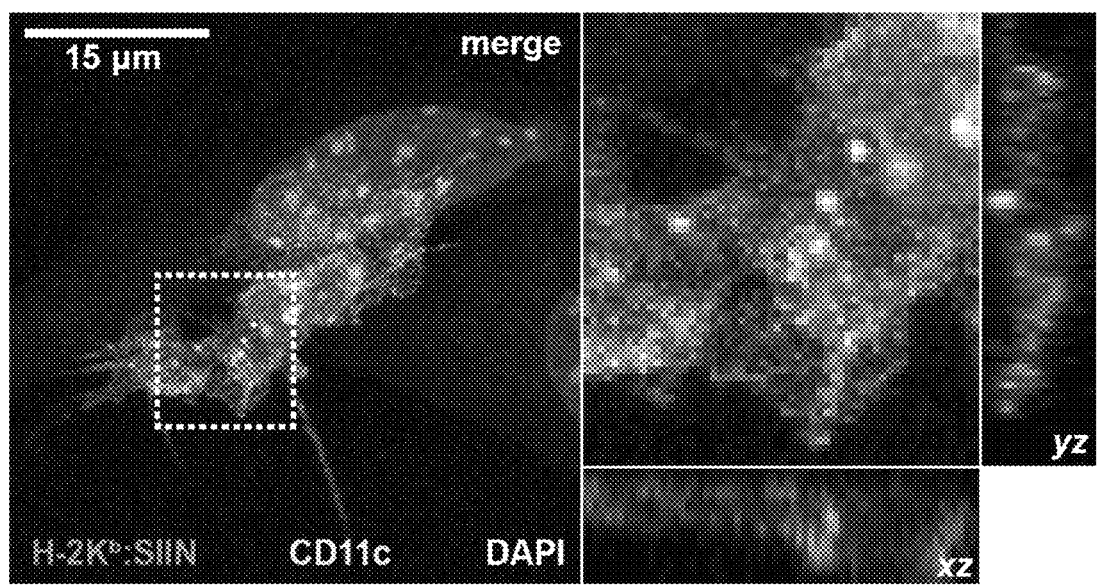

To assess whether CD8$^+$ T cells primed by cross-dressing ISG DC could induce systemic immunity in the absence of canonical cross-presentation, MC57-SIY tumor cells were pre-inoculated into Batf3$^{-/-}$ mice and evaluated outgrowth of progressor MC38-SIY tumor cells implanted on the contralateral flank (FIG. 3F). Indeed, it was observed that CD8$^+$ T cells induced by cross-dressing ISG DC were able to control the growth of MC38-SIY tumors (FIG. 3G), with a 64.1% decrease in average tumor burden compared to control. Taken together, these data demonstrate that ISG DC are a functionally distinct subset of DC that can induce strong antigen-specific T cell responses by cross-dressing with tumor-derived peptide-MHC complexes, resulting in protective systemic anti-tumor immunity.

To understand how ISG DC were sensing regressor tumors, the scRNA-seq dataset were analyzed for the expression of pattern recognition receptors among the DC clusters. In agreement with the literature, the DC1 cluster expressed high Tlr3 transcripts and one of the pDC clusters expressed high Tlr9 transcripts, which are involved in the sensing of endocytic dsRNA or ssRNA, respectively (FIG. 4A). In contrast to the cluster-specific TLR expression, STING, the sensor for cGAMP was found to be broadly expressed in all clusters. Intriguingly, the ISG DC cluster highly expressed transcripts involved in cytosolic sensing of dsRNA (Ddx58, Dhx58, Ifih1) (FIG. 4A). To determine whether regressor MC57-SIY tumors were producing dsRNA species, bone marrow (BM)-derived DC was in vitro differentiated from WT mice using GM-CSF and then stimulated with MC57-SIY tumor-conditioned media. Compared to unstimulated controls, the tumor-conditioned supernatant induced the upregulation of core type-I-IFN response genes in BM-DC (FIG. 4B). These responses were blunted to varying degrees using BM-DC from Mavs$^{-/-}$ mice, suggesting that the type-I-IFN response observed in BM-DC was in part driven by cytosolic MAVS-dependent sensing of dsRNA present in the tumor supernatant (FIG. 4B). Of note, it was observed that the regressor MC57-SIY tumor-conditioned supernatant was able to induce significantly higher levels of type-I-IFN response genes in WT BM-DC compared to the progressor MC38-SIY tumor-conditioned supernatant (FIG. 4H), suggesting that MC57-SIY tumors produced more dsRNA species than MC38-SIY tumors. Indeed, recent studies demonstrated that tumors can produce and accumulate more dsRNA species through the loss of RNA-editing enzymes, such as ADAR1 (25, 26), or through the reactivation of endogenous retroviruses (27).

The lower levels of immune stimulatory dsRNA in progressor MC38-SIY tumors in combination with the data that ISG+ DC were largely absent (FIG. 2L) and non-functional (FIG. 3I) in progressor tumors prompted the interrogation of whether insufficient levels of dsRNA precluded the activation of ISG+ DC. In an attempt to overcome this deficiency, MC38-SIY tumor cells were exogenously coated with Poly (I:C), a synthetic dsRNA analog, and implanted this line into WT or Batf3$^{-/-}$ mice to evaluate tumor-reactive T cell responses by IFNγ-ELISpot. It was observed that the addition of Poly(I:C) was able to rescue antigen-specific T cell responses against progressor MC38-SIY tumors in Batf3$^{-/-}$ mice, restoring 45.0% of the priming responses observed in WT mice (FIG. 4C). It was confirmed that the rescued T cell responses were mediated by cross-dressing DC, since no restoration was observed when MHC class I-deficient MC38-SIY tumor cells were used. Furthermore, implantation of Poly(I:C)-coated fixed tumor cells failed to induce any antigen-specific T cell responses, thus excluding the possibility of direct priming by the tumor (FIG. 4C). A careful examination of the immunofluorescence microscopy slides for FIG. 3E revealed that while some Balb/c ISG$^+$ DC harbored H-2K$^b$:SIIN$^+$ intracellular vesicles (FIG. 3K), ISG$^+$ DC that carried H-2K$^b$:SIIN$^+$ DAPI$^+$ intracellular vesicles were also detected (FIG. 4I). These observations suggested that ISG$^+$ DC could be exposed to tumor-derived nucleic acid species via the acquisition of tumor-antigen-coated vesicles, which implies a link between cytosolic dsRNA-sensing and cross-dressing.

Analyses of human tumors indicate that accumulation of tumor-derived dsRNA correlates with cytotoxic immune activity (26-28). To determine whether ISG$^+$ DC in human tumors would predict a T cell-inflamed phenotype, a pan-cancer analysis was performed using The Cancer Genome Atlas (TCGA) database correlating the ISG$^+$ DC signature with a previously defined 160-gene T cell-inflamed signature (29). Indeed, a significant correlation in 30 out of the 31 solid tumor types tested was observed (FIG. 4D). Furthermore, in four cancer types (CESC: Cervical Squamous Cell Carcinoma and Endocervical Adenocarcinoma, LIHC: Liver Hepatocellular Carcinoma, SARC: Sarcoma, SKCM: Skin Cutaneous Melanoma), both the T cell-inflamed and the ISG$^+$ DC signature correlated with significantly improved five-year survival. Within the TCGA cohort for LIHC and SARC, patient stratification using the ISG+DC signature resulted in increased significance of survival difference between the two patient groups, suggesting an ability to better identify patient sub-populations (FIG. 4J). Taken together, these analyses demonstrate that ISG DC are translationally relevant and are associated with the T cell-inflamed TME.

A novel dsRNA-sensing DC subset was identified, characterized by an ISG signature that can activate T cells by cross-dressing with tumor-derived peptide-MHC complexes, leading to protective systemic immunity. It was further demonstrated that exogenous addition of a dsRNA analog can induce cross-dressing DC in MC38-SIY tumors and rescue T cell responses in Batf3$^{-/-}$ mice. While ISG$^+$ DC alone were sufficient for the spontaneous regression of MC57-SIY tumors, therapeutically induced ISG DC alone were unable to fully drive the rejection of MC38-SIY tumors. It is therefore likely that the concerted action of multiple DC subsets sensing different tumor-derived danger signals is required for optimal anti-tumor immunity (FIG. 4E). The data suggests that different DC subsets vary in their ability to stimulate T cells and likely induce different T cell phenotypes. Engaging the functionally relevant DC subsets that associate with strong, functional T cell responses, such as ISG$^+$ DC, provides a therapeutic opportunity to boost anti-tumor immunity.

Materials and Methods

Mice

Wild-type (WT) C57BL/6, WT Balb/c, and Rag2$^{-/-}$ C57BL/6 mice were obtained from Taconic Biosciences. Batf3$^{-/-}$, Clec9a$^{-/-}$, Cd11c-Cre, CD11c-DTR, STING$^{-/-}$, Ifnar1$^{-/-}$, Irf4$^{fl/fl}$, Irf8$^{fl/fl}$, and Mavs$^{-/-}$ mice were obtained from Jackson Laboratories. Irf4$^{fl/fl}$ and Irf8$^{fl/fl}$ mice were crossed to CD11c-Cre mice to ablate Irf4 and Irf8, respectively, in the CD11c$^+$ compartment. For CD11c-Cre crosses, F1 and F2 offspring only were used, since more wide-spread deletion was observed if mice were bred to be homozygous for CD11c-Cre. All mice were housed and bred under specific pathogen free (SPF) conditions at the Koch Institute animal facility except for the Ifnar1−/− mice, which were housed and bred at the Koch Biology Building animal facility. For experiments with Ifnar1−/− mice, only female mice, 6-8 weeks old, were used, and controls were transferred into the Koch Biology Building facility and co-housed for an extended period of time. For all other strains, mice were gender-matched and age-matched to be 6-12 weeks old at the time of experimentation. All experimental animal procedures were approved by the Committee on Animal Care (CAC/IACUC) at MIT.

Generation of Cerulean-SIIN-SIY Expression Vector

The pLV-EF1α-IRES-puro vector (Addgene #85132) was digested with BamHI and EcoRI restriction enzymes (NEB) to linearize the vector. The cerulean-SIIN-SIY insert was generated using the Cerulean-N1 vector (Addgene #54742) linked to a codon-optimized sequence of the SIINFEKL (SIIN) and SIYRYYGL (SIY) peptides. The insert was then cloned into the linearized pLV-EF1α-IRES-puro vector (final construct referred to as 'pLV-EF1α-cerulean-SIIN—SIY-IRES-puro') using the In-Fusion cloning kit (Takara Bio), amplified, and sequenced for accuracy.

Tumor Cell Lines and Outgrowth

Parental and SIY-GFP expressing MC38 colon carcinoma, MC57 fibrosarcoma, and 1969 fibrosarcoma tumor cell lines were a gift from the Gajewski laboratory at The University of Chicago. MC57 and MC38 tumor lines stably expressing cerulean-SIIN-SIY were generated by lentiviral transduction of the parental tumor lines with the pLV-EF1α-cerulean-SIIN-SIY-IRES-puro construct and puromycin (Gibco) selected. Expression was further confirmed by flow staining for cerulean+ cells.

Tumor cell lines were cultured at 37° C. and 5% CO2 in DMEM (Gibco) supplemented with 10% FBS (Atlanta Biologicals), 1% penicillin/streptomycin (Gibco), and 1×HEPES (Gibco). Tumor cells were harvested by trypsinization (Gibco) and washed 3 times with PBS (Gibco). Cells were resuspended in PBS, and $2\times10^6$ tumor cells were injected subcutaneously into the flanks of mice. For experiments with pattern recognition receptor (PRR) agonist coating, $2\times10^6$ tumor cells were resuspended with 50 µg naked Poly(I:C) HMW (InvivoGen), DMXAA (InvivoGen), or Pam2CSK4 (InvivoGen) in PBS and injected subcutaneously into the flanks of mice. All PRR agonists were added to cells without a transfection reagent. For experiments with fixed tumor cells, the cells were fixed with 4% paraformaldehyde (Electron Microscopy Sciences) for 10 minutes at RT, washed twice and resuspended with PBS, and $2\times10^6$ tumor cells were injected subcutaneously into the flanks of mice. Tumor area measurements (calculated as length× width) were collected 2-3 times a week until the endpoint of the study. Data not shown but available upon request—Details on experimental cohorts, the raw data, as well as the power calculations for all tumor outgrowth experiments.

In Vivo Depletion of Cytolytic Cells

To deplete Natural Killer (NK) cells, 50 µg of anti-NK1.1 (Bio X Cell) or an isotype control antibody (Bio X Cell) was injected intraperitoneally 2 days prior to tumor implantation and subsequently every 3-4 days thereafter for the duration of the study. To deplete T cells, 200 µg of anti-CD8 (Bio X Cell), anti-CD4 (Bio X Cell), combined anti-CD8/anti-CD4, or an equal volume of PBS was injected intraperitoneally 2 days prior to tumor implantation, and 100 µg was subsequently injected every 3-4 days thereafter for the duration of the study.

Generation of CRISPR Knockout Cell Lines

The px459-Cas9-puro vector (Addgene #62988) was digested with the BbsI restriction enzyme (NEB) to linearize the vector. CRISPR guides targeting exon 2 of murine β-2 microglobulin (β2M) were designed using Benchling. The CRISPR guides used to target exon 2 of murine β-2 microglobulin (132M) were as follows:

```
                                            (SEQ ID NO: 1)
sgβ2M-1:   5'-AGTATACTCACGCCACCCAC-3';

(SEQ ID NO: 2)
sgβ2M-2:   5'-CGTATGTATCAGTCTCAGTG-3';

(SEQ ID NO: 3)
sgβ2M-3:   5'-GGATTTCAATGTGAGGCGGG-3';

(SEQ ID NO: 4)
sgβ2M-4:   5'-GCTTCCCATTCTCCGGTGGG-3'.
```

Forward and reverse oligos (Integrated DNA Technologies) for each guide were annealed together with a standard annealing protocol, cloned into the px459-Cas9-puro vector by T4 ligation (NEB), amplified, and sequenced for accuracy. The forward primers used were as follows:

```
                                            (SEQ ID NO: 5)
18S:       5'-GCTGGAATTACCGCGGCT-3';

(SEQ ID NO: 6)
Ddx58:     5'-AGACCACAAACTTGGAGAGTCAC-3';

(SEQ ID NO: 7)
Irf7:      5'-CTTCAGCACTTTCTTCCGAGA-3';

(SEQ ID NO: 8)
Irf3:      5'-ATGGCTGACTTTGGCATCTT-3';

(SEQ ID NO: 9)
Ifnb:      5'-CACAGCCCTCTCCATCAACTA-3';

(SEQ ID NO: 10)
Isg15:     5'-GAACAAGTCCACGAAGACCAG-3';

(SEQ ID NO: 11)
Cxcl10:    5'-GCTGCCGTCATTTTCTGC-3';

(SEQ ID NO: 12)
Oas1:      5'-GTGCTGCCAGCCTTTGAT-3';

(SEQ ID NO: 13)
Mx1:       5'-GCACCTGAAAGCCTACTACCA-3'.
```

The reverse primers used were as follows:

```
                                            (SEQ ID NO: 14)
18S:       5'-CGGCTACCACATCCAAGGAA-3';

(SEQ ID NO: 15)
Ddx58:     5'-GCGGTCTTAGCATCTCCAAC-3';

(SEQ ID NO: 16)
Irf7:      5'-TGTAGTGTGGTGACCCTTGC-3';

(SEQ ID NO: 17)
Irf3:      5'-CGTCCGGCTTATCCTTCC-3';

(SEQ ID NO: 18)
Ifnb:      5'-CATTTCCGAATGTTCGTCCT-3';

(SEQ ID NO: 19)
Isg15:     5'-GCAGCTCCTTGTCCTCCAT-3';

(SEQ ID NO: 20)
Cxcl10:    5'-TCTCACTGGCCCGTCATC-3';

(SEQ ID NO: 21)
Oas1:      5'-TGAGGATGGCATAGATTCTGG-3';

(SEQ ID NO: 22)
Mx1:       5'-GGATGAAGTACTGGATAATCAGAGG-3'.
```

MC57-SIY and MC38-SIY tumor lines were transiently transfected with the pooled guides and selected with puromycin for 48 hours. Cells surviving puromycin treatment were expanded, and the ablation of β2M was confirmed by sequencing, western blot for β2M, and/or flow staining for surface MHC class I expression.

IFNγ—ELISpot

ELISpot plates (EMD Millipore) were coated overnight at 4° C. with anti-IFNγ (BD Biosciences). Plates were washed and blocked with DMEM supplemented with 10% FBS, 1% penicillin/streptomycin, and 1×HEPES for 2 hours at room temperature (RT). Spleens were harvested from mice at day 5 or day 7 post-tumor inoculation and mashed through a 70 µm filter with a 1 mL syringe plunger to generate a single cell suspension. Red blood cells were lysed with 500 µL of ACK Lysing Buffer (Gibco) on ice for 2 minutes. Splenocytes were washed 3 times with chilled PBS and 1×106 cells were assayed per well in the presence or absence of 160 nM SIY peptide or 100 ng/mL PMA (Sigma-Aldrich) and 1 µg/mL ionomycin (Sigma-Aldrich) as a positive control. Plates were developed the next day using the BD mouse IFNγ-ELISpot kit, following manufacturer's protocol.

Generation of CD11c-DTR and β2M–/– Bone Marrow Chimeras and DC Depletion

Host WT C57BL/6 mice were irradiated with 500 rad, allowed to recover for 3 hours, and subsequently irradiated again with 550 rad. The next day, bone marrow was harvested from the femur and tibia of donor mice (CD11c-DTR or β2M–/– mice), washed and resuspended in PBS, and 1×10$^7$ cells were injected retro-orbitally into the irradiated host mice. A period of 8 weeks was allowed for engraftment prior to the start of experiments.

For depletion of DC in CD11c-DTR bone marrow chimeras, 500 ng diphtheria toxin (DT) (Sigma-Aldrich) (or an equivalent volume of PBS for control mice) was injected intraperitoneally 2 days prior to tumor implantation and subsequently injected every other day thereafter for 7 days.

Tumor Dissociation

Tumors were dissected from mice and collected in 500 µL RPMI (Gibco) containing 250 µg/mL Liberase (Sigma-Aldrich) and 50 µg/mL DNase (Sigma-Aldrich). Tumors were minced with dissection scissors and incubated for 20 minutes at 37° C. for enzymatic digestion. Following the digestion, tumor pieces were mashed through a 70 µm filter with a 1 mL syringe plunger to generate a single cell suspension. The dissociated cells were washed 3 times with chilled PBS containing 1% FBS and 2 mM EDTA (Gibco).

Flow Cytometry and Cell Sorting

Prior to staining, cells were washed with FACS staining buffer (chilled PBS containing 1% FBS and 2 mM EDTA). Cells were stained for 15 minutes on ice with eBioscience Fixable Viability Dye eFluor 780 to distinguish live and dead cells and with anti-CD16/CD32 (clone 93, BioLegend) to prevent non-specific antibody binding. Cells were then washed once and cell surface proteins were stained for 30 minutes on ice with fluorophore-conjugated antibodies at a 1:200 or a 1:400 dilution (Table 5). For stains that used biotinylated primary antibodies, cells were washed twice and subsequently stained with a streptavidin-conjugated fluorophore for 30 minutes on ice. Following the surface staining, cells were washed twice and analyzed directly or fixed with IC Fixation Buffer (eBioscience) for 20 minutes at RT for analysis the next day. Flow cytometry sample acquisition was performed on a BD LSRFortessa cytometer, and the collected data was analyzed using FlowJo v10.5.3 software (TreeStar). For cell sorting, the surface staining was performed as described above under sterile conditions, and cells were acquired and sorted into RPMI containing 10% FBS, 1% penicillin/streptomycin, and 1×HEPES using a BD FACSAria III sorter.

TABLE 5

Antibody clones.
ANTIBODIES

| | Clone | Vendor | Catalog # | Dilution |
|---|---|---|---|---|
| Flow Cytometry and Immunofluorescence Microscopy | | | | |
| anti-mouse AXL (FITC) | MAXL8DS | eBioscience | 53-1084-82 | 1:200 |
| anti-mouse AXL (PE-Cy7) | MAXL8DS | eBioscience | 25-1084-82 | 1:200 |
| anti-mouse β2M | EPR21752-214 | abcam | ab218230 | 1:200 |
| anti-mouse CD103 (APC) | 2E7 | eBioscience | 17-1031-82 | 1:200 |
| anti-mouse CD11b (PE-CF594) | M1/70 | BD Horizon | 562287 | 1:400 |
| anti-mouse CD11c (BV421) | N418 | BioLegend | 117330 | 1:400 |
| anti-mouse CD11c (AF488) | N418 | BioLegend | 117311 | 1:400 |
| anti-mouse CD16/32 | 93 | BioLegend | 101330 | 1:100 |
| anti-mouse CD19 (APC-Cy7) | 6D5 | BioLegend | 115530 | 1:400 |
| anti-mouse CD24 (BUV737) | M1/69 | BD Horizon | 565308 | 1:400 |
| anti-mouse CD24 (BV605) | M1/69 | BioLegend | 101827 | 1:400 |
| anti-mouse CD3e (APC-Cy7) | 17A2 | BioLegend | 100222 | 1:200 |
| anti-mouse CD3e (BV711) | 17A2 | BioLegend | 100241 | 1:200 |
| anti-mouse CD40 (BV711) | 23-Mar | BD Optibuild | 740700 | 1:200 |
| anti-mouse CD44 (AF700) | IM7 | BioLegend | 103026 | 1:400 |
| anti-mouse CD45 (BUV395) | 30-F11 | BD Horizon | 564279 | 1:400 |
| anti-mouse CD45 (BV786) | 30-F11 | BioLegend | 564225 | 1:400 |
| anti-mouse CD62L (BV605) | MEL-14 | BioLegend | 104437 | 1:400 |
| anti-mouse CD63 (APC) | NVG-2 | BioLegend | 143905 | 1:400 |
| anti-mouse CD8α (BV711) | 53-6.7 | BioLegend | 100759 | 1:400 |
| anti-mouse CD8α (BUV395) | 53-6.7 | BD Horizon | 563786 | 1:400 |
| anti-mouse CD80 (PE-Cy7) | 16-10A1 | BioLegend | 104733 | 1:200 |
| anti-mouse CD86 (AF700) | PO3 | BioLegend | 105122 | 1:200 |
| anti-mouse F4/80 (PE-Cy7) | BM8 | BioLegend | 123113 | 1:400 |
| anti-mouse F4/80 (APC-Cy7) | BM8 | BioLegend | 123118 | 1:400 |
| anti-mouse H-2Kb/H-2Db (FITC) | 28-8-6 | BioLegend | 114606 | 1:200 |
| anti-mouse H-2Kb (PE-Cy7) | AF6-88.5 | BioLegend | 116520 | 1:200 |
| anti-mouse IFNγ (PE-CF594) | XMG1.2 | BioLegend | 562303 | 1:200 |
| anti-mouse Ly6C (PE) | HK1.4 | BioLegend | 128007 | 1:400 |
| anti-mouse Ly6C (APC-Cy7) | HK1.4 | BioLegend | 128026 | 1:400 |
| anti-mouse MHCII (AF700) | M5/114.15.2 | eBioscience | 56-5321-80 | 1:400 |

TABLE 5-continued

| Antibody clones. ANTIBODIES | | | | |
|---|---|---|---|---|
| anti-mouse NK1.1 (APC-Cy7) | PK136 | BioLegend | 108724 | 1:200 |
| anti-mouse PD-1 (PE-Cy7) | RMP1-30 | BioLegend | 109110 | 1:200 |
| anti-mouse Siglec H (BV605) | 440c | BD Optibuild | 747673 | 1:400 |
| anti-mouse SIINFEKL/H-2Kb (biotinylated) | 25-D1.16 | eBioscience | 13-5743-81 | 1:200 |
| mouse IgG1κ isotype control (biotinylated) | P3.6.2.8.1 | eBioscience | 13-4714-85 | 1:200 |
| SIY pentamer (PE) | | ProImmune | F1803-2B-D | 1:100 |
| streptavidin (BV711) | | BioLegend | 405241 | 1:400 |
| fixable viability eFluor 780 | | eBioscience | 65-0865-18 | 1:2000 |
| Western Blot | | | | |
| anti-mouse CD81 | D5O2Q | Cell Signaling Technology | 10037S | 1:1000 |
| goat anti-rabbit IgG (IRDye 800CW) | polyclonal | LI-COR | 926-32211 | 1:25,000 |

| In Vivo | Clone | Vendor | Catalog # | Concentration |
|---|---|---|---|---|
| anti-mouse NK1.1 | PK136 | Bio X Cell | BP0036 | 50 µg per dose |
| mouse IgG2a isotype control | C1.18.4 | Bio X Cell | BP0085 | 50 µg per dose |
| anti-mouse CD8 | 2.43 | Bio X Cell | BE0061 | 200 µg per dose |
| anti-mouse CD4 | GK1.5 | Bio X Cell | BE0003 | 200 µg per dose |

Ex Vivo DC-T Cell Co-Culture Assay

To obtain antigen-presenting cell compartments or specific DC subsets, cells were FACS-sorted from tumors as described above. To obtain CFSE-labeled CD8⁺ T cells, naïve 2C TCR transgenic CD8⁺ T cells were isolated from spleen and lymph nodes of 2C or OTI TCR transgenic C57BL/6 mice using a CD8⁺ T cell isolation kit (Miltenyi Biotec), following manufacturer's instructions. Isolated CD8⁺ T cells were washed twice with PBS and stained with 2.5 µM CFSE (eBioscience) in PBS for 8 minutes at 37° C. or 5 µM CellTrace Violet (Thermo Fisher Scientific) in PBS for 20 min at 37° C. The dye was then quenched with FBS, and the cells were washed 3 times with RPMI containing 10% FBS. For the coculture, $5 \times 10^5$ CFSE-labeled 2C TCR transgenic CD8⁺ T cells and $1 \times 10^5$ sorted antigen-presenting cells or DCs (5:1 T cell-DC ratio) were mixed and added to each well of a V-bottom tissue culture-treated 96-well plate in RPMI supplemented with 10% FBS, 1% penicillin/streptomycin, 1×HEPES, 1×MEM Non-Essential Amino Acids (Gibco), and 1× β-mercaptoethanol (Gibco). The cells were cultured at 37° C. and 5% $CO_2$ for 72 hours at which point T cell proliferation was measured by CFSE-dye dilution via flow cytometry as a proxy for T cell activation. Expression of T cell activation markers and cytokines was also assessed by flow staining as described.

Single Cell RNA-Sequencing and Analysis

Live intratumoral CD45⁺ cells from C57BL/6 Rag2⁻/⁻ mice bearing MC57-SIY tumors at day 7 post-tumor implantation were FACS-sorted as described above. Sorted cells were washed twice and resuspended at a final concentration of $1 \times 10^3$ cells/µL in chilled PBS containing 0.04% BSA (Thermo Fisher Scientific). The cellular suspension was submitted to the Whitehead Institute Genome Technology Core for cDNA library preparation. Briefly, single cells were encapsulated into droplets using the 10× Genomics Chromium Controller, and the cDNA library was prepared using the Chromium Single Cell 3' Reagent Kits v2 (10× Genomics) following manufacturer's instructions. The resultant cDNA library was then sequenced by the MIT BioMicro Center using an Illumina HiSeq2000. Demultiplexing, mapping to the mm10 genome, and barcode and UMI counting were performed with 10× Genomics Cell Ranger v3.0.1, and the resultant count matrix was loaded into Seurat v2.3.4 (30) for further processing. Cells expressing less than 200 genes or more than 6000 genes, as well as cells expressing more than 25% mitochondrial transcripts were excluded, which left 6276 cells for downstream analysis. The data was normalized using the Seurat Log Normalize function with the default scale factor of $10^4$. The data was subsequently scaled using the Seurat ScaleData function and latent variables (number of UMIs and percentage of mitochondrial transcripts) were regressed out. The Seurat FindVariableGenes function was used to identify approximately 3000 variable genes for principal component analysis (PCA). The Seurat FindClusters function, which implements the shared nearest neighbor (SNN) clustering algorithm, identified 16 clusters using the top 13 PCA components and a resolution of 1.2. The Seurat FindAllMarkers function was used to identify the differentially expressed genes (DEG) for each cluster compared to all other clusters with default parameters that required genes to be expressed in more than 25% of cells with a minimum 0.5-fold difference. To identify clusters, the DEG lists of the clusters were manually compared to reports in the literature.

DC Population Analysis and ISG+ DC Surface Marker Identification

To examine DC at higher resolution, cell clusters that expressed H2-Ab1 and Itgax and/or Flt3 were computationally isolated using the Seurat SubsetData function (yielding 824 cells). The Seurat analysis as described above was performed on these isolated cells, which led to the identification of eight DC clusters using approximately 5000 variable genes, the top 10 PCA components, and a resolution of 0.8. To identify clusters, the DEG lists of the DC clusters were manually cross-referenced to the DC signatures recently reported in the literature (19). To identify surface markers for cluster 1 (ISG+ DC) for downstream functional studies, the DEG list was filtered for cluster 1 with the requirement marker genes must (1) have a minimum avg_log FC threshold of 0.5; (2) have an adjusted p-value $<5 \times 10^{-2}$; (3) be unique to cluster 1; (4) have an enrichment score <0.5, defined as the ratio of percent expression in all other clusters (pct.2) vs. percent expression in cluster 1 (pct.1), (5) be surface-expressed; and (6) have a commercially available antibody. Data for FIG. 2G was generated by using the Seurat FindAllMarkers function without any filtering parameters and reporting the resultant avg log FC value for Axl per cluster.

H-2K$^b$:SIIN Cross-Dressing Assay

2×10$^6$ MC57-SIIN-SIY or SIIN-negative control MC57-SIY (H-2K$^{b+}$) tumor cells were implanted into the flanks of WT Balb/c mice (H-2K$^{d+}$). On day 5 post-tumor inoculation, surface flow staining for H-2K$^b$:SIIN on the DC infiltrate of dissociated tumors was performed. Refer to "Flow Cytometry and Cell Sorting" for details on the general staining protocol. For surface staining of the transferred complex by flow cytometry, biotin-H-2K$^b$:SIIN (or biotin-mouse IgG1κ isotype control) was added to Fc-blocked cells at a 1:200 dilution in FACS staining buffer and incubated on ice for 30 min in the dark. Cells were washed twice and subsequently stained with a streptavidin-BV711 secondary at a 1:400 dilution for 30 min on ice in the dark. Cells were then washed twice and fixed with IC Fixation Buffer (eBioscience) prior to analysis on a BD LSRFortessa cytometer.

Cross-Dressing Visualization by Immunofluorescence Microscopy

MC57-SIY (H-2K$^{b+}$) tumor cells were implanted into the flanks of WT Balb/c mice (H-2K$^{d+}$). On day 5 post-tumor inoculation, ISG DC were sorted from dissociated tumors, as described previously. Coverslips in 6-well non-TC-treated plates were coated with 500 µL Poly-L-Lysine (Gibco) for 10 minutes at RT, washed 3 times with sterile water, and air-dried. Sorted ISG$^+$ DC and MC57-SIIN-SIY tumor cells at a 1:1 ratio, or separately as controls, were plated on the coverslips and cultured for 24 hours at 37° C. and 5% $CO_2$ in RPMI supplemented with 10% FBS, 1% penicillin/streptomycin, 1×HEPES, 1×MEM Non-Essential Amino Acids, and 1×β-mercaptoethanol. After 24 hours, cells were fixed with 4% paraformaldehyde for 20 minutes at RT and gently permeabilized with 0.1% Triton X-100 (Sigma-Aldrich) for 10 minutes at RT. Coverslips were then blocked with 2.5% bovine serum albumin (Research Products International) and anti-CD16/CD32 (clone 93, BioLegend) for 20 minutes at RT. Primary antibodies at 1:200 or a 1:400 dilution (Table 5) were added to the coverslips and incubated for 1 hour at RT. Coverslips were then washed 3 times with Dulbecco's PBS with calcium and magnesium (Gibco) for 5 minutes each. Secondary antibodies (Table 5) were added at 1:400 dilution and incubated for 20 minutes at RT. Following washes, coverslips were mounted onto glass slides using ProLong Gold Antifade with DAPI (Invitrogen). Slides were dried overnight, sealed with clear nail polish, and imaged using a Leica TCS SP8 confocal laser scanning microscope.

Collection of Unenriched Tumor-Conditioned Supernatant

Tumor supernatant was collected when flasks containing MC38-SIY or MC57-SIY tumor cells reached 100% confluency. Tumor supernatant was centrifuged at 500 g for 3 minutes to pellet cell debris and subsequently filtered through a 0.45 µm PVDF syringe filter (EMD Millipore). The resultant cell-free tumor supernatant was aliquoted and stored at −20° C.

Collection of EV and EV-Depleted Cleared Supernatant

Cell cultures used for EV isolation were grown in EV-depleted media prepared by ultracentrifugation of FBS for 18 hr at 120,000 g. Tumor supernatant for EV purification was harvested when flasks containing MC38-SIY or MC57-SIY tumor cells reached 100% confluency (typically at 48-72 hr after initial passage). Serial high-speed ultracentrifugation using a Beckman Coulter Optima XE ultracentrifuge was performed to enrich for EV from the supernatant. Briefly, approximately 250 mL of tumor-conditioned supernatant was centrifuged for 300 g for 10 min, 2,000 g for 10 min, and 10,000 g for 30 min to remove cellular debris. The supernatant was then centrifuged at 100,000 g for 1.5 hr to pellet EV. Immediately following this spin, the EV-depleted supernatant was collected as "cleared supernatant," and used directly for functional assays or aliquoted and stored at −20° C. The EV pellet was resuspended in chilled PBS and centrifuged for 100,000 g for 2 hr to remove traces of media. The resultant EV pellet was either used directly for in vitro assays, lysed directly for Western Blot, or lysed in TRIzol Reagent (Invitrogen) and stored at −80° C.

Generation and Culture of BM-Derived DC

Bone marrow (BM) was harvested from the femur and tibia of mice by flushing the bones with RPMI using a 1 mL syringe. Cells were passed through a 70 µm filter, washed twice with PBS, and cultured at a density of 1.5×10$^6$ cells/mL in RPMI supplemented with 10% FBS, 1% penicillin/streptomycin, 1×HEPES, 1×MEM Non-Essential Amino Acids, 1×β-mercaptoethanol, and 40 ng/mL recombinant mouse GM-CSF (BioLegend) for 7 days at 37° C. and 5% $CO_2$. BM-DCs at day 7 of culture were either used directly in assays or frozen in 10% DMSO in FBS and stored in liquid nitrogen.

BM-DC ISG Induction Assay

On day 7, BM-DCs were harvested, re-plated at 3×10$^6$ cells per well of a 6-well tissue culture-treated plate, and cultured with (1) 2 mL of tumor-conditioned unenriched supernatant; (2) EV isolated from tumor-conditioned supernatant, resuspended in 2 mL of fresh complete DMEM media; or (3) 2 mL of EV-depleted cleared supernatant for 24 hr. Following the incubation, BM-DC were washed and lysed with RLT Buffer (Qiagen) for subsequent RNA extraction.

RNA Isolation and qRT-PCR

RNA was isolated using the Qiagen RNeasy Kit (Qiagen) or Zymo MicroRNA Kit (Zymo Research), following manufacturer's instructions. Extracted RNA was quantified by NanoDrop and 250-1000 ng of RNA was reverse transcribed into cDNA using the Applied Biosystems Reverse Transcriptase Kit, following manufacturer's instructions. For each qRT-PCR reaction, 1 µL of the cDNA was assayed using the Applied Biosystems SYBR Green PCR Master Mix with defined primer sets for each target gene. Reactions were run on the StepOne Real-Time PCR System (Applied Biosystems) and the expression level was calculated as $2^{-\Delta CT}$, where $\Delta CT$ is the difference between the CT values of the target gene and 18S.

EV and Cellular Protein Extraction and Western Blot

Protein lysates from tumor cells or EV were prepared with RIPA Lysis Buffer supplemented with a 1× protein inhibitor cocktail (Roche). Samples were loaded with SDS-PAGE sample loading buffer without a reducing agent. For each sample, 16 µg of protein was loaded on a 12.5% SDS-PAGE gel and transferred to PVDF membranes (Sigma-Aldrich). Membranes were blocked with Odyssey Blocking Buffer (LI-COR) for 30 min at RT, followed by an overnight incubation at 4° C. with primary antibody at a 1:1000 dilution (Table 5) in blocking buffer. Membranes were subsequently washed three times with 1×Tris-buffered saline supplemented with 0.1% TWEEN-20 (Sigma-Aldrich) (TBS-T) and incubated for 1 hr at RT with a fluorophore-conjugated secondary antibody (Table 5) at a 1:10,000 dilution in blocking buffer. Membranes were washed three times with TBS-T and imaged using the Odyssey CLx Imaging System (LI-COR).

EU Transfer Imaging

As stated previously, cell cultures used for EV isolation were grown in EV-depleted media prepared by ultracentrifugation of FBS for 18 hr at 120,000 g. MC57-SIY tumor cells were either left unlabeled (control) or labeled with 225 µM 5-Ethynyl Uridine (EU) for 16 hr at 37° C., rinsed twice with PBS, and re-supplied with fresh media. After 48 hr of culture, tumor-conditioned supernatant was harvested and EV was enriched by serial high-speed ultracentrifugation as described. Isolated EU-labeled and unlabeled EV were incubated with $3 \times 10^5$ WT BM-DC plated in a μ-Slide 8 Well chambered slide (Ibidi) for 16 hr at 37° C. EU was visualized using the Click-iT RNA Alexa Fluor 594 Imaging Kit (Invitrogen), following manufacturer's instructions. Additional markers, CD63 and CD11c (Table 5), were stained following the immunofluorescence microscopy protocol described previously. Chamber slides were then filled with PBS and imaged using a Leica TCS SP8 confocal laser scanning microscope.

EU and CD63 Colocalization Analysis

All image analyses were performed using Fiji (ImageJ) v2.0.0. For each cell image, EU and CD63 channels were merged, and a maximum intensity Z-projection ranging from 15-24 Z-layers was used for subsequent analysis. The "Segmented Line" tool was used to draw connecting lines between $CD63^+$ puncta within a single cell. This line was drawn to include all potentially positive areas, as well as cell background, while excluding the nucleus. The intensities of the CD63 and EU channels along the drawn line was plotted using the "Plot Profile" tool and the raw data was extracted. These data were then plotted as histograms using GraphPad Prism. Signal thresholds were set for each cell manually based on background intensities. Any signal above the background threshold was counted as $CD63^+$, $EU^+$, or $CD63^+ EU^+$. To calculate the frequency of $EU^+$ or $EU^-$ EV as a proportion of all $CD63^+$ EV for a given cell, the number of $CD63^+ EU^+$ or $CD63^+ EU^-$ peaks was divided by the total count of $CD63^+$ peaks for a given cell.

EV RNA Extraction

As stated previously, cell cultures used for EV isolation were grown in EV-depleted media prepared by ultracentrifugation of FBS for 18 hr at 120,000 g. At 48-72 hr of culture, MC57-SIY tumor supernatant was harvested and EV was enriched by serial high-speed ultracentrifugation as described. Pelleted EV were resuspended in 100 μL of TRIzol Reagent (Invitrogen). EV preps from five independent harvests were pooled, mixed, and split into two groups. Total RNA was extracted from each group using the Directzol RNA Miniprep Plus Kit (Zymo Research) and eluted in 50 μL nuclease-free water. One group was treated with RNase III (Ambion), following manufacturer's instructions, and the other group remained untreated (control). RNA from both groups was subsequently re-purified using the RNeasy MiniElute Cleanup Kit (Qiagen), eluted in 100 μL nuclease-free water, and directly assayed in the dsRNA ELISA.

dsRNA ELISA

Nunc MaxiSorp flat-bottom 96-well plates were coated with 4 μg/mL anti-dsRNA K1 antibody (English and Scientific Consulting) overnight at 4° C. Plates were blocked with 1% bovine serum albumin (BSA), washed three times with PBS containing 0.1% TWEEN-20 (Sigma-Aldrich), and samples and control standards (100 μL/well, duplicate wells) were added and incubated overnight at 4° C. For control standards, Poly(I:C) (Invivogen) was serially diluted in nuclease-free water, ranging from 25 ng/mL to 0 ng/mL. Plates were then washed three times, and 4 μg/mL of a biotinylated anti-dsRNA J2 antibody (English and Scientific Consulting) was added for 2 hr at RT. Plates were subsequently washed three times, and streptavidin-HRP (BD Biosciences) was added at a 1:100 dilution and incubated for 30 min at RT. Plates were thoroughly washed five times, and 50 μL of 1-Step Ultra TMB-ELISA Substrate Solution (Pierce) was added to the wells. The reaction was stopped with an equal volume of Stop Solution (Thermo Fisher Scientific) and the absorbance at 450 nm was read using a Tecan M200 Infinite Pro Microplate Reader.

Systemic Immunity Assay

To induce systemic immune responses, $Batf3^{-/-}$ mice were implanted subcutaneously in the flank with $2 \times 10^6$ MC57-SIY tumor cells or an equal volume of PBS as a control. After 6 days, $2 \times 10^6$ MC38-SIY tumor cells were implanted on the contralateral flanks of the mice, and tumor outgrowth was measured as previously described.

Human Clinical Data Analyses

Genomic data for cancer patient samples were obtained from The Cancer Genome Atlas (TCGA, Cancer Genome at NIH website). This included RNA-sequencing gene expression profiles of primary tumor patient samples across all TCGA cancer types, as well as associated clinical data. A 35-gene ISG+ DC cluster signature was derived using marker genes from murine scRNA-seq analysis filtered for significance ($p<0.05$) and fold change ($FC>1.5$). Genes that were found to be markers for other clusters ($p<0.05$) were filtered out. Murine gene names were translated to human nomenclature (Gene Names website). Additionally, three DC marker genes were added to the signature (HLA-DQB1, ITGAX, FLT3) for specificity. This 35-gene signature consisted of H2-Ab1, Itgax, Flt3, Znfx1, Zbp1, Trim30c, Trafd1, Sp110, Slfn9, Samhd1, Rsad2, Rnf213, Pttg1, Phf11d, Phf11a, Parp14, Nmi, Iigp1, Igtp, Ifit3b, Ifih1, Ifi209, Gbp7, Gbp3, Fam26f, Endod1, Eif2ak2, Dhx58, Ddx60, Cmpk2, Cd86, Cd69, Ccl4, AA467197 and 1600014C10Rik. Individual TCGA sample expression profiles (RNA-seq) per cancer type were scored with the ISG cluster signature using ssGSEA (31, 32). Samples were stratified according to their standardized score (z-score) into top and bottom sets (z-score $\geq 1$ and z-score $<-1$, respectively). To visualize scores across all cancer types, scaled scores (0 to 1 range) were plotted (FIG. 4D) using stylistic elements and logic borrowed from Maftools (33). Top and bottom sets described earlier were highlighted on these plots. Kaplan-Meier survival analyses were conducted between these sets of patients corresponding to the two sample sets. The log-rank test was used to assess significance. The 160-gene T cell-inflamed signature (29) was similarly used to stratify samples within each TCGA cancer type. Overlap between the top scoring samples (z-score $\geq 1$) in the T cell-inflamed signature ranking versus the ISG+ DC signature ranking was assessed using the hypergeometric test. All plots and statistical analyses were implemented in R ("R-project" website) and all survival analyses and were conducted using the survival package in R.

Statistical Analysis

All statistical analyses were performed using GraphPad Prism (GraphPad). All data are shown as mean±s.e.m. Unless stated otherwise, statistical analyses were performed with MWU test (for comparison of two groups) or 2-way ANOVA (for multiple comparisons) with $*p<0.05$, $p<0.005$, $*p<0.001$, $****p<0.0001$.

REFERENCES

1. A. Ribas, J. D. Wolchok, Cancer immunotherapy using checkpoint blockade. *Science*. 359, 1350-1355 (2018).
2. P. C. Tumeh, et al. PD-1 blockade induces responses by inhibiting adaptive immune resistance. *Nature*. 515, 568-571 (2014).

3. J. B. Williams, et al. The EGR2 targets LAG-3 and 4-1BB describe and regulate dysfunctional antigen-specific CD8+ T cells in the tumor microenvironment. *J Exp Med.* 214, 381-400 (2017).
4. L. M. McLane, et al. CD8 T cell exhaustion during chronic viral infection and cancer. *Annual Review of Immunology.* 37, 457-495 (2019).
5. S. Spranger, et al. Tumor-residing Batf3 dendritic cells are required for effector T cell trafficking and adoptive T cell therapy. *Cancer Cell.* 31, 711-723 (2017).
6. M. L. Broz, et al. Dissecting the tumor myeloid compartment reveals rare activating antigen presenting cells critical for T cell immunity. *Cancer Cell.* 26, 638-652 (2014).
7. H. Salmon, et al. Expansion and activation of CD103+ dendritic cell progenitors at the tumor site enhances tumor responses to therapeutic PD-L1 and BRAF inhibition. *Immunity.* 44, 924-938 (2016).
8. S. Spranger, et al. Melanoma-intrinsic β-catenin signaling prevents anti-tumor immunity. *Nature.* 523, 231-235 (2015).
9. E. W. Roberts, et al. Critical Role for CD103+/CD141+ dendritic cells bearing CCR7 for tumor antigen trafficking and priming of T cell immunity in melanoma. *Cancer Cell.* 30, 324-336 (2016).
10. J. P. Böttcher, et al. NK cells stimulate recruitment of cDC1 into the tumor microenvironment promoting cancer immune control. *Cell.* 172, 1022-1037 (2018).
11. K. C. Barry, et al. A natural killer-dendritic cell axis defines checkpoint therapy-responsive tumor microenvironments. *Nature Medicine.* 24, 1178-1191 (2008).
12. K. Hildner, et al. Batf3 deficiency reveals a critical role for CD8α+ dendritic cells in cytotoxic T cell immunity. *Science.* 322, 1097-100 (2008).
13. M. B. Fuertes, et al. Host type I IFN signals are required for antitumor CD8+ T cell responses through CD8{alpha}+ dendritic cells. *J Exp Med.* 208, 2005-2016 (2011).
14. S. Zelenay, et al. The dendritic cell receptor DNGR-1 controls endocytic handling of necrotic cell antigens to favor cross-priming of CTLs in virus-infected mice. *J Clin Invest.* 122, 1615-1627 (2012).
15. D. Mumberg, et al. CD4+ T cells eliminate MHC class II-negative cancer cells in vivo by indirect effects of IFN-γ. *PNAS.* 96, 8633-8638 (1999).
16. M. B. Fuertes, et al. Type I interferon response and innate immune sensing of cancer. *Trends in Immunology.* 34, 67-73 (2013).
17. S. R. Woo, et al. STING-dependent cytosolic DNA sensing mediates innate immune recognition of immunogenic tumors. *Immunity.* 41, 830-842 (2014).
18. X. Liu, et al. Dual targeting of innate and adaptive checkpoints on tumor cells limits immune evasion. *Cell Reports.* 24, 2101-2111 (2018).
19. R. Zilionis, et al. Single-cell transcriptomics of human and mouse lung cancers reveals conserved myeloid populations across individuals and species. *Immunity.* 50, 1317-1334 (2019).
20. E. T. Schmid, et al. AXL receptor tyrosine kinase is required for T cell priming and antiviral immunity. *eLIFE.* 5, e12414 (2016).
21. A. C. Villani, et al. Single-cell RNA-seq reveals new types of human blood dendritic cells, monocytes, and progenitors. *Science.* 356, eaah4573 (2017).
22. M. Alcántara-Hernández, et al. High-dimensional phenotypic mapping of human dendritic cells reveals interindividual variation and tissue specialization. *Immunity.* 47, 1037-1050 (2017).
23. L. M. Wakim, M. J. Bevan. Cross-dressed dendritic cells drive memory CD8+ T-cell activation after viral infection. *Nature.* 471, 629-632, (2012).
24. E. W. Roberts, et al. Tumors exploit dedicated intracellular vesicles to program T cell responses. bioRxiv. 691873 (2019).
25. J. J. Ishizuka, et al. Loss of ADAR1 in tumors overcomes resistance to immune checkpoint blockade. *Nature.* 5, 43-48 (2019).
26. H. Liu, et al. Tumor-derived IFN triggers chronic pathway agonism and sensitivity to ADAR loss. *Nature Medicine.* 25, 95-102 (2019).
27. K. B. Chiappinelli, et al. Inhibiting DNA methylation causes an interferon response in cancer via dsRNA including endogenous retroviruses. *Cell.* 162, 974-986 (2015).
28. M. S. Rooney, et al. Molecular and genetic properties of tumors associated with local immune cytolytic activity. *Cell.* 160, 48-61 (2015).
29. S. Spranger, et al. Density of immunogenic antigens does not explain the presence or absence of the T-cell-inflamed tumor microenvironment in melanoma. *PNAS.* 113, E7759-E7768 (2016).
30. A. Butler, et al. Integrating single-cell transcriptomic data across different conditions, technologies, and species. *Nature Biotechnology.* 26, 411-420 (2018).
31. A. Subramanian, et al. Gene set enrichment analysis: a knowledge-based approach for interpreting genome-wide expression profiles. *Proc Natl Acad Sci USA.* 102, 15545-15550 (2006).
32. D. A. Barbie, et al. Systematic RNA interference reveals that oncogenic KRAS-driven cancers require TBK1. *Nature.* 462, 108-112 (2009).
33. A. Mayakonda, et al. Maftools: efficient and comprehensive analysis of somatic variants in cancer. *Genome Res.* 28, 1747-1756 (2018).

EQUIVALENTS

The foregoing written specification is considered to be sufficient to enable one ordinarily skilled in the art to practice the invention. The present invention is not to be limited in scope by examples provided, since the examples are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

What is claimed is:

1. A method of treating a subject having a solid cancer, comprising administering, to a subject having a malignant tumor characterized as lacking or having low levels of interferon-stimulated gene signature dendritic cells (ISG+DCs), an ISG+DC inducing agent in an effective amount, wherein said ISG+DCs are:
   (a) positive for one or more markers selected from the group consisting of Cxcl10, Ifit3, Rsad2/Viperin, Ifit1, Ifit1bl1, Ifit2, Isg15, Ifit3b, Usp18, and Ifi204; and
   (b) negative for one or more markers selected from the group consisting of Batf3, IRF8, XCR1, and BDCA-3.

2. The method of claim 1, further comprising identifying the subject having a malignant tumor characterized as lacking or having low ISG+DC level.

3. The method of claim 1, wherein ISG+DC levels are detected based on mRNA expression.

4. The method of claim 3, wherein the mRNA expression is obtained using bulk-RNA-seq or scRNAseq.

5. The method of claim 1, wherein ISG+DCs are detected based on protein profile.

6. The method of claim 5, wherein the protein profile is a cell surface protein profile.

7. The method of claim 5, wherein the protein profile is obtained using flow cytometry or CyTOF.

8. The method of claim 1, wherein the malignant tumor is one of the following: a melanoma tumor, a skin/cutaneous melanoma tumor, a cervical squamous cell carcinoma tumor, an endocervical adenocarcinoma tumor, a liver cancer tumor, a hepatocellular carcinoma tumor, or a sarcoma tumor.

9. The method of claim 1, wherein the ISG+DC inducing agent is dsRNA or an analog thereof.

10. The method of claim 1, wherein the ISG+DC inducing agent is polyI:C.

11. The method of claim 1, wherein the ISG+DC inducing agent is one or more of dsRNA or an analog thereof, polyI:C, a RIG-1 agonist, a MDA5 agonist, a MAVS pathway activator, a TLR3 agonist, or any combination thereof.

12. The method of claim 9, wherein the ISG+DC inducing agent is formulated with nanoparticles.

13. The method of claim 1, wherein a combination of two or more ISG+DC inducing agents is administered to the subject.

14. The method of claim 1, further comprising administering one or more secondary agents to the subject in an effective amount.

15. The method of claim 1, wherein the subject is human.

16. The method of claim 1, further comprising administering a composition comprising an peptide-MHC Class I complex.

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
agtatactca cgccacccac                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cgtatgtatc agtctcagtg                                           20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ggatttcaat gtgaggcggg                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gcttcccatt ctccggtggg                                           20

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
gctggaatta ccgcggct                                             18

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
agaccacaaa cttggagagt cac                                       23

<210> SEQ ID NO 7
<211> LENGTH: 21
<212> TYPE: DNA
<213> ORGANISM: Artificial Sequence

```
<220> FEATURE:
<223> OTHER INFORMATION: Synthetic

<400> SEQUENCE: 7
cttcagcact ttcttccgag a                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atggctgact ttggcatctt                                                20

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
cacagccctc tccatcaact a                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gaacaagtcc acgaagacca g                                              21

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
gctgccgtca ttttctgc                                                  18

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
gtgctgccag cctttgat                                                  18

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcacctgaaa gcctactacc a                                              21
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cggctaccac atccaaggaa                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
gcggtcttag catctccaac                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tgtagtgtgg tgacccttgc                                               20

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
cgtccggctt atccttcc                                                 18

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
catttccgaa tgttcgtcct                                               20

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
gcagctcctt gtcctccat                                                19

<210> SEQ ID NO 20
<211> LENGTH: 18
<212> TYPE: DNA
<213> ORGANISM: Artificial Sequence
<220> FEATURE:
<223> OTHER INFORMATION: Synthetic
```

-continued

```
<400> SEQUENCE: 20
tctcactggc ccgtcatc                                                   18

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
tgaggatggc atagattctg g                                               21

<210> SEQ ID NO 22
<211> LENGTH: 25
<212> TYPE: DNA
<213> ORGANISM: Artificial Sequence
<220> FEATURE:
<223> OTHER INFORMATION: Synthetic

<400> SEQUENCE: 22
ggatgaagta ctggataatc agagg                                           25

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Ser Ile Tyr Arg Tyr Tyr Gly Leu
1               5
```